(12) United States Patent
Magnus et al.

(10) Patent No.: US 8,293,927 B2
(45) Date of Patent: Oct. 23, 2012

(54) EFFICIENT SYNTHESIS OF MORPHINE AND CODEINE

(75) Inventors: Philip D. Magnus, Austin, TX (US); Benjamin P. Fauber, San Francisco, CA (US); Neeraj Sane, Pune (IN)

(73) Assignee: Board of Regents the University of Texas System, Austin, TX (US)

( * ) Notice: Subject to any disclaimer, the term of this patent is extended or adjusted under 35 U.S.C. 154(b) by 250 days.

(21) Appl. No.: 12/778,466

(22) Filed: May 12, 2010

(65) Prior Publication Data

US 2010/0292475 A1    Nov. 18, 2010

(51) Int. Cl.
*C07D 307/94* (2006.01)
(52) U.S. Cl. ...................................... 549/345
(58) Field of Classification Search .................. 549/345
See application file for complete search history.

(56) References Cited

U.S. PATENT DOCUMENTS

| | | | | |
|---|---|---|---|---|
| 5,698,155 | A | 12/1997 | Grosswald et al. | 264/402 |
| 6,136,157 | A | 10/2000 | Lindeberg et al. | 435/7.1 |
| 7,312,191 | B2 | 12/2007 | Rose et al. | 514/19.3 |

OTHER PUBLICATIONS

Barton, D. H. R. et al. (1965) Investigations on the biosynthesis of morphine alkaloids, *Journal of the Chemical Society* 2423-2438.
Hudlicky, T. et al. (1996) Stereoselective Synthesis (Part K), in *Studies in Natural Products Chemistry* (Rahman, A., Ed.), p. 43-154, Elsevier, New York.
Küenburg, B. et al. (1999) Development of a Pilot Scale Process for the Anti-Alzheimer Drug (−)-Galanthamine Using Large-Scale Phenolic Oxidative Coupling and Crystallisation-Induced Chiral Conversion, *Org. Process Res. Dev.* 3(6), 425-431.
Omori, A. T. et al. (2007) Chemoenzymatic Total Synthesis of (+)-Codeine by Sequential Intramolecular Heck Cyclizations via C-B-D Ring Construction, *Synlett 18*, 2859-2862.
PDR Staff (2008) *Physician's Desk Reference, 62nd Edition.*
Perrin, D. D. and Armarego, W. L. F. (1993) *Purification of Laboratory Chemicals*, 3rd ed., Permagon Press, New York.
Rice, K. C. (1980) Synthetic opium alkaloids and derivatives. A short total synthesis of (.+−.)-dihydrothebainone, (.+−.)-dihydrocodeinone, and (.+−.)-nordihydrocodeinone as an approach to a practical synthesis of morphine, codeine, and congeners, *The Journal of Organic Chemistry* 45(15), 3135-3137.
Stahl, P. H. and Wermuth, C. G., (Eds.) (2002) *Handbook of Pharmaceutical Salts: Properties Selection and Use*, Verlag Helvetica Chimica Acta/Wiley-VCH, Zurich.
Szantay, C. et al. (1994) Chapter 2. The Morphine Alkaloids, in *The Alkaloids* (Cordell, G. A., and Brossi, A., Eds.), pp. 128-222, Elsevier Publishers, Academic Press, New York.
Trost, B. M. et al. (2005) Divergent Enantioselective Synthesis of (−)-Galanthamine and (−)-Morphine, *J. Am. Chem. Soc. 127*(42), 14785-14803.
Uchida, K. et al. (2006) Total Synthesis of (±)-Morphine, *Org. Lett.* 8(23), 5311-5313.
Zezula, J. et al. (2007) Design for Morphine Alkaloids by Intramolecular Heck Strategy: Chemoenzymatic Synthesis of 10-Hydroxy-14-epi-dihydrocodeinone via C-D-B Ring Construction, *Synlett 18*, 2863-2867.
Magnus, P. et al. (2009) Concise Syntheses of (−)-Galanthamine and (±)-Codeine via Intramolecular Alkylation of a Phenol Derivative, *J. Am. Chem. Soc. 131*(44), 16045-16047.

*Primary Examiner* — Andrew D Kosar
*Assistant Examiner* — Raymond Covington
(74) *Attorney, Agent, or Firm* — Medlen & Carroll, LLP

(57) ABSTRACT

The present invention relates to methods for the synthesis of morphine, intermediates, salts and derivatives thereof. In preferred embodiments, the invention relates to methods for improving the efficiency and overall yield of said morphine, morphine related derivatives and intermediates thereof. In further embodiments, the invention relates to methods for improving the efficiency and overall yield of galanthamine and intermediates thereof.

42 Claims, 17 Drawing Sheets

Atom and ring numbering for morphine

A 1:1 mixture of stereoisomers at C-16 which are mirror images of one another

4, ($R_1$ = Me, $R_7$ = H, 87%) (±)-codeine
5, ($R_1$ = H, $R_7$ = H) (±)-morphine 1 (±)-Galanthamine    2 (±)-Narwedine    Atom numbering for galanthamine

1 (-)-Galanthamine
$R_1$=Me, $R_{11}$=Me,
$R_{12}$=OH, $R_{13}$=H

N-allylnorgalanthamine
$R_1$=Me, $R_{12}$=OH, $R_{13}$=H

Norgalanthamine
$R_1$=Me, $R_{11}$=H,
$R_{12}$=OH, $R_{13}$=H

N-(14-methylallyl)norgalanthamine
$R_1$=Me, $R_{12}$=OH, $R_{13}$=H

Narwedine
$R_1$=Me, $R_{11}$=Me,
$R_{12}$ + $R_{13}$ = O

EFFICIENT SYNTHESIS OF MORPHINE AND CODEINE

FIELD OF THE INVENTION

The present invention relates to methods for the synthesis of morphine and precursors, intermediates, and derivatives thereof. In preferred embodiments, the invention relates to methods for improving the efficiency and overall yield of said morphine, morphine related derivatives and intermediates thereof. In further embodiments, the invention relates to methods for improving the efficiency and overall yield of galanthamine and intermediates thereof.

BACKGROUND OF THE INVENTION

Morphine is one of the most important analgesics worldwide. The majority of the world's morphine supply is derived from poppy plants found in some of the more politically turbulent areas of western Asia. A related compound, galanthamine, has shown efficacy in the treatment of, inter alia, Alzheimer's disease. However, while morphine remains in high demand worldwide, the lack of effective synthetic methods coupled with the aforementioned instability in areas largely responsible for the natural production of morphine illustrates the tenuous state of current means for obtaining the compound. Similarly, overall yields for galanthamine using current synthetic routes remain poor. Thus, there is a need to develop improved methods for synthesizing morphine and related derivatives for use in pharmaceutical compositions and other medical applications.

SUMMARY OF THE INVENTION

The present invention relates to methods and compositions for the synthesis of galanthamine, morphine and precursors, intermediates (including but not limited to codeine), salts, and derivatives thereof. In addition, pharmaceutical formulations comprising such compositions, as well as methods of treatment comprising administering said compositions), are contemplated. In preferred embodiments, the invention relates to methods for improving the efficiency and overall yield of said morphine, morphine related derivatives and intermediates thereof, as well as the resulting compositions for pharmaceutical formulations and human treatment (e.g. to relieve or prevent pain, to suppress coughing, etc.). In further embodiments, the invention relates to methods for improving the efficiency and overall yield of galanthamine and intermediates thereof, as well as the resulting compositions for pharmaceutical formulations and human treatment (e.g. mild to moderate Alzheimer's). In addition, the methods permit the further efficient synthesis of galanthamine derivatives, such as N-alkyl galanthamine derivatives [e.g. N-allylnorgalanthamine, N-(14-methylallyl)norgalanthamine, etc., see FIG. 10], which are more potent cholinesterase inhibitors than galanthamine.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Other non-carbon groups contemplated by the present invention as candidates for substituting into the compounds described herein include, but are not limited to oxy, amino, amido, imino, thio, thiol, sulfonyl, ammonium, sulfonium, silyl and the substituted versions of these groups.

In some embodiments the terms alkyl, aryl, alkanediyl, alkynyl, arenediyl, aralkyl, heteroarenediyl, heteroaralkyl, heteroaryl, alkenyl, alkenediyl, alkynediyl, acyl, alkylidene, or a substituted version of any of these groups, refer to groups with a number of carbons$\leq 20$. In some embodiments the terms alkyl, aryl, alkanediyl, alkynyl, arenediyl, aralkyl, heteroarenediyl, heteroaralkyl, heteroaryl, alkenyl, alkenediyl, alkynediyl, acyl, alkylidene, or a substituted version of any of these groups, refer to groups with a number of carbons$\leq 12$. In some embodiments the terms alkyl, aryl, alkanediyl, alkynyl, arenediyl, aralkyl, heteroarenediyl, heteroaralkyl, heteroaryl, alkenyl, alkenediyl, alkynediyl, acyl, alkylidene, or a substituted version of any of these groups refer to groups with a number of carbons$\leq 10$. In some embodiments the terms alkyl, aryl, alkanediyl, alkynyl, arenediyl, aralkyl, heteroarenediyl, heteroaralkyl, heteroaryl, alkenyl, alkenediyl, alkynediyl, acyl, alkylidene, or a substituted version of any of these groups, refer to groups with a number of carbons$\leq 8$. In some embodiments, the present invention contemplates allyl, propargyl, and cyclopropyl carbinol derivatives.

In some embodiments (FIG. 3A), the invention relates to a method for forming a cross-conjugated 2,5-cyclohexadienone, comprising i) providing a substituted biphenyl; ii) treating said biphenyl to create an ether. In further embodiments, said biphenyl is treated with an alkenylether or vinylether (e.g. ethylvinyl ether) under a set of conditions to create a biphenyl ether. In one embodiment, the method further comprises iii) treating said ether under conditions (e.g. with a phenol alkylating catalyst) to cause intramolecular phenol alkylation so as to produce a cross-conjugated 2,5-cyclohexadienone (or derivative thereof). In further embodiments, said substituted biphenyl is produced in a Suzuki coupling reaction. In still further embodiments, said substituted biphenyl is produced in an Ullman coupling reaction. In still further embodiments said substituted biphenyl ether is treated under a second set of conditions to form a cross-conjugated 2,5-cyclohexadienone derivative. Some generic embodiments are shown in FIG. 3A. Some specific non-limiting examples of contemplated derivatives are shown in FIG. 3B. In additional embodiments, said substituted biphenyl has the structure:

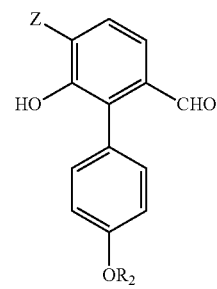

wherein Z is H or $R_1O$, wherein $R_1$ is an alkyl, aryl or heteroaryl group or the like (i.e. other groups such as alkanediyl, alkynyl, arenediyl, aralkyl, heteroarenediyl, heteroaralkyl, alkenyl, alkenediyl, alkynediyl, acyl, alkylidene, non-carbon group, or a substituted version of any of these groups), a protecting group, but not H, and $R_2$ is a protecting group or H. In some embodiments, said protecting group is selected from the group consisting of triisopropylsilyl and tert-butyldimethylsilyl. In further embodiments, said ether has the structure:

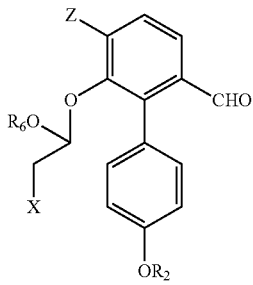

wherein Z is H or $R_1$), wherein $R_1$ is an alkyl, aryl, or heteroaryl group or the like a protecting group but not H; $R_2$ is a protecting group or H; $R_6$ can be alkyl or aryl or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups); and X is a halide or an equivalent leaving group. Some generic embodiments are shown in FIG. 3A. Some specific non-limiting examples of contemplated derivatives are shown in FIG. 3B. In further embodiments, said cross-conjugated 2,5-cyclohexadienone has the structure:

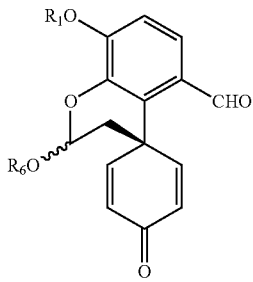

wherein $R_1$ is an alkyl, aryl, or heteroaryl group or the like or a protecting group but not H; and $R_6$ is a protecting group or H. At this point, the synthesis can be directed to galanthamine or to morphine (the steps leading to morphine will be described here and the steps leading to galanthamine will be described below). In one embodiment where the synthesis proceeds to morphine, the method further comprises iv) treating the cross-conjugated 2,5-cyclohexadienone of step iii) with a nitroalkane under Henry reaction conditions so as to create a dihydro-1H-phenanthren-2-one derivative. In additional embodiments, said dihydro-1H-phenanthren-2-one derivative is a nitroalkene. In additional embodiments, said dihydro-1H-phenanthren-2-one derivative is a β-hydroxy nitroalkane. Some generic embodiments are shown in FIG. 4A. Some specific non-limiting examples of contemplated derivatives are shown in FIG. 4B. In some embodiments, said nitroalkene has the structure

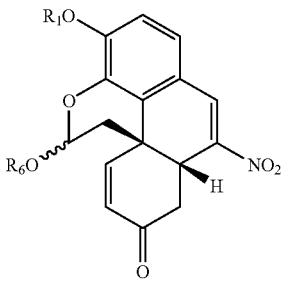

wherein $R_1$ is an alkyl, aryl or heteroaryl group or the like or a protecting group but not H; and $R_6$ can be alkyl or aryl or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups). Some generic embodiments are shown in FIG. 4A. Some specific non-limiting examples of contemplated derivatives are shown in FIG. 4B. In some embodiments, said nitroalkane has the structure

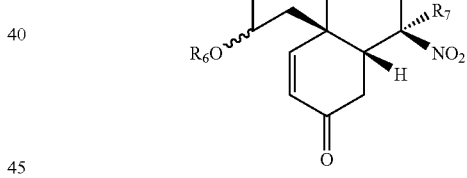

wherein $R_1$ is an alkyl, aryl or heteroaryl group or the like or a protecting group but not H; $R_6$ can be alkyl or aryl or the like, and $R_7$ can be H, alkyl, aryl, or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups). In further embodiments, said dihydro-1H-phenanthren-2-one derivative is in the form of a mixture of epimers. In some embodiments, the invention further comprises v) treating said nitroalkene with a (mild) reducing agent so as to create nitroalkane. Some generic embodiments are shown in FIG. 4A. Some specific non-limiting examples of contemplated derivatives are shown in FIG. 4B. It is noteworthy that only the correct cis-stereochemical relationship between the newly formed B-ring and the C-ring, i.e. at the $C_{13}$ and $C_{14}$ positions, is observed in 15. In further embodiments, said nitroalkane has the structure

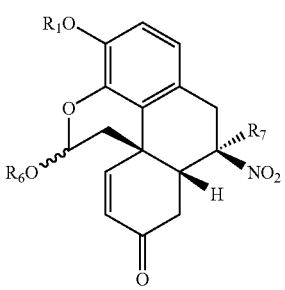

wherein $R_1$ is an alkyl, aryl, or heteroaryl group or a protecting group but not H; $R_6$ can be alkyl or aryl or the like; and $R_7$ can be H, alkyl, aryl, heteroaryl group or the like. In still further embodiments, said nitroalkane is in the form of a mixture of epimers. In additional embodiments, the invention further comprises vi) treating said nitroalkane with a reducing agent so as to create a primary amine. Some generic embodiments are shown in FIG. 4A. Some specific non-limiting examples of contemplated derivatives are shown in FIG. 4B. In some embodiments, said amine has the structure

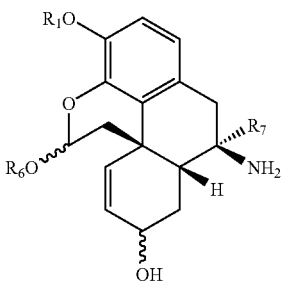

wherein $R_1$ is an alkyl, aryl, or heteroaryl group or the like or a protecting group but not H; $R_6$ can be alkyl/aryl or the like; and $R_7$ can be H, alkyl, aryl, heteroaryl group or the like. In some embodiments, the invention further comprises vii) treating said primary amine with a (mild) reducing agent so as to create a secondary amine. In further embodiments, said secondary amine is the result of intramolecular reductive amination. Some generic embodiments are shown in FIG. 4A. Some specific non-limiting examples of contemplated derivatives are shown in FIG. 4B. In still further embodiments, said secondary amine has the structure

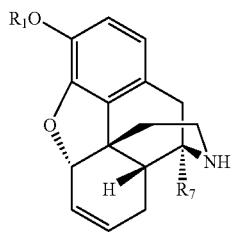

wherein $R_1$ is an alkyl, aryl, or heteroaryl group or the like, a protecting group or H; and $R_7$ can be H or an alkyl, aryl, or heteroaryl group or the like. In additional embodiments, the invention further comprises viii) treating said secondary amine with base so as to create a carbamate derivative. Some generic embodiments are shown in FIG. 4A. Some specific non-limiting examples of contemplated derivatives are shown in FIG. 4B. In some embodiments, said carbamate derivative has the structure

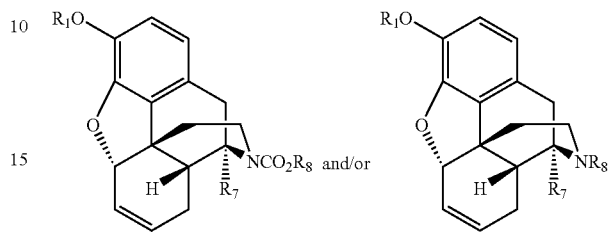

wherein $R_1$ is an alkyl, aryl, heteroaryl group or the like, a protecting group, or H; $R_7$ is H or an alkyl, aryl, or heteroaryl group or the like; and $R_8$ is an alkyl, aryl, or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups). In further embodiments, the invention further comprises ix) treating said carbamate derivative with a halohydantoin so as to create a halohydrin. In still further embodiments, said halohydantoin is 2,2 bromo-3,5 dimethylhydantoin and said halohydrin is a bromohydrin. Some generic embodiments are shown in FIG. 5A. Some specific non-limiting examples of contemplated derivatives are shown in FIG. 5B. In additional embodiments, said bromohydrin has the structure

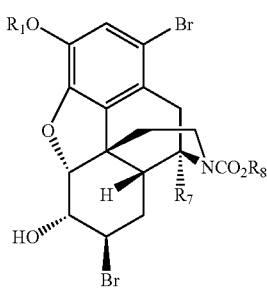

wherein $R_1$ is an alkyl, aryl, or heteroaryl group or the like, a protecting group or H; $R_7$ is H or an alkyl, aryl, or heteroaryl group or the like; and $R_8$ is an alkyl, aryl, or heteroaryl group or the like.

In additional embodiments, the invention further comprises viii) treating said secondary amine with carbon-halide so as to create a tertiary amine derivative. Some generic embodiments are shown in FIG. 4A. Some specific non-limiting examples of contemplated derivatives are shown in FIG. 4B. In some embodiments, said tertiary amine derivative has the structure

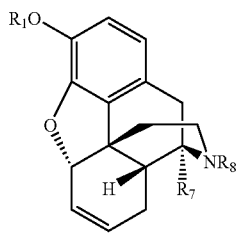

wherein $R_1$ is an alkyl, aryl, heteroaryl group or the like, a protecting group, or H; $R_7$ is H or an alkyl, aryl, or heteroaryl group or the like; and $R_8$ is an alkyl, aryl, or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups).

In some embodiments, further comprising x) treating said halohydrin with base so as to create an epoxide. Some generic embodiments are shown in FIG. 5A. Some specific non-limiting examples of contemplated derivatives are shown in FIG. 5B. In further embodiments, said epoxide has the structure

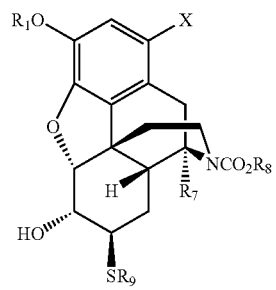

wherein $R_1$ is an alkyl, aryl, or heteroaryl group or the like or a protecting group, or H; $R_7$ is H or an alkyl, aryl, or heteroaryl group or the like; $R_8$ is an alkyl, aryl, or heteroaryl group or the like; and X is a halide or an equivalent leaving group. This epoxide is a novel compound and an important compound, since it allows access to a large range of derivatives (including but not limited to 7-alkyl (or aryl, etc.) derivatives of codeine); the present invention contemplates this 6,7-alpha-epoxide as a composition of matter and in methods for synthesizing downstream derivatives (including but not limited to 7-β substituted 7,8-dihydro derivatives) as pharmaceutical formulations for human treatment. Some specific non-limiting examples of contemplated derivatives are shown in FIG. 9B. In still further embodiments, the invention further comprises xi) treating said epoxide with a reducing agent in the presence of an organic disulfide so as to create a carbo sulfide. Some generic embodiments are shown in FIG. 5A. Some specific non-limiting examples of contemplated derivatives are shown in FIG. 5B. In additional embodiments, said carbo sulfide has the structure wherein $R_1$ is an alkyl, aryl, or heteroaryl group or the like, or a protecting group, or H; $R_7$ is an H or an alkyl, aryl, or heteroaryl group or the like; $R_8$ is an alkyl, aryl, or heteroaryl group or the like; $R_9$ is an alkyl, aryl, or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups); and X is a halide or an equivalent leaving group. In still further embodiments, the invention further comprises xi) treating said epoxide with a reducing agent in the presence of an organic disulfide so as to create a phenyl sulfide. Some generic embodiments are shown in FIG. 5A. Some specific non-limiting examples of contemplated derivatives are shown in FIG. 5B. In additional embodiments, said phenyl sulfide has the structure

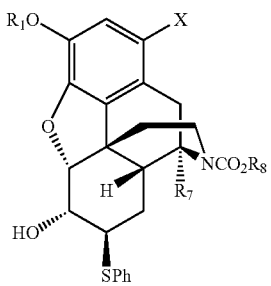

wherein $R_1$ is an alkyl, aryl, or heteroaryl group or the like, or a protecting group, or H; $R_7$ is an H or an alkyl, aryl, or heteroaryl group or the like; $R_8$ is an alkyl, aryl, or heteroaryl group or the like; and X is a halide or an equivalent leaving group. In additional embodiments, the invention further comprises xii) treating said phenylsulfide with an oxidizing agent (preferably hydrogen peroxide) in the presence of an acidic alcohol such as a halogenated alcohol (preferably hexafluoroisopropanol) so as to create a sulfoxide. Some generic embodiments are shown in FIG. 9A. Some specific non-limiting examples of contemplated derivatives are shown in FIG. 9B. In one embodiment, said sulfoxide has the structure:

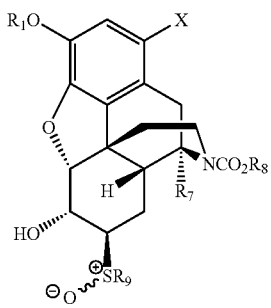

wherein $R_1$ is an alkyl, aryl, or heteroaryl group or the like, or a protecting group, or H; $R_7$ is an H or an alkyl, aryl, or heteroaryl group or the like; $R_8$ is an alkyl, aryl, or heteroaryl group or the like; $R_9$ is an alkyl, aryl, or heteroaryl group or the like; and X is a halide or an equivalent leaving group. In further embodiments, the invention further comprises xiii) heating said sulfoxide to give an allylic alcohol. Some generic embodiments are shown in FIG. 5A. Some specific non-limiting examples of contemplated derivatives are shown in FIG. 5B. In some embodiments, said allylic alcohol has the structure

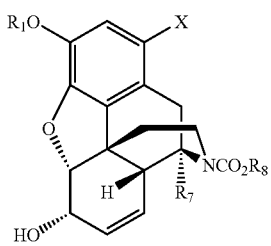

wherein $R_1$ is an alkyl, aryl, or heteroaryl group or the like, or a protecting group, or H; $R_7$ is an H or an alkyl, aryl, or heteroaryl group or the like; $R_8$ is an alkyl, aryl, or heteroaryl group or the like; and X is a halide or an equivalent leaving group. In further embodiments, the invention further comprises xiv) treating said allylic alcohol with a reducing agent so as to create codeine. In still further embodiments, the invention further comprises xv) treating said codeine with a (preferably strong) Lewis acid so as to create morphine.

In still further embodiments, the invention further comprises treating said epoxide with a Grignard reagent so as yield an epoxide ring opened 6-hydroxy,7-adduct. Some generic embodiments are shown in FIG. 9A. Some specific non-limiting examples of contemplated derivatives are shown in FIG. 9B. In additional embodiments, said epoxide ring opened 6-hydroxy,7-adduct has the structure

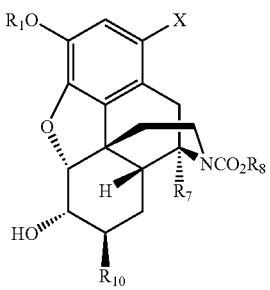

wherein $R_1$ is an alkyl, aryl, or heteroaryl group or the like, or a protecting group, or H; $R_7$ is an H or an alkyl, aryl, or heteroaryl group or the like; $R_8$ is an alkyl, aryl, or heteroaryl group or the like $R_{10}$ is an alkyl, aryl, or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups) or H; and X is a halide or an equivalent leaving group.

In some embodiments, the invention relates to a composition of the formula (or salt thereof):

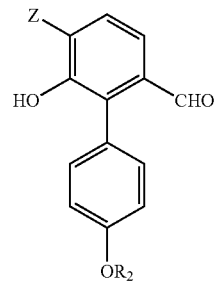

wherein Z is H or $R_1O$, wherein $R_1$ is an alkyl, aryl, or heteroaryl group or the like or a protecting group, but not H; $R_2$ is a protecting group. In one embodiment, the protecting group is selected from a group consisting of triisopropylsilyl and tert-butyldimethylsilyl, and (in general) $SiR_3R_4R_5$ where $R_3$ can be alkyl, aryl, or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups), $R_4$ can be alkyl, aryl, or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups), and $R_5$ can be alkyl, aryl, or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups). In further embodiments, the inventions relates to a composition of the formula (or salt thereof):

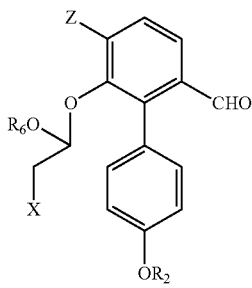

wherein Z is H or $R_1O$, wherein $R_1$ is an alkyl, aryl, or heteroaryl group or the like or a protecting group, but not H; $R_2$ is a protecting group or H; $R_6$ can be alkyl or aryl or the like; and X is a halide or an equivalent leaving group. In still further embodiments, the invention relates to a composition of the formula (or salt thereof):

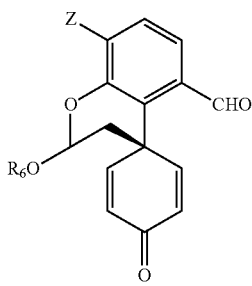

wherein Z is H or $R_1O$, wherein $R_1$ is an alkyl, aryl, heteroaryl group or the like, or a protecting group, or H; and $R_6$ is a protecting group. In additional embodiments, the invention relates to a composition of the formula (or salt thereof):

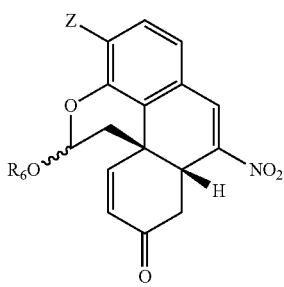

wherein Z is H or $R_1O$, wherein $R_1$ is an alkyl, aryl, heteroaryl group or the like or a protecting group, or H; and $R_6$ can be alkyl or aryl or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups). In some embodiments, the invention relates to a composition of the formula (or salt thereof).

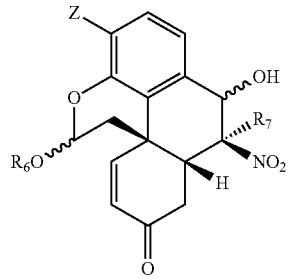

wherein Z is H or $R_1O$, wherein $R_1$ is an alkyl, aryl, heteroaryl group or the like or a protecting group, or H; $R_6$ can be alkyl, aryl or the like; and $R_7$ can be H, alkyl, aryl, or heteroaryl group or the like. In further embodiments, the invention relates to a composition of the formula (or salt thereof):

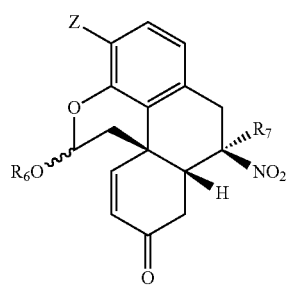

wherein Z is H or $R_1O$, wherein $R_1$ is an alkyl, aryl, heteroaryl group or the like or a protecting group, or H; $R_6$ can be alkyl, aryl, or the like; and $R_7$ can be H, alkyl, aryl or heteroaryl group, or the like. In still further embodiments, the invention relates to a composition of the formula (or salt thereof):

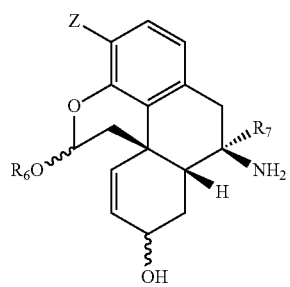

wherein Z is H or $R_1O$, wherein $R_1$ is an alkyl, aryl, heteroaryl group or the like or a protecting group, or H; $R_6$ can be alkyl, aryl, or the like; and $R_7$ can be H, alkyl, aryl, or heteroaryl group or the like. In additional embodiments, the invention relates to a composition of the formula (or salt thereof):

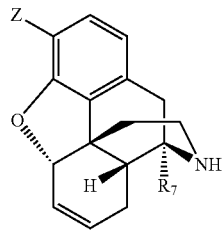

wherein Z is H or R₁O, wherein R₁ is an alkyl, aryl, heteroaryl group or the like or a protecting group, or H; and R₇ can be H or an alkyl, aryl, or heteroaryl group, or the like. In some embodiments, the invention relates to a composition of the formula (or salt thereof):

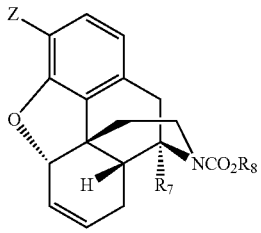

wherein Z is H or R₁O, wherein R₁ is an alkyl, aryl, or heteroaryl group or the like or a protecting group, or H; R₇ is H or an alkyl, aryl, or heteroaryl group or the like; and R₈ is an alkyl, aryl, or heteroaryl group or the like. In further embodiments, the invention relates to a composition of the formula (or salt thereof):

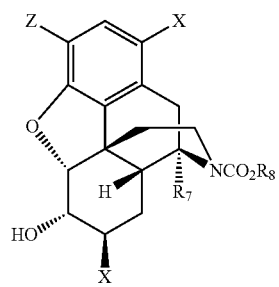

wherein Z is H or R₁O, wherein R₁ is an alkyl, aryl, or heteroaryl group or the like or a protecting group, or H; R₇ is H or an alkyl, aryl, or heteroaryl group or the like; R₈ is an alkyl, aryl, or heteroaryl group or the like; and X is a halide or an equivalent leaving group. In still further embodiments, the invention relates to a composition of the formula (or salt thereof):

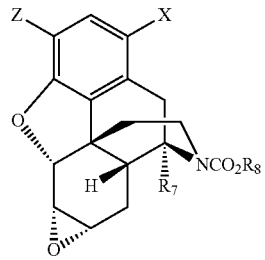

wherein Z is H or R₁O, wherein R₁ is an alkyl, aryl, or heteroaryl group or the like or a protecting group, or H; R₇ is H or an alkyl, aryl, or heteroaryl group or the like; R₈ is an alkyl, aryl, or heteroaryl group or the like; and X is a halide or an equivalent leaving group. In additional embodiments, the invention relates to a composition of the formula (or salt thereof):

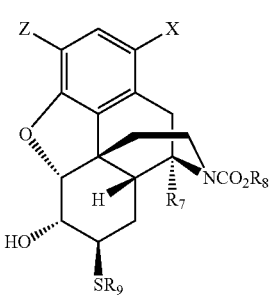

wherein Z is H or R₁O, wherein R₁ is an alkyl, aryl, or heteroaryl group or the like or a protecting group, or H; R₇ is H or an alkyl, aryl, or heteroaryl group or the like; R₈ is an alkyl, aryl, or heteroaryl group or the like; R₉ is an alkyl, aryl, or heteroaryl group or the like; and X is a halide or an equivalent leaving group. In some embodiments, the invention relates to a composition of the formula (or salt thereof):

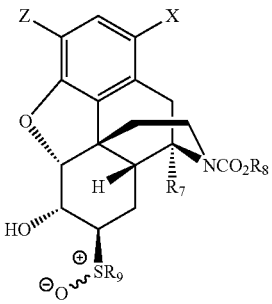

wherein Z is H or R₁O, wherein R₁ is an alkyl, aryl, or heteroaryl group or the like or a protecting group, or H; R₇ is H or an alkyl, aryl, or heteroaryl group or the like; R₈ is an alkyl, aryl, or heteroaryl group or the like; R₉ is an alkyl, aryl, or heteroaryl group or the like; and X is a halide or an equivalent leaving group. In further embodiments, the invention relates to a composition of the formula (or salt thereof):

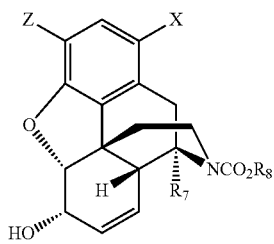

wherein Z is H or $R_1O$, wherein $R_1$ is an alkyl, aryl, or heteroaryl group or the like or a protecting group or H, or H; $R_7$ is H or an alkyl, aryl, or heteroaryl group or the like; $R_8$ is an alkyl, aryl, or heteroaryl group or the like; and X is a halide or an equivalent leaving group. In still further embodiments, the invention relates to a composition of the formula (or salt thereof):

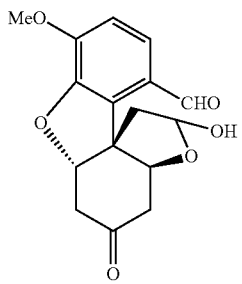

In additional embodiments, the invention relates to a composition of the formula (or salt thereof):

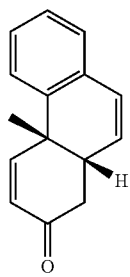

In some embodiments, the invention relates to a method of synthesizing a compound comprising: mixing 4-bromophenol, imidazole and 1,2-dichloroethane at a temperature between 20° C. and 25° C., preferably 23° C., to form a first solution, mixing triisopropylsilylchloride with said first solution for at least 10 hours, preferably at least 11 hours and more preferably 12 hours, to form a second mixture, transferring said second mixture to an aqueous $NH_4Cl$ to form a third solution, combining said third solution with $CH_2Cl_2$ to form a fourth solution, combining said fourth solution with a brine solution to form a fifth solution, mixing said fifth solution with $Na_2SO_4$, separating said fifth solution from said $Na_2SO_4$ to give a sixth solution, reducing the volume of said sixth solution using a means for reducing said volume, and recovering said compound. In further embodiments, said means for reducing volume is a vacuum system. In still further embodiments, said compound is:

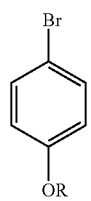

In further embodiments, R is selected from the group consisting of -TIPS (triisopropylsilyl) and -TBDMS (tert-butyldimethylsilyl). In additional embodiments, the percent yield of said compound is at least 95%, preferably at least 97% and more preferably 99%.

In some embodiments, the invention relates to a method of synthesizing a compound comprising: mixing isovanillin, anhydrous sodium acetate, iron powder, glacial acetic acid and argon gas to form a first solution, combining a bromine solution further comprising acetic acid with said first solution to form a second solution, combining said second solution with water maintained at a temperature between 0° C. and 10° C. to form a third solution, filtering said third solution, reducing the volume of said third solution using a means for reducing said volume, and recovering said compound. In further embodiments, said means for reducing volume is a vacuum system. In still further embodiments, said compound is:

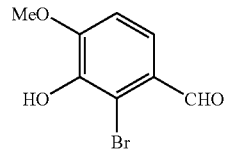

In additional embodiments, the percent yield of said compound is at least 75%, preferably at least 77% and more preferably 79% or more.

In some embodiments, the invention further comprises: mixing (4-bromo-phenoxy)-triisopropylsilane and THF at a temperature of at least −75° C., preferably −78° C. to form a first solution, mixing said first solution with a composition comprising n-BuLi further comprising THF to form a second solution, stirring said second solution for at least 60 minutes, preferably 70 minutes, at a temperature of at least −75° C., more preferably −78° C., mixing said second solution with a solution of $B(OPr^i)_3$ to form a third solution, stirring said third mixture for at least 10 hours, preferably at least 11 hours and more preferably 12 hours, at a temperature of at least 20° C., preferably 23° C., mixing said third mixture with a solution comprising 10% aqueous $KHSO_4$ to form a fourth solution, mixing said fourth solution with EtOAc to form a fifth solution, mixing said fifth solution with a brine solution to form a sixth solution, i) mixing said sixth solution with $Na_2SO_4$, reducing the volume of said sixth solution using a means for using a means for reducing said volume to obtain a first solid, purifying said first solid using a first means for purification to form a second solid, mixing said second solid with toluene, and recovering said compound. In further embodiments, said means for reducing volume is a vacuum system. In still further embodiments, said compound is:

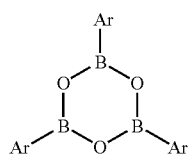

In even further embodiments, Ar is:

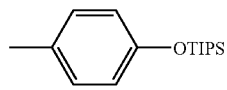

In additional embodiments, the percent yield of said compound is at least 75%, preferably 76% or more.

In some embodiments, the invention further comprises: mixing 1,4-dioxane, water, $K_2CO_3$, 2,6-di-tert-butyl-4 methylphenol, and tricyclohexylphoshine to form a first solution, stirring said first solution for at least 10 minutes, preferably 15 minutes at a temperature of at least 20° C., preferably 23° C., mixing said first solution with [Pd$_2$(dba)$_3$] to form a second solution, refluxing said second solution for at least 45 minutes, preferably 55 minutes and more preferably 60 minutes, mixing said second solution with aqueous $NH_4Cl$ to form a third solution, mixing said third solution with EtOAc to form a fourth solution, mixing said fourth solution with a brine solution to form a fifth solution, mixing said fifth solution with $Na_2SO_4$, separating said fifth solution from said $Na_2SO_4$, reducing the volume of said fifth solution using a means for reducing said volume, and recovering said compound. In further embodiments, said means for reducing volume is a vacuum system. In still further embodiments, said compound is:

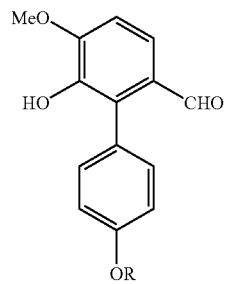

In additional embodiments, R is TIPS. In some embodiments, the percent yield of said compound is at least 85%, preferably at least 95% and more preferably 96%. In some embodiments, the invention relates to a method for synthesizing a compound comprising: mixing bromine and $CH_2Cl_2$ at a temperature of 0° C. to form a first solution, mixing said first solution with ethyl vinyl ether to form a second solution, stirring said second solution for at least 15 minutes, preferably 20 minutes, at 0° C., mixing said second solution with N,N-diisopropylamine to form a third solution, mixing said third solution with a mixture comprising $CH_2Cl_2$ to form a fourth solution, stirring said fourth solution for at least 10 hours, preferably at least 11 hours and more preferably 12 hours, at a temperature of at least 20° C., more preferably 23° C., mixing said fourth solution with saturated aqueous $NaHCO_3$ to form a fifth solution, mixing said fifth solution with $CH_2Cl_2$ to form a sixth solution, mixing said sixth solution with a brine solution to form a seventh solution, mixing said seventh solution with $Na_2SO_4$, separating said seventh solution from said $Na_2SO_4$, reducing the volume of said seventh solution using a means for reducing said volume, and recovering said compound. In further embodiments, said means for reducing volume is a vacuum system. In still further embodiments, said compound is:

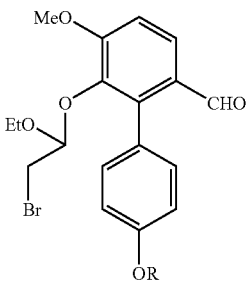

In additional embodiments, R is TIPS. In some embodiments, the percent yield of said compound is at least 95%, preferably at least 97% and more preferably at least 99%.

In some embodiments, the invention further comprises: mixing CsF and DMF to form a first solution, refluxing said first solution for at least one hour, mixing said first mixture with saturated aqueous $NaHCO_3$ to form a second mixture, mixing said second mixture with EtOAc to form a third mixture, mixing said third solution with a brine solution to form a fourth solution, mixing said fourth solution with $Na_2SO_4$, separating said fourth solution from said $Na_2SO_4$, reducing the volume of said fourth solution using a means for reducing said volume, and recovering said compound. In further embodiments, said means for reducing volume is a vacuum system. In further embodiments, said compound is:

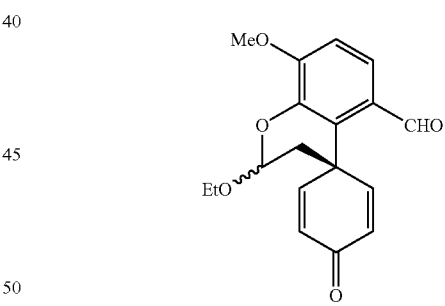

In still further embodiments, the percent yield of said compound is at least 80%, preferably at least 85% and more preferably 90% or more.

In some embodiments, the invention further comprises: adding nitromethane to form a first solution, mixing $NH_4OAc$ and acetic acid with said first solution to form a second solution, refluxing said second solution for at least one hour, preferably two hours, mixing said second solution with a brine solution to form a third solution comprising an aqueous layer and a non-aqueous layer, removing said aqueous layer from said third solution, mixing said aqueous layer with ether to form a fourth solution, mixing said fourth layer with $Na_2SO_4$, separating said fourth layer from said $Na_2SO_4$, reducing the volume of said fourth solution using a means for reducing said volume, and recovering said mixture of compounds. In further embodiments, said means for reducing volume is a vacuum system. In still further embodiments, said mixture of compounds comprises:

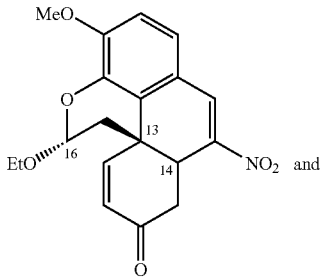 and

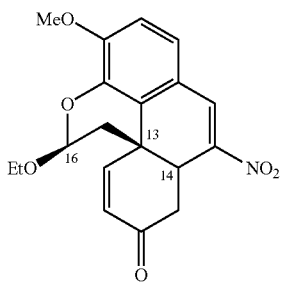

In additional embodiments, the percent yield of said mixture of compounds is at least 50%, preferably 90% and more preferably 97% or more.

In some embodiments, the invention further comprises: mixing THF and phosphate buffer to form a first solution, mixing said first solution with NaBH$_3$CN at a temperature of 0° C. to form a second solution, stirring said second solution for at least 30 minutes, preferably 45 minutes and more preferably 60 minutes, mixing said second solution with aqueous NH$_4$Cl to form a third solution, mixing said third solution with EtOAc to form a fourth solution, mixing said fourth solution with a brine solution to form a fifth solution, mixing said fifth solution with Na$_2$SO$_4$, separating said fifth solution from said Na$_2$SO$_4$, reducing the volume of said fifth solution using a means for reducing said volume, and recovering said mixture of compounds. In further embodiments, said means for reducing volume is a vacuum system. In still further embodiments, said mixture of compounds comprises:

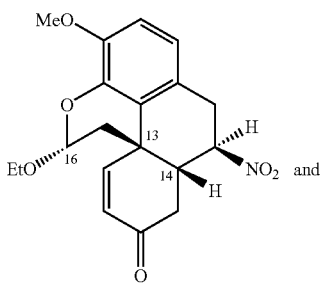 and

-continued

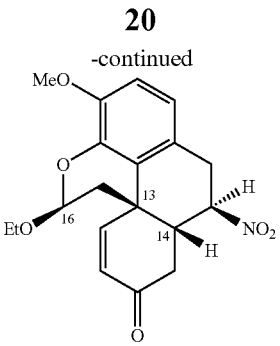

In additional embodiments, the percent yield of said mixture of compounds is at least 80%, preferably at least 85% and more preferably at least 88%. In some embodiments, the invention further comprises: mixing THF and an argon atmosphere to form a first solution, cooling said first solution to a temperature of at least −75° C., preferably −78° C., mixing said first solution with LiAlH$_4$ to form a second solution, stirring said second solution at a temperature of at least −75° C., preferably −78° C., for at least 30 minutes, preferably at least 45 minutes and more preferably 60 minutes, raising the temperature of said second solution to at least 20° C. over a time period of at least six hours, preferably at least seven hours and more preferably eight hours, mixing said second solution with aqueous Na$_2$SO$_4$ at a temperature of 0° C. to form a first salt, mixing said first salt with ether to form a third solution, filtering said third solution using a means for filtering, mixing said third solution with a brine solution to form a fourth solution, combining said fourth solution with Na$_2$SO$_4$, separating said fourth solution from said Na$_2$SO$_4$, reducing the volume of said fourth solution using a means for reducing said volume, and recovering said mixture of compounds. In further embodiments, said means for reducing volume is a vacuum system. In still further embodiments, said mixture of compounds comprises:

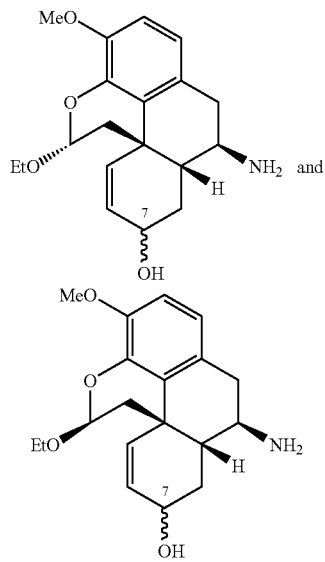

In additional embodiments, the overall percent yield of said mixture of compounds is at least 70% and preferably 72% or more.

In some embodiments, the invention further comprises: mixing dioxane to form a first solution, mixing said first solution with HCl to form a second solution, stirring said second solution for at least 5 minutes, preferably 10 minutes, mixing said second solution with NaCNBH₃ to form a third solution, refluxing said third solution for at least three hours, preferably at least four hours and more preferably five hours, cooling said third solution to a temperature of at least 20° C., mixing said third solution with diethyl ether and NaOH to form a fourth solution, mixing said fourth solution with a brine solution to form a fifth solution, separating said fifth solution from said Na₂SO₄, reducing the volume of said fifth solution using a means for reducing said volume, and recovering said compound. In further embodiments, said means for reducing volume is a vacuum system. In still further embodiments, said compound is:

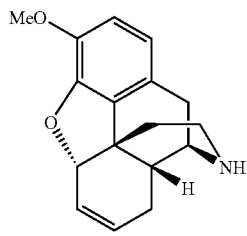

In additional embodiments, the overall yield of said compound is at least 60%, preferably at least 65% and more preferably 66% or more. In some embodiments, the invention relates to a method for synthesizing a compound comprising: mixing CH₂Cl₂ to form a first solution, reducing the temperature of said first solution to 0° C., mixing said first solution with triethylamine and ethyl chloroformate to form a second solution, stirring said second solution at a temperature of 0° C. for at least 30 minutes, preferably 60 minutes, mixing said second solution with saturated aqueous NH₄Cl to form a third solution, mixing said third solution with CH₂Cl₂ to form a fourth solution, mixing said fourth solution with a brine solution to form a fifth solution, mixing said fifth solution with Na₂SO₄, separating said fifth solution from said Na₂SO₄, reducing the volume of said fifth solution using a means for reducing said volume, and recovering said compound. In further embodiments, said means for reducing volume is a vacuum system. In still further embodiments, said compound is:

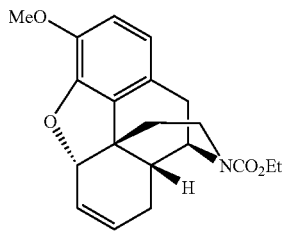

In additional embodiments, the overall yield of said compound is at least 85%, preferably at least 89% or more.

In some embodiments, the invention relates to a method for synthesizing a compound comprising: mixing CH₂Cl₂ to form a first solution, reducing the temperature of said first solution to 0° C., mixing said first solution with methylbromide to form a second solution, stirring said second solution at a temperature of 0° C. for at least 30 minutes, preferably 60 minutes<reducing the volume of said fifth solution using a means for reducing said volume, and recovering said compound. In further embodiments, said means for reducing volume is a vacuum system. In still further embodiments, said compound is:

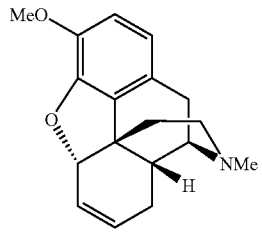

In some embodiments, the invention further comprises: mixing acetone and H₂O to form a first solution, mixing said first solution with 2,2-bromo-3,5-dimethylhydantoin over a period of at least 3 minutes to form a second solution, covering said second solution using a means for covering, stirring said second solution for at least 10 hours, preferably at least 11 hours and more preferably 12 hours, mixing said second solution with saturated NH₄Cl to form a third solution, mixing said third solution with water to form a fourth solution, mixing said fourth solution with ethyl acetate to form a fifth solution, mixing said fifth solution with a brine solution to form a sixth solution, mixing said sixth solution with Na₂SO₄, separating said sixth solution from said Na₂SO₄, reducing the volume of said sixth solution using a means for reducing said volume, and recovering said compound. In further embodiments, said means for reducing volume is a vacuum system. In still further embodiments, said means for covering comprises an aluminum foil sheet. In additional embodiments, said compound is:

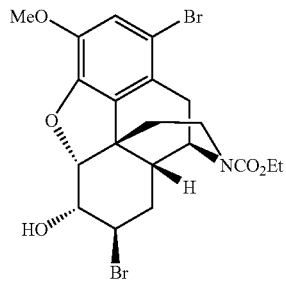

In some embodiments, the overall yield of said compound is at least 95%, preferably 97% or more.

In some embodiments, the invention further comprises: mixing toluene to form a first solution, mixing said first solution with KOH to form a second solution, heating said second solution at a temperature of at least 70° C., preferably at least 75° C. and more preferably 80° C., for a time period of at least 2 hours, preferably 3 hours, reducing the temperature of said second solution, mixing said second solution with water to form a third solution, mixing said third solution with ethyl acetate to form a fourth solution, mixing said fourth solution with a brine solution to form a fifth solution, mixing said fifth solution with Na₂SO₄, separating said fifth solution from said Na₂SO₄, reducing the volume of said fifth solution using a means for reducing said volume, recovering a crude extract comprising said compound, and purifying said crude extract. In further embodiments, said means for reducing volume is a vacuum system. In still further embodiments, said compound is:

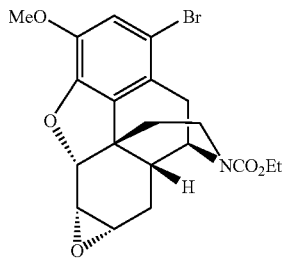

In additional embodiments, the overall yield of said compound is at least 90%, preferably at least 95% or more.

In some embodiments, the invention relates to a method for synthesizing a compound comprising: mixing diphenyl disulfide and ethanol to form a first solution, mixing said first solution with NaBH$_4$ over a time period of at least 3 minutes, preferably 5 minutes, to form a second solution, stirring said second solution for at least 10 minutes, preferably 15 minutes, mixing said second solution and ethanol to form a third solution, stirring said third solution at a temperature of at least 20° C. for a time period of at least 1 hour, preferably 2 hours, mixing said third solution with water to form a fourth solution, mixing said fourth solution with CH$_2$Cl$_2$ to form a fifth solution, mixing said fifth solution with a brine solution to form a sixth solution, mixing said sixth solution with Na$_2$SO$_4$, separating said sixth solution from said Na$_2$SO$_4$, reducing the volume of said sixth solution using a means for reducing said volume, and recovering said compound. In further embodiments, said means for reducing volume is a vacuum system. In still further embodiments, said compound is:

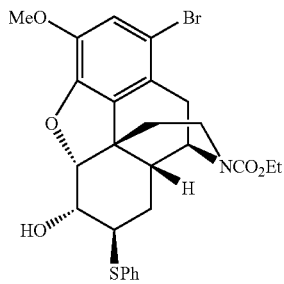

In additional embodiments, the overall yield of said compound is at least 95%, preferably at least 97% and more preferably 99%. In some embodiments, the invention further comprises: mixing hexafluoroisopropanol to form a first solution, mixing said first solution with hydrogen peroxide to form a second solution, stirring said second solution for a time period of at least 10 minutes, preferably 15 minutes, mixing said second solution with water to form a third solution, mixing said third solution with saturated aqueous Na$_2$SO$_3$ to form a fourth solution, mixing said fourth solution with CH$_2$Cl$_2$ to form a fifth solution, mixing said fifth solution with a brine solution to form a sixth solution, mixing said sixth solution with Na$_2$SO$_4$, separating said sixth solution from said Na$_2$SO$_4$, reducing the volume of said sixth solution using a means for reducing said volume, and recovering said compound. In further embodiments, said means for reducing volume is a vacuum system. In still further embodiments, said compound is:

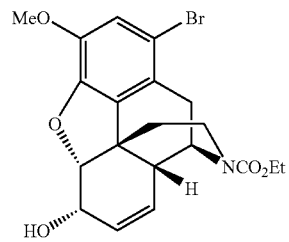

In additional embodiments, the overall yield of said compound is at least 80%, preferably at least 90%, and more preferably 93% or more.

In some embodiments, the invention further comprises: mixing THF to form a first solution, mixing said first solution with LiAlH$_4$ to form a second solution, stirring said second solution at a temperature of at least 20° C. for a time period of at least 4 hours, preferably at least 5 hours and more preferably 6 hours, reducing the temperature of said second solution to 0° C., mixing said second solution with saturated aqueous Na$_2$SO$_4$ to form a third solution, filtering said third solution with Celite, mixing said third solution with diethyl ether to form a fourth solution, mixing said fourth solution with Na$_2$SO$_4$, separating said fourth solution from said Na$_2$SO$_4$, reducing the volume of said fourth solution using a means for reducing said volume, and recovering said compound. In further embodiments, said means for reducing volume is a vacuum system. In still further embodiments, said compound is:

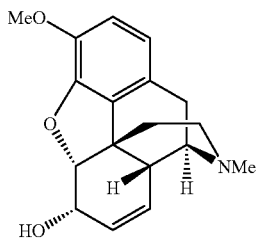

In additional embodiments, the overall yield of said compound is at least 80%, preferably at least 85% and more preferably 87% or more. In some embodiments, the invention further comprises: mixing chloroform to form a first solution, mixing said first solution with boron tribromide to form a second solution, stirring said second solution at a temperature of at least 20° C. for a time period of at least 15 minutes, preferably 20 minutes, mixing said second solution with NH$_4$OH at a temperature of 0° C. to form a third solution, mixing said third solution with a mixture of CH$_2$Cl$_2$ and ethanol to form a fourth solution, mixing said fourth solution with a brine solution to form a fifth solution, mixing said fifth solution with Na$_2$SO$_4$, separating said fifth solution from said Na$_2$SO$_4$, reducing the volume of said fifth solution using a means for reducing said volume to produce an extract, mixing said extract with a composition comprising SiO$_2$, CH$_2$Cl$_2$ and ethanol, and recovering said compound. In further embodiments, said means for reducing volume is a vacuum system. In still further embodiments, said compound is:

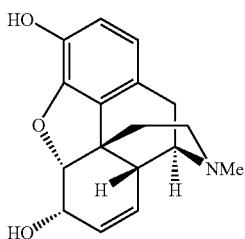

In additional embodiments, the overall yield of said compound is at least 80%, preferably at least 85% and more preferably 86% or more.

In some embodiments, the invention further comprises: mixing HCl and dioxane to form a first solution, refluxing said first solution to produce a first compound, mixing said first compound with a composition comprising MeNH$_2$, THF, NaBH(OAc)$_3$ and AcOH at a temperature of at least 50° C., preferably 60° C., to produce a second compound, and mixing said second compound with L-Selectride under conditions such that a third compound is produced. In further embodiments, said first compound is:

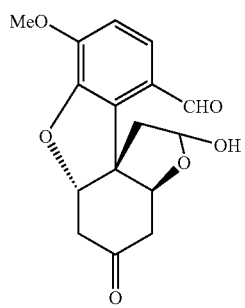

In still further embodiments, said second compound is:

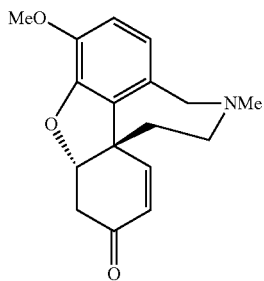

In additional embodiments, said third compound is:

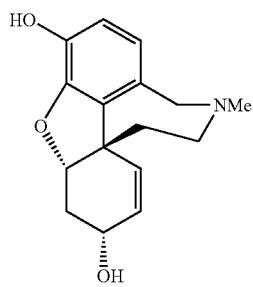

In some embodiments, the overall yield of said first compound is at least 85% or more. In further embodiments, the overall yield of said second compound is at least 65% or more. In still further embodiments, the overall yield of said third compound is at least 55% or more.

In one embodiment, the invention relates to improved methods for the synthesis of galanthamine, derivatives, salts and intermediates thereof. Galanthamine ((4aS,6R,8aS)-5,6,9,10,11,12-hexahydro-3-methoxy-11-methyl-4-aH-[1]benzofuro[3a,3,2-ef]-[2]-benzazepin-6-ol; C$_{17}$H$_{21}$NO$_3$; MW=287), an amaryllidaceae alkaloid. In one embodiment, the compound is contemplated for early treatment of Alzheimer's disease. As noted above, in one embodiment, the present invention contemplates that the early synthesis steps for morphine and galanthamine are shared (e.g. up to the formation of the cross-conjugated 2,5-cyclohexadienone). As noted above, the synthesis can thereafter go in the direction of morphine (the steps for which have been described above) or galanthamine, intermediates, derivatives and salts thereof (the steps for which are described below). For example, in some embodiments where the synthesis is directed towards galanthamine, the present invention further comprises: treating the cross-conjugated 2,5-cyclohexadienone with acid under conditions to cause acid catalyzed hydrolysis of said cross-conjugated 2,5-cyclohexadienone so as to form an aldehyde-lactol, said aldehyde lactol comprising a acyl (carbonyl) group. In a preferred embodiment, said cross-conjugated 2,5-cyclohexadienone is:

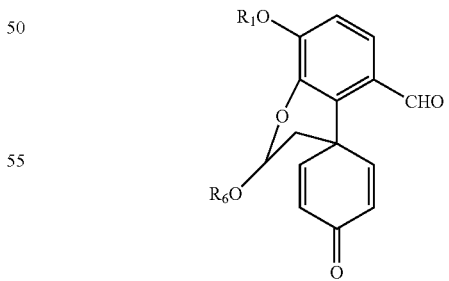

wherein R$_1$ is an alkyl, aryl or heteroaryl group or the like or a protecting group but not H; R$_6$ is an alkyl, aryl or heteroaryl group or the like or a protecting group but not H. In still further embodiments, said aldehyde-lactol compound is:

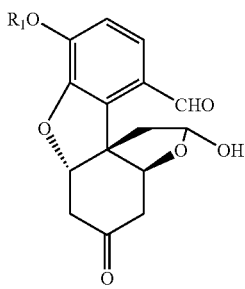

wherein $R_1$ is an alkyl, aryl or heteroaryl group or the like or a protecting group. In some embodiments, the invention further comprises: treating said aldehyde-lactol under conditions such that said acyl (carbonyl) group is converted to an amine by reductive amination so as to form (±) narwedine (including but not limited to an N-alkyl, aryl, heteroaryl, allyl, cyclopropyl carbinol, or n-propargyl derivative thereof).

In some embodiments, the invention further comprises: wherein (±) narwedine is formed sequentially in the same reaction after the formation of a first intermediate, followed by a second intermediate. In some embodiments, the invention further comprises: wherein a narwedine derivative is formed sequentially in the same reaction after the formation of a first intermediate, followed by a second intermediate. In some embodiments, the invention further comprises wherein said first intermediate is an amino-lactol (including but not limited to an N-alkyl, aryl, heteroaryl, allyl, cyclopropyl carbinol, or n-propargyl derivative thereof). In still further embodiments, said compound is:

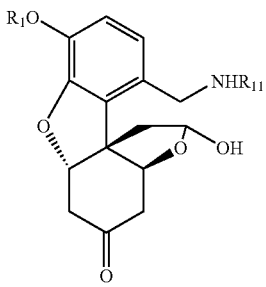

wherein $R_1$ is an alkyl, aryl or heteroaryl group or the like or a protecting group; $R_{11}$ is an alkyl, aryl or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, methyl, allyl, cyclopropyl, carbinol, n-propargyl, non-carbon group, or a substituted version of any of these groups) or a protecting group or H.

In some embodiments, the invention further comprises wherein said second intermediate is a carbinolamine ether (a "hemiaminal") (including but not limited to an N-alkyl, aryl, heteroaryl, allyl, cyclopropyl carbinol, or n-propargyl derivative thereof). In still further embodiments, said compound is:

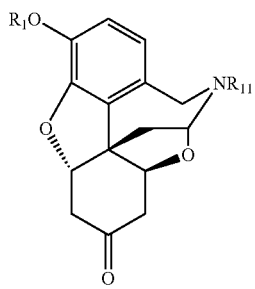

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; and $R_{11}$ is an alkyl, aryl or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, methyl, allyl, cyclopropyl, carbinol, n-propargyl, non-carbon group, or a substituted version of any of these groups) or a protecting group or H.

In still further embodiments, said (±) narwedine has the structure:

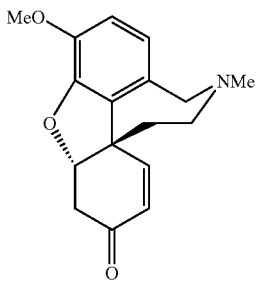

In some embodiments, said narwedine derivative has the structure:

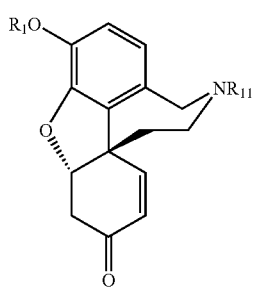

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; and $R_{11}$ is an alkyl, aryl or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, Methyl, allyl, cyclopropyl, carbinol, n-propargyl, non-carbon group, or a substituted version of any of these groups) or a protecting group or H.

In some embodiments, the invention further comprises: reducing said narwedine derivative to a galanthamine derivative with a reducing agent. Some generic embodiments are shown in FIG. 7A. Some specific non-limiting examples of contemplated derivatives are shown in FIG. 7B. Some specific non-limiting examples of contemplated derivatives are shown in FIG. 7C. In some embodiments, said galanthamine derivative has the structure:

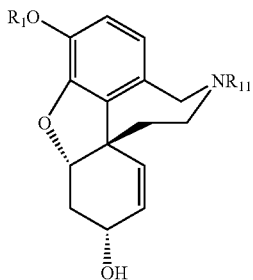

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; and $R_{11}$ is an alkyl, aryl or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, methyl, allyl, cyclopropyl, carbinol, n-propargyl, non-carbon group, or a substituted version of any of these groups) or a protecting group or H.

In some embodiments, said a galanthamine derivative is N-(14-methylallyl)norgalanthamine. In some embodiments, said a galanthamine derivative is N-(14-methylallyl)norgalanthamine has the structure:

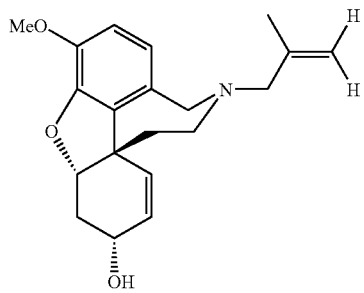

In some embodiments, said a galanthamine derivative is N-allylnorgalanthamine. In some embodiments, said a galanthamine derivative is N-allylnorgalanthamine has the structure:

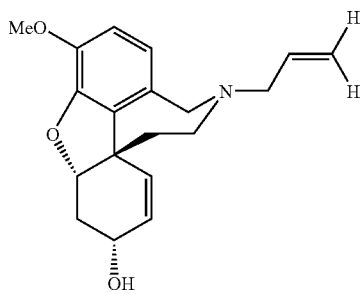

In some embodiments, said a galanthamine derivative is Norgalanthamine. In some embodiments, said a galanthamine derivative is Norgalanthamine has the structure:

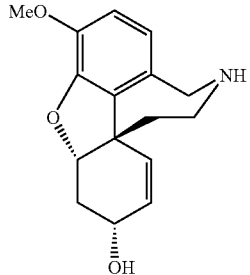

In some embodiments, the invention further comprises: resolving said (±) narwedine into (−)-narwedine in the presence of galanthamine. In still further embodiments, said resolving is in the presence of 1% (+)-galanthamine. In still further embodiments, further comprising resolving said (±) narwedine into (−)-narwedine in the presence of galanthamine with a reducing agent. While it is not intended that the present invention be limited by the nature of the reducing agent, in a preferred embodiment, said reducing agent is L-Selectride. Reduction of (−)-narwedine with L-Selectride provides (−)-galanthamine (99%).

As noted above, the methods permit the further efficient synthesis of galanthamine derivatives, such as N-alkyl galanthamine derivatives [e.g. N-allylnorgalanthamine, N-(14-methylallyl)norgalanthamine, some specific non-limiting examples of contemplated derivatives are shown in the structures in FIG. 10], which are more potent cholinesterase inhibitors than galanthamine. In this regard, the above-described steps can be modified to create these derivatives. Moreover, the present invention contemplates treating and/or preventing disease with galanthamine (and derivatives thereof) synthesized according to the above scheme and formulated as pharmaceutical formulations.

BRIEF DESCRIPTION OF THE DRAWINGS

For a more complete understanding of the features and advantages of the present invention, reference is now made to the detailed description of the invention along with the accompanying figures.

FIG. 4A provides the general overall scheme, while FIG. 4B provides specific (non-limiting) examples.

FIG. 5A provides the general overall scheme, while FIG. 5B provides specific (non-limiting) examples.

FIG. 7A provides the general overall scheme, while FIG. 7B provides specific (non-limiting) examples. Compounds 2, 14, 24, 25 and 26 are racemates, but the structures are drawn in FIG. 7B (for clarity) as a single enantiomer with their configuration corresponding to that of (−)-galanthamine. FIG. 7C provides an alternative synthetic route for the production of narwedine and galanthamine. Compounds 2, 14, 24, and 27 are racemates, but the structures are drawn in FIG. 7C (for clarity) as a single enantiomer with their configuration corresponding to that of (−)-galanthamine.

FIG. 8A provides the general overall scheme, while FIG. 8B provides specific (non-limiting) examples.

FIG. 9A provides the general overall scheme, while FIG. 9B provides specific (non-limiting) examples.

DEFINITIONS

Figure 1:
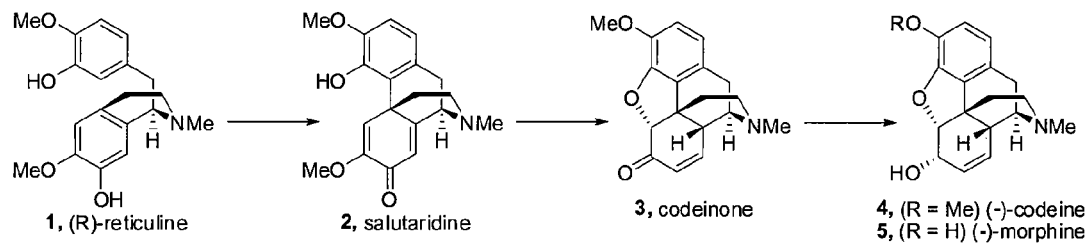
FIG. 1 shows a biosynthetic pathway for the synthesis of morphine and codeine.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "cross-conjugated" refers to a compound where in there are (at least) two double bonds that are conjugated to a "central" double bond in such a way that the π electronic system forms a bifurcation.

As used herein, "morphine" refers to a compound represented by the following chemical structure:

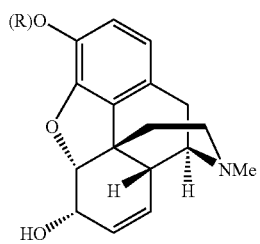

where R is H. It is not intended that the invention be limited to any particular derivative, analog or isomer of morphine or salt thereof. Examples of derivatives of morphine include but are in no way limited to morphine, morphine acetate, morphine citrate, morphine bitartrate, morphine stearate, morphine phthalate, morphine hydrobromide, morphine hydrobromide.$2H_2O$, morphine hydrochloride, morphine hydrochloride.$3H_2O$, morphine hydriodide.$2H_2O$, morphine lactate, morphine monohydrate, morphine meconate.$5H_2O$, morphine mucate, morphine nitrate, morphine phosphate.$0.5H_2O$, morphine phosphate.$7H_2O$, morphine salicylate, morphine phenylpropionate, morphine methyliodide, morphine isobutyrate, morphine hypophosphite, morphine sulfate.$5H_2O$, morphine tannate, morphine tartrate.$3H_2O$, morphine valerate, morphine methylbromide, morphine methylsulfonate, morphine-N-oxide, morphine-N-oxide quinate, dihydromorphine and pseudomorphine. It is not intended that the present invention be limited by the type of chemical substituent or substituents that is or are coordinated to morphine. Examples of chemical substituents include but are in no way limited to hydrogen, methyl, ethyl, formyl, acetyl, phenyl, chloride, bromide, hydroxyl, methoxyl, ethoxyl, methylthiol, ethylthiol, propionyl, carboxyl, methoxy carbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarboxy, N-morpholinylcarbonyl, 2-(dimethylamino)ethylcarbamyl, 1-piperidinylcarbonyl, methylsulfonyl, ethylsulfonyl, phenylsulfonyl, 2-piperidinylethyl, 2-morpholinylethyl, 2-(dimethylamino)ethyl, 2-(diethyl amino) ethyl, butylthiol, dimethylamino, diethylamino, piperidinyl, pyrrolidinyl, imidazolyl, pyrazolyl, N-methylpiperazinyl and 2-(dimethylamino)ethylamino.

As used herein, "codeine" refers to a compound represented by the following chemical structure:

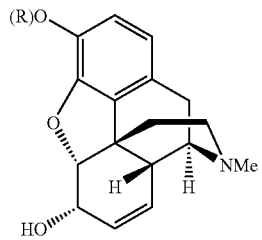

where R is $CH_3$, also referred to as a methyl (Me) substituent. It is not intended that the invention be limited to any particular derivative, analog or isomer of codeine or salt thereof. Examples of derivatives of codeine include but are in no way limited to codeine, codeine acetate, codeine citrate, codeine bitartrate, codeine stearate, codeine phthalate, codeine hydrobromide, codeine hydrobromide.$2H_2O$, codeine hydrochloride, codeine hydrochloride.$3H_2O$, codeine hydriodide.$2H_2O$, codeine lactate, codeine monohydrate, codeine meconate.$5H_2O$, codeine mucate, codeine nitrate, codeine phosphate.$0.5H_2O$, codeine phosphate.$7H_2O$, codeine salicylate, codeine phenylpropionate, codeine methyliodide, codeine isobutyrate, codeine hypophosphite, codeine sulfate.$5H_2O$, codeine tannate, codeine tartrate.$3H_2O$, codeine valerate, codeine methylbromide, codeine methylsulfonate, codeine-N-oxide, codeine-N-oxide quinate and pseudocodeine. It is not intended that the present invention be limited by the type of chemical substituent or substituents that is or are coordinated to codeine. Examples of chemical substituents include but are in no way limited to hydrogen, methyl, ethyl, formyl, acetyl, phenyl, chloride, bromide, hydroxyl, methoxyl, ethoxyl, methylthiol, ethylthiol, propionyl, carboxyl, methoxy carbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarboxy, N-morpholinylcarbonyl, 2-(dimethylamino)ethylcarbamyl, 1-piperidinylcarbonyl, methylsulfonyl, ethylsulfonyl, phenylsulfonyl, 2-piperidinylethyl, 2-morpholinylethyl, 2-(dimethylamino)ethyl, 2-(diethylamino)ethyl, butylthiol, dimethylamino, diethylamino, piperidinyl, pyrrolidinyl, imidazolyl, pyrazolyl, N-methylpiperazinyl and 2-(dimethylamino)ethylamino.

As used herein, "galanthamine" refers to a compound represented by the following chemical structure:

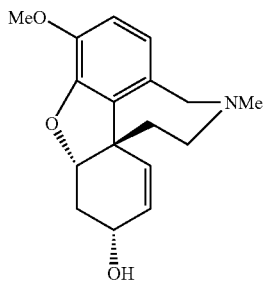

It is not intended that the invention be limited to any particular derivative, analog or isomer of galanthamine or salt thereof. Examples of derivatives of galanthamine include but are in no way limited to galanthamine, galanthamine acetate, galanthamine citrate, galanthamine bitartrate, galanthamine stearate, galanthamine phthalate, galanthamine hydrobromide, galanthamine hydrobromide.2H$_2$O, galanthamine hydrochloride, galanthamine hydrochloride.3H$_2$O, galanthamine hydriodide.2H$_2$O, galanthamine lactate, galanthamine monohydrate, galanthamine meconate.5H$_2$O, galanthamine mucate, galanthamine nitrate, galanthamine phosphate.0.5H$_2$O, galanthamine phosphate.7H$_2$O, galanthamine salicylate, galanthamine phenylpropionate, galanthamine methyliodide, galanthamine isobutyrate, galanthamine hypophosphite, galanthamine sulfate.5H$_2$O, galanthamine tannate, galanthamine tartrate.3H$_2$O, galanthamine valerate, galanthamine methylbromide, galanthamine methylsulfonate, galanthamine-N-oxide, galanthamine-N-oxide quinate and pseudogalanthamine. It is not intended that the present invention be limited by the type of chemical substituent or substituents that is or are coordinated to galanthamine. Examples of chemical substituents include but are in no way limited to hydrogen, methyl, ethyl, formyl, acetyl, phenyl, chloride, bromide, hydroxyl, methoxyl, ethoxyl, methylthiol, ethylthiol, propionyl, carboxyl, methoxy carbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarboxy, N-morpholinylcarbonyl, 2-(dimethylamino)ethylcarbamyl, 1-piperidinylcarbonyl, methylsulfonyl, ethylsulfonyl, phenylsulfonyl, 2-piperidinylethyl, 2-morpholinylethyl, 2-(dimethylamino)ethyl, 2-(diethylamino)ethyl, butylthiol, dimethylamino, diethylamino, piperidinyl, pyrrolidinyl, imidazolyl, pyrazolyl, N-methylpiperazinyl and 2-(dimethylamino)ethylamino.

As used herein, "narwedine" refers to a compound represented by the following chemical structure:

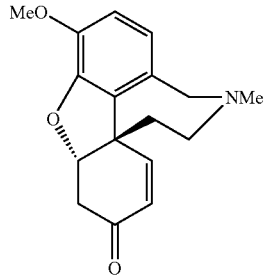

It is not intended that the invention be limited to any particular derivative, analog or isomer of narwedine or salt thereof. Examples of derivatives of narwedine include but are in no way limited to narwedine, narwedine acetate, narwedine citrate, narwedine bitartrate, narwedine stearate, narwedine phthalate, narwedine hydrobromide, narwedine hydrobromide.2H$_2$O, narwedine hydrochloride, narwedine hydrochloride.3H$_2$O, narwedine hydriodide.2H$_2$O, narwedine lactate, narwedine monohydrate, narwedine meconate.5H$_2$O, narwedine mucate, narwedine nitrate, narwedine phosphate.0.5H$_2$O, narwedine phosphate.7H$_2$O, narwedine salicylate, narwedine phenylpropionate, narwedine methyliodide, narwedine isobutyrate, narwedine hypophosphite, narwedine sulfate.5H$_2$O, narwedine tannate, narwedine tartrate.3H$_2$O, narwedine valerate, narwedine methylbromide, narwedine methylsulfonate, narwedine-N-oxide, narwedine-N-oxide quinate and pseudonarwedine. It is not intended that the present invention be limited by the type of chemical substituent or substituents that is or are coordinated to narwedine. Examples of chemical substituents include but are in no way limited to hydrogen, methyl, ethyl, formyl, acetyl, phenyl, chloride, bromide, hydroxyl, methoxyl, ethoxyl, methylthiol, ethylthiol, propionyl, carboxyl, methoxy carbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N-piperazinylcarbonyl, 2-(dimethylamino)ethylcarboxy, N-morpholinylcarbonyl, 2-(dimethylamino)ethylcarbamyl, 1-piperidinylcarbonyl, methylsulfonyl, ethylsulfonyl, phenylsulfonyl, 2-piperidinylethyl, 2-morpholinylethyl, 2-(dimethylamino)ethyl, 2-(diethylamino)ethyl, butylthiol, dimethylamino, diethylamino, piperidinyl, pyrrolidinyl, imidazolyl, pyrazolyl, N-methylpiperazinyl and 2-(dimethylamino)ethylamino.

A "Suzuki reaction" refers to a chemical reaction between an aryl- or vinyl-boronic acid with an aryl- or vinyl halide that is catalyzed via a palladium complex as provided for in U.S. Pat. No. 6,136,157 to Lindeberg et al., incorporated herein by reference. While not limiting the scope of the present invention, the reaction is used to synthesize poly-olefins, styrenes, substituted biphenyl complexes and incorporate alkyl halides including but in no way limited to alkyl bromides.

A "Henry aldol" reaction, also referred to as a "nitroaldol" reaction, is a reaction carried out between an aldehyde and nitromethane as provided for in U.S. Pat. No. 7,312,191 to Rose et al., incorporated herein by reference. The reaction results in the synthesis of a β-hydroxy nitrosylated compound, also referred to as a nitroethylene compound.

A "Grignard reagent" refers to chemical reagents which are prepared by the reaction of magnesium metal with an organic halide. Gignard reagents refer to any of a class of reagents with the general formula RMgX, in which R is an organic radical, including but not limited to where R is an alkyl or aryl, and X is a halogen. Grignard reagents are used as a source of nucleophillic carbon. It is known that the preparation of Grignard reagents are often quite difficult. Formation of these reagents is inhibited by the presence of water and alcohols, ethers and halides and by impurities on the surface of the magnesium turnings. While not limiting the scope of the present invention, the reagent is commonly used but not limited to reacting with acyl, epoxide, alcohols, heterocyclic, carboyxllic acids, esters, ethers, and other electrophillic atoms.

As used herein, "alkaloid" refers to a member of the class of naturally occurring chemical compounds containing basic nitrogen atoms. Alkaloids are produced by a large variety of organisms, with many exhibiting pharmacological effects. While not limiting the scope of the present invention, alkaloids are often formulated as salts to enhance their solubility under physiological conditions. Examples of alkaloid salt counter ions include the appropriate counter ion derived from but in no way limited to mineral acids such as hydrochloric acid and sulfuric acid as well as organic acid counter ions including but not limited to tartaric acid and maleic acid.

"Epimers" refer to diastereomers that differ in configuration of only one stereogenic center. Diastereomers are a class of stereoisomers that are non-superposable, non-mirror images of one another, unlike enantiomers that are non-superposable mirror images of one another.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid.

As used herein, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylamino); "cyano" means —CN; "azido" means —N$_3$; "mercapto" means —SH; "thio" means =S; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "silyl" means —SiH$_3$ (see below for definitions of group(s) containing the term silyl, e.g., alkylsilyl).

For the groups below, the following parenthetical subscripts further define the groups as follows: "(Cn)" defines the exact number (n) of carbon atoms in the group; "(C≦n)" defines the maximum number (n) of carbon atoms that can be in the group; (Cn-n) defines both the minimum (n) and maximum number (n') of carbon atoms in the group. For example, "alkoxy$_{(C \leq 10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$—CH$_2$CH$_2$O(C)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

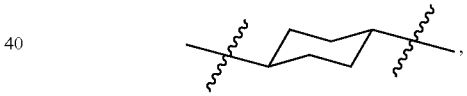

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$F, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O) CH$_3$, —C$_6$H$_4$CH$_2$NH$_2$, —C$_6$H$_4$CF$_3$, —C$_6$H$_4$CN, —C$_6$H$_4$CHO, C$_6$H$_4$CHO, C$_6$H$_4$C(O) CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON (CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

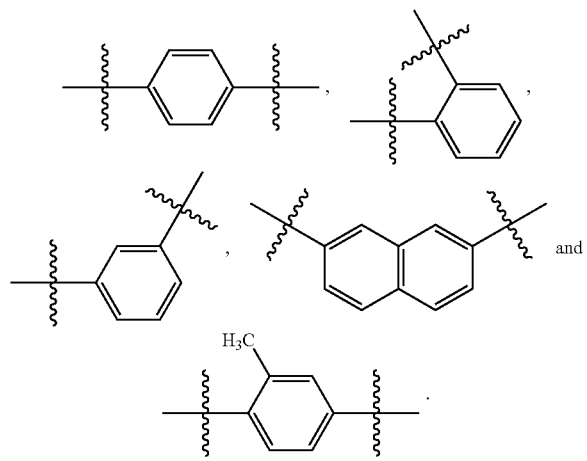

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

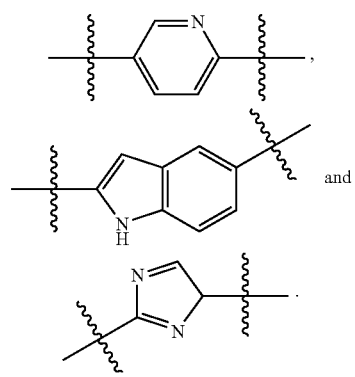

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)₂R, in which R is a substituted alkyl, as that term is defined above. For example, —S(O)₂CH₂CF₃ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)₂R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)₂R, in which R is substituted alkenyl, alkynyl, aryl, aralkyl, heteroaryl and heteroaralkyl, respectively.

The term "alkylammonium" when used without the "substituted" modifier refers to a group, defined as —NH₂R⁺, —NHRR'⁺, or —NRR'R"⁺, in which R, R' and R" are the same or different alkyl groups, or any combination of two of R, R' and R" can be taken together to represent an alkanediyl. Non-limiting examples of alkylammonium cation groups include: —NH₂(CH₃)⁺, —NH₂(CH₂CH₃)⁺, —NH₂(CH₂CH₂CH₃)⁺, —NH(CH₃)₂⁺, —NH(CH₂CH₃)₂⁺, —NH(CH₂CH₂CH₃)₂⁺, —N(CH₃)₃⁺, —N(CH₃)(CH₂CH₃)₂⁺, —N(CH₃)₂(CH₂CH₃)⁺, —NH₂C(CH₃)₃⁺, —NH(cyclopentyl)₂⁺, and —NH₂(cyclohexyl)⁺. The term "substituted alkylammonium" refers —NH₂R⁺, —NHRR'⁺, or —NRR'R"⁺, in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more carbon atoms, at least two of which are attached to the nitrogen atom shown in the formula. The term "alkylsulfonium" when used without the "substituted" modifier refers to the group —SRR'⁺, in which R and R' can be the same or different alkyl groups, or R and R' can be taken together to represent an alkanediyl. Non-limiting examples of alkylsulfonium groups include: —SH(CH₃)⁺, —SH(CH₂CH₃)⁺, —SH(CH₂CH₂CH₃)⁺, —S(CH₃)₂⁺, —S(CH₂CH₃)₂⁺, —S(CH₂CH₂CH₃)₂⁺, —SH(cyclopentyl)⁺, and —SH(cyclohexyl)⁺. The term "substituted alkylsulfonium" refers to the group —SRR'⁺, in which R and R' can be the same or different substituted alkyl groups, one of R' or R' is an alkyl and the other is a substituted alkyl, or R and R' can be taken together to represent a substituted alkanediyl. For example, —SH(CH₂CF₃)⁺ is a substituted alkylsulfonium group.

The term "alkylsilyl" when used without the "substituted" modifier refers to a monovalent group, defined as —SiH₂R, —SiHRR', or —SiRR'R", in which R, R' and R" can be the same or different alkyl groups, or any combination of two of R, R' and R" can be taken together to represent an alkanediyl. The groups, —SiH₂CH₃, —SiH(CH₃)₂, —Si(CH₃)₃ and —Si(CH₃)₂C(CH₃)₃, are non-limiting examples of unsubstituted alkylsilyl groups. The term "substituted alkylsilyl" refers —SiH₂R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include ¹³C and ¹⁴C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

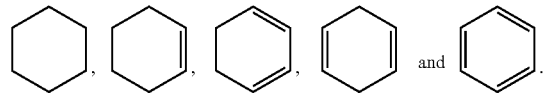

As will be understood by a person of skill in the art, no one such ring atom forms part of more than one double bond.

Any undefined valency on an atom of a structure shown in this application implicitly represents a hydrogen atom bonded to the atom.

A ring structure shown with an unconnected "R" group, indicates that any implicit hydrogen atom on that ring can be replaced with that R group. In the case of a divalent R group (e.g., oxo, imino, thio, alkylidene, etc.), any pair of implicit hydrogen atoms attached to one atom of that ring can be replaced by that R group. This concept is as exemplified below:

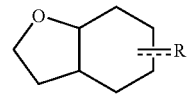

represents

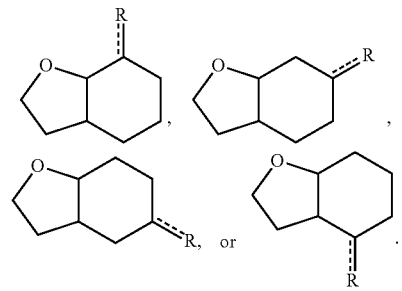

As used herein, a "chiral auxiliary" refers to a removable chiral group that is capable of influencing the stereoselectivity of a reaction. Persons of skill in the art are familiar with such compounds, and many are commercially available.

The term "protecting group," as that term is used in the specification and/or claims, is used in the conventional chemical sense as a group, which reversibly renders unreactive a functional group under certain conditions of a desired reaction and is understood not to be H. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

Protecting groups include but are not limited to: Alcohol protecting groups: Acetoxy group, β-Methoxyethoxymethyl ether (MEM), methoxymethyl ether (MOM), p-methoxybenzyl ether (PMB), methylthiomethyl ether, pivaloyl (Piv), tetrahydropyran (THP), silyl ethers (including but not limited to trimethylsilyl (TMS), tert-butyldimethylsilyl (TBDMS), and triisopropylsilyl (TIPS) ethers), methyl ethers, and ethoxyethyl ethers (EE). Amine protecting groups: carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, benzyl (Bn) group, p-methoxybenzyl (PMB), dimethoxybenzyl (DMPM), p-methoxyphenyl (PMP) group, tosyl (Ts) group, and other sulfonamides (Nosyl & Nps) groups. Carbonyl protecting groups: acetals, ketals, acylals, and dithianes. Carboxylic acid protecting groups: alkyl esters, aryl esters, silyl esters. Protection of terminal alkynes protected as propargyl alcohols in the Favorskii reaction.

The term "leaving group," as that term is used in the specification and/or claims, is an atom or group (charged or uncharged) that becomes detached from an atom in what is considered to be the residual or main part of the substrate in a specified reaction.

Leaving groups include, but are not limited to: $NH_2^-$ (amine), $CH_3O^-$ (methoxy), $HO^-$ (hydroxyl), $CH_3COO^-$ (carboxylate), $H_2O$ (water), $F^-$, $Cl^-$, $Br^-$, $I^-$, $N_3^-$ (azide), $SCN^-$ (thiocyanate), $NO_2$ (nitro), and protecting groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (P. H. Stahl & C. G. Wermuth eds., Verlag Helvetica Chimica Acta, 2002), As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

Enantiomers are compounds that individually have properties said to have "optical activity" and consist of chiral molecules. If a chiral molecule is dextrorotary, its enantiomer will be levorotary, and vice-versa. In fact, the enantiomers will rotate polarized light the same number of degrees, but in opposite directions. "Dextrorotation" and "levorotation" (also spelled laevorotation) refer, respectively, to the properties of rotating plane polarized light clockwise (for dextrorotation) or counterclockwise (for levorotation). A compound with dextrorotation is called "dextrorotary," while a compound with levorotation is called "levorotary".

A standard measure of the degree to which a compound is dextrorotary or levorotary is the quantity called the "specific rotation" "[α]". Dextrorotary compounds have a positive specific rotation, while levorotary compounds have negative. Two enantiomers have equal and opposite specific rotations. A dextrorotary compound is prefixed "(+)-" or "d-". Likewise, a levorotary compound is often prefixed "(−)-" or "l-". These "d-" and "l-" prefixes should not be confused with the "D-" and "L-" prefixes based on the actual configuration of each enantiomer, with the version synthesized from naturally occurring (+)-compound being considered the D-form. A mixture of enantiomers of the compounds is prefixed "(±)-". An equal mixture of enantiomers of the compounds is considered "optically inactive".

When used herein, unless otherwise specified, "morphine" refers to a mixture of enantiomers of morphine, "(±)-morphine." When used herein, unless otherwise specified, galanthamine refers to a mixture of enantiomers of galanthamine, "(±) galanthamine," or a single enantiomer, e.g. "(−)-galanthamine."

Figure 7A:
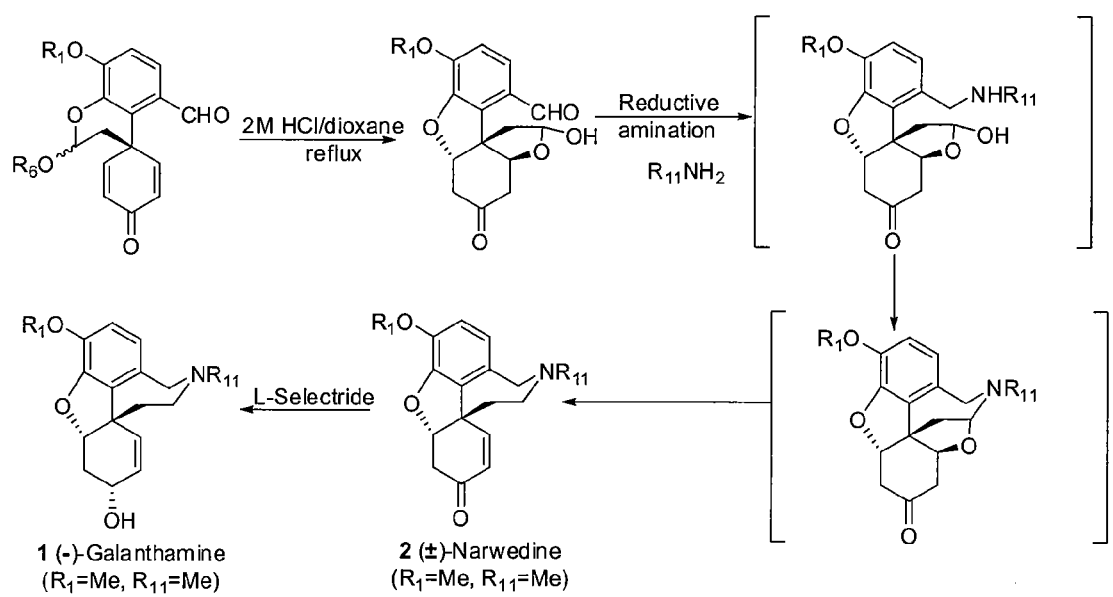
FIGS. 7A and B show embodiments of the present invention whereby a cross-conjugated compound is modified in a series of steps so as to synthesis narwedine and galanthamine.

Compounds 2, 14, 24, 25 and 26 are racemates, but the structures are drawn in FIGS. 7A & B (for clarity) as a single enantiomer with their configuration corresponding to that of (−)-galanthamine.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl ($-C(O)OC(CH_3)_3$), benzyloxycarbonyl, p-methoxybenzyloxycarbonyl, vinyloxycarbonyl, β-(p-toluenesulfonyl)ethoxycarbonyl, and the like.

The present invention contemplates the above-described compositions in "therapeutically effective amounts" or "pharmaceutically effective amounts", which means that amount which, when administered to a subject or patient for treating a disease, is sufficient to effect such treatment for the disease or to emeliorate one or more symptoms of a disease or condition (e.g. emeliorate pain).

The above definitions supersede any conflicting definition in any of the reference that is incorporated by reference herein.

The present invention contemplates, in certain embodiments inhibiting or preventing disease (e.g. treating early Alzheimer's with galanthamine). As used herein, the terms "prevent" and "preventing" include the prevention of the recurrence, spread or onset of a disease or disorder. It is not intended that the present invention be limited to complete prevention. In some embodiments, the onset is delayed, or the severity of the disease or disorder is reduced. Studies with galanthamine have showed mild cognitive and global benefits for patients with Alzheimer's disease.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any mammal, preferably a human patient, livestock, or domestic pet.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

DETAILED DESCRIPTION OF THE INVENTION

The present invention relates to methods for the synthesis of morphine and derivatives thereof. In preferred embodiments, the invention relates to methods for improving the efficiency and overall yield of said morphine and derivatives. It is not intended that the present invention be limited to any particular chemical, biochemical or biological mechanism or theory.

In preferred embodiments, the invention relates to methods and compositions comprising morphine and derivatives thereof. Morphine ((5a,6a)-7,8-didehydro-4,5-epoxy-17-methylmorphinan-3,6-diol; $C_{17}H_{19}NO_3$; MW=285.4), a member of the alkaloid class of compounds, is a highly effective analgesic used in a myriad of pharmaceutical and biomedical applications. While there are numerous reported synthetic strategies for obtaining limited quantities and percent yields of morphine alkaloids such as Zezula et al. (2007) *Synlett*, 2863-2867; Omori et al. (2007) *Synlett*, 2859-2862; Uchida et al. (2006) *Org. Lett.* 8, 5311-5313 and Trost et al. (2005) *J. Am. Chem. Soc.* 127, 14785-14803, all of which are hereby incorporated by reference, one of the most practical synthetic strategies for obtaining opium alkaloids is the Rice adaptation of the Grewe strategy as provided for in Rice (1980) *J. Org. Chem.* 45, 3135-3137, hereby incorporated by reference. While not limiting the scope of the current invention, the biosynthetic steps utilized by nature for the generation of morphine alkaloids is well understood. As provided for in FIG. 1, (R)-reticuline (1) is converted into salutaridine (2) through an enzymatically mediated ortho-para phenolic oxidation as provided for in Barton et al. (1965) *Journal of the Chemical Society*, 2423-2438, incorporated herein by reference. Salutaridine (2) is subsequently transformed in vivo into codienone 3 (via thebaine), which is reduced to codeine (4) and demethylated to give morphine (5).

The efficient phenolic oxidative pathway undertaken in plants to the most effective analgesics in all of medicinal practice underscores the need to deduce the enzymatically-controlled pathway to these agents. However, attempts to mimic such aesthetic chemistry in the laboratory for the practical production of these important compounds in an efficient and economical manner, has not resulted in practical yields of (2) or related derivatives.

Figure 2:
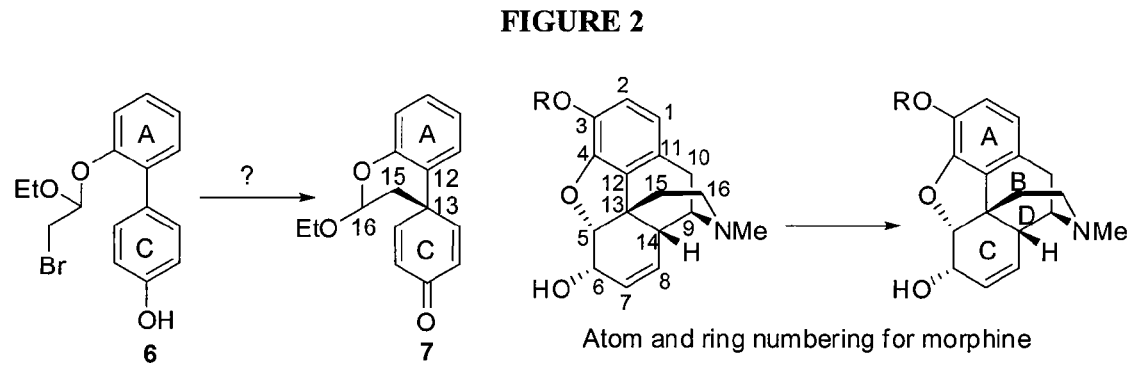
FIG. 2 shows embodiments of the present invention, as well as the atomic numbering scheme for morphine.

While not limiting the scope of the present invention to any particular theory, one of the central issues in morphine and morphine derivative synthesis is the construction of the cross-conjugated 2,5-cyclohexadienone chromophore imbedded within salutaridine (2) in an effective practical manner. Clearly, the published methods have been overwhelmingly influenced by the Barton phenolic oxidative biogenetic dogma as provided for in *Studies in Natural Products Chemistry*, Rahman, A, editor. Volume 18, Stereoselective Synthesis (Part K): *A Historical Perspective of Morphine Syntheses*, Hudlicky, T.; Butora, G.; Fearnley, S. P.; Gum, A. G.; Stabile, M. R. 1996, 43-154. Elsevier Publishers, New York; *The Alkaloids*, Cordell, G. A. and Brossi, A., editors. Volume 45, Chapter 2. "The Morphine Alkaloids," Szántay, C.; Dörnyei, G.; Blaskó, G. 1994, 128-222. Academic Press, New York and Barton, D. H. R.; Kirby, G. W.; Steglich, W.; Thomas, G. M.; Battersby, A. R.; Dobson, T. A. and Ramuz, H. (1965) *Journal of the Chemical Society*, 2423-2438, all of which are hereby incorporated by reference. While phenolic oxidation provides a structurally simplifying and unifying explanation of a large number of natural product structures, it has, at an experimental level, invariably resulted in low yields when applied to the in vitro conversion of phenols into cross-conjugated 2,5-cyclohexadienones. While intramolecular C-alkylation of phenols to form 2,5-cyclohexadienones has been employed, and the applications of this non-oxidative methodology to the synthesis of a wide range of both natural and unnatural products, this type of reaction has not been used for the synthesis of morphinans. It is known that intramolecular alkylation of phenolate anions can result in O-alkylation (remains aromatic), versus C-alkylation of the phenolate anion that results in either 2,4- or 2,5-conjugated cyclohexadienones. While not limiting the present invention to any particular theory or mechanism, applying the intramolecular phenol alkylation reaction (FIG. 2) to the synthesis of a suitably substituted cross-conjugated 2,5-cyclohexadienone would require, in its simplest form, the conversion of (6) into (7). The acetal ($C_{1-6}$ carbon atom) in (7) will eventually evolve into the D-ring of morphine by a reductive amination reaction.

In preferred embodiments, the invention relates to improved methods for the synthesis of galanthamine and intermediates thereof. Galanthamine ((4aS,6R,8aS)-5,6,9,10,11,12-hexahydro-3-methoxy-11-methyl-4aH-[1]benzofuro[3a,3,2-ef]-[2]-benzazepin-6-ol; $C_{17}H_{21}NO_3$; MW=287), an amaryllidaceae alkaloid, has found extensive use in the early treatment of Alzheimer's disease. The compound may be isolated via synthesis or from plants such as the Caucasian snowdrop (Voronov's snowdrop), *Lycoris radiata* (red spider lily) and *Galanthus woronowii* (Amaryllidaceae) and related species. While not limiting the present invention to any particular theory, it is believed that the compound is metabolized primarily through the liver. The extraction of galanthamine from the bulbs of the aforementioned species does not supply sufficient material for the on-going clinical evaluation and treatment of early Alzheimer's patients. Commercially available supplies of galanthamine are obtained via a laborious nine-step synthetic scheme that results in an overall yield of only 12.4% as provided for in Küenburg et al. (1999) *Organic Process Research and Development* 3, 425-431, incorporated herein by reference. These difficulties in obtaining sufficient supplies of galanthamine underscore the need for more efficient synthetic strategies for obtaining the compound.

Pharmaceutical Formulations

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155, hereby incorporated by reference).

In a preferred embodiment, the active compound and optionally another therapeutic or prophylactic agent are formulated in accordance with routine procedures as pharmaceutical compositions adapted for intravenous administration to human beings. Typically, the active compounds for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long acting, by dissolving or suspending the compound in oily or emulsified vehicles, which allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In some embodiments, the administration is optical (e.g. eyes drops applied directly to the eye). In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference (62$^{nd}$ ed. 2008, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery or topical application, e.g., in conjunction with a wound dressing after surgery, by injection, by means of a catheter, by means of a suppository, or by means of an implant, said implant being in one embodiment of a porous, non-porous, or gelatinous material, including membranes, such as silastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

Selection of a particular effective dose can be determined (e.g., via clinical trials) by a skilled artisan based upon the consideration of several factors, which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); µl (milliliters); (microliters); cm (centimeters); mm (millimeters); µm (micrometers); nm (nanometers); C (degrees Centigrade); TLC (thin layer chromatography).

Example I

Figure 3A:
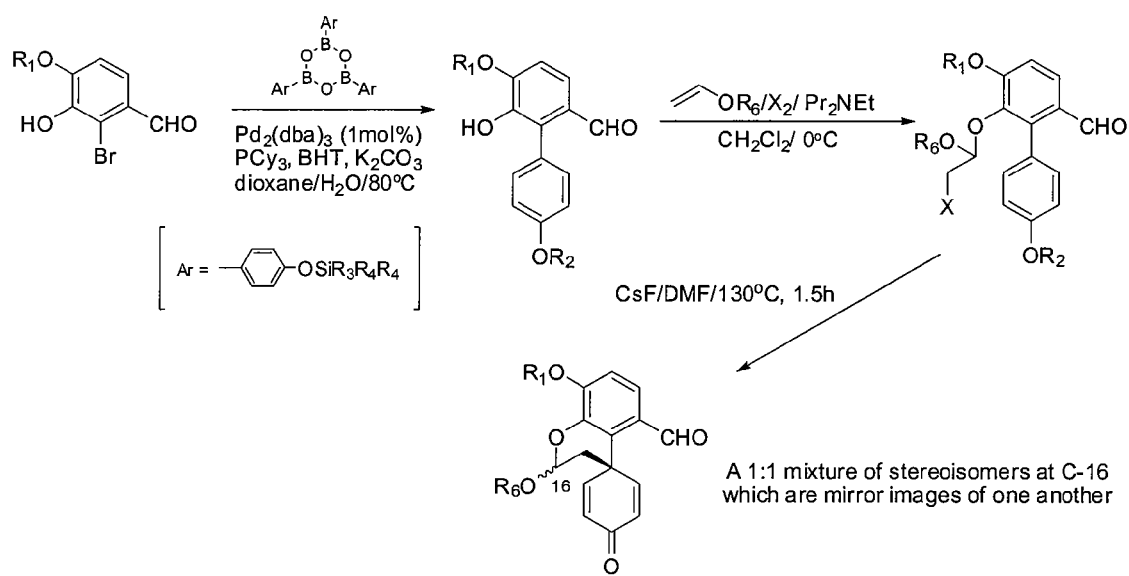
FIG. 3A provides the general overall scheme, while FIG. 3B provides specific (non-limiting) examples.
Figure 3B:
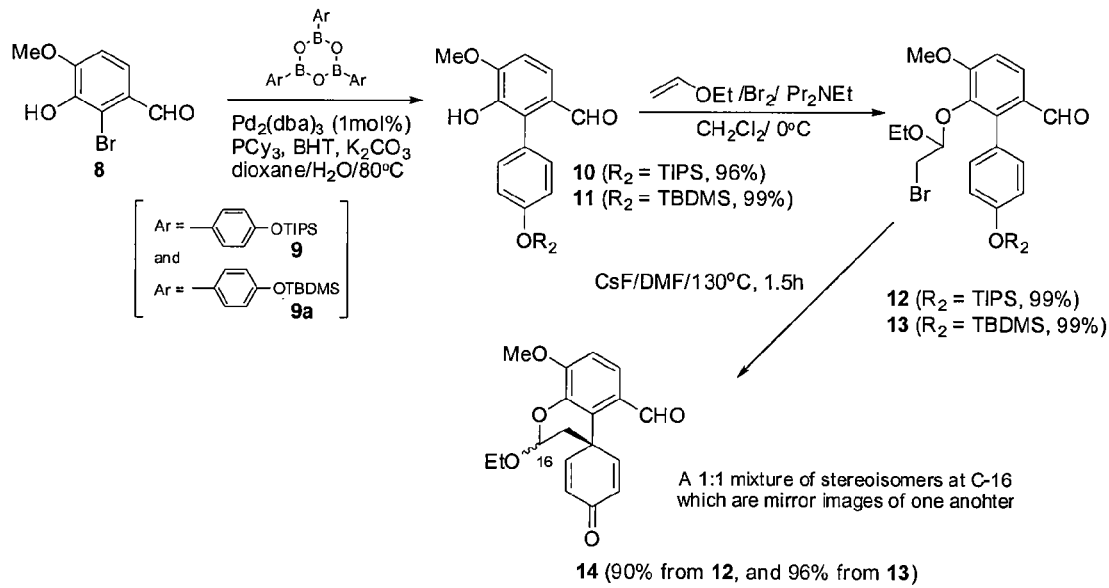
FIGS. 3 A and B show embodiments of the present invention for synthesizing a cross-conjugated compound useful in the synthesis of both morphine and galanthamine (as well as derivatives of both).

As shown in FIG. 3B (the specific route from 8 to 14), commercially available 8 was coupled to the boronic acid tris anhydride 9 using Suzuki reaction conditions to give 10 in 96% yield. Treatment of 10 with ethylvinyl ether/Br2/diisopropylamine/CH$_2$Cl$_2$ at 0° C. resulted in the ether 12 in 99% yield. 12 was then combined with CsF (3.22 eq) in dimethylformamide under reflux conditions (130° C.) to give 14 in 90% yield. The structure of 14 was determined via X-ray analysis. The overall yield from 8 to 14 via 10 and 12 is 85.5% for the three steps. In an alternative embodiment, the same sequence of reactions may be performed with the SiMe$_2$But (tert-butyldimethylsilyl) protected phenol derivative 9a, which provides the cross-conjugated 2,5-cyclohexadienone 14 in three steps from 8 via 11 and 13 in an overall yield of 94.1%.

Figure 4A:
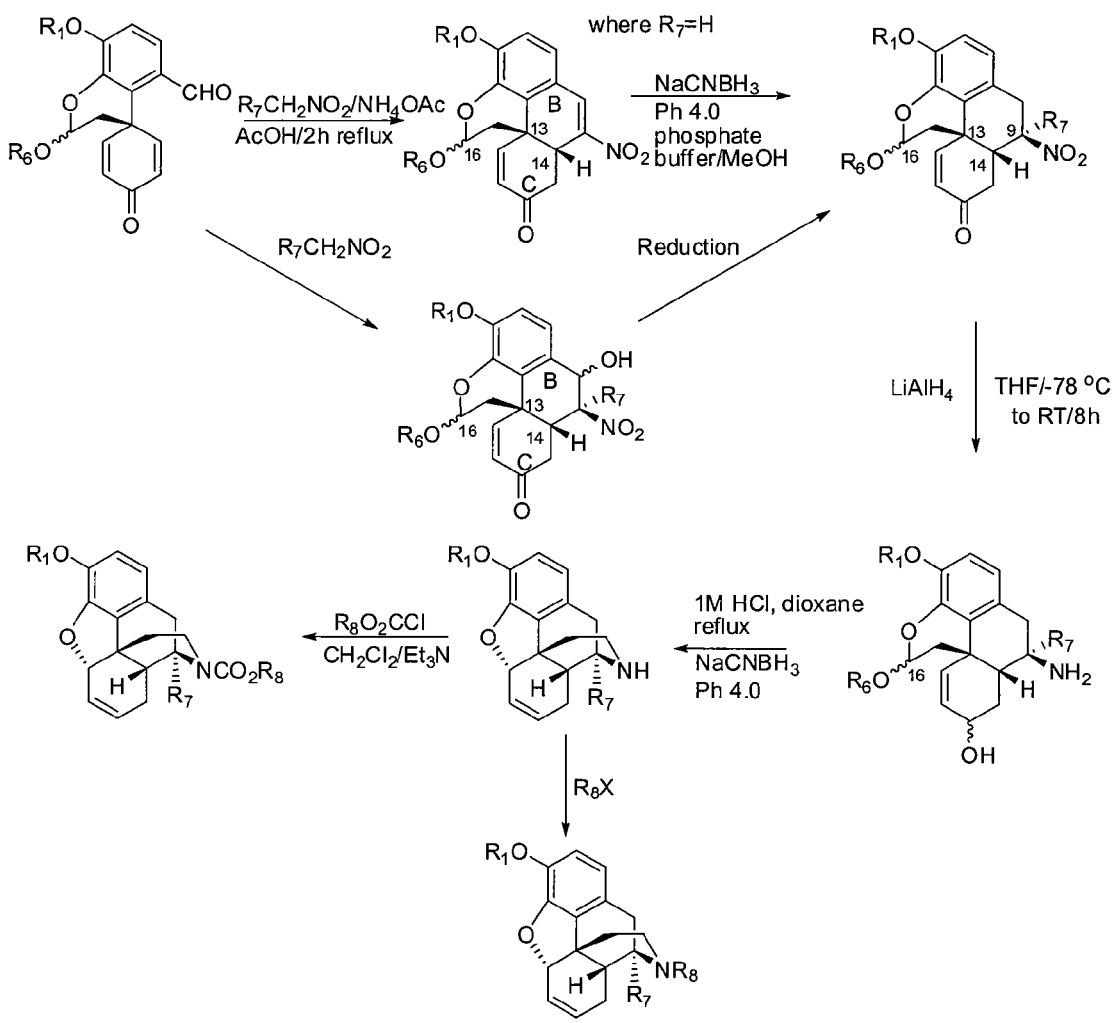
FIGS. 4A and B show embodiments of the present invention whereby a cross-conjugated compound is modified in a series of steps (and alternative pathways) to create a carbamate and tertiary amine derivatives useful for the synthesis of morphine and derivatives thereof.
Figure 4B:
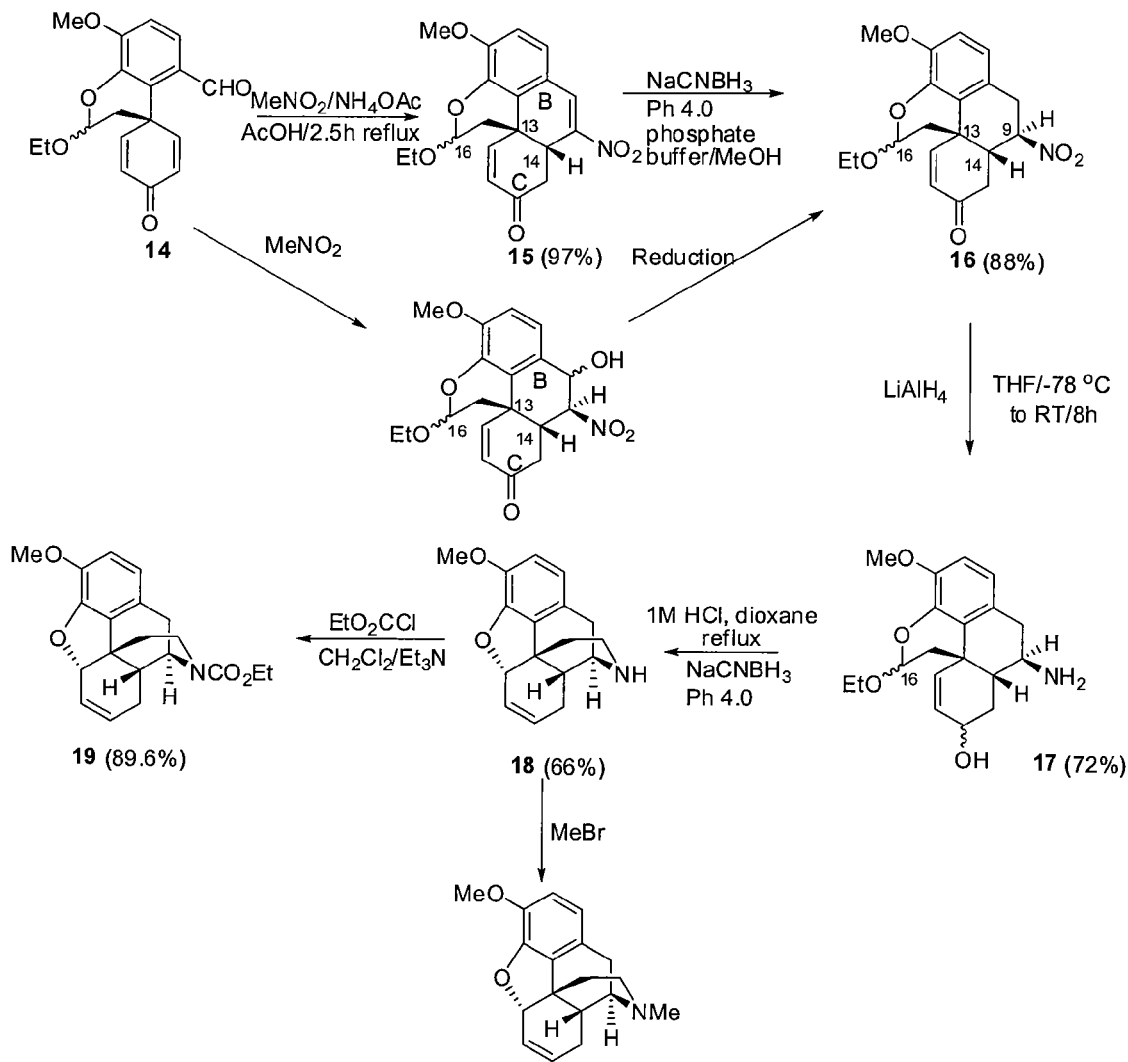

As shown in FIG. 4B (the specific route from 14 to 19), Treatment of 14 with nitromethane under Henry aldol reaction conditions results in 15 at an unoptimized yield of 97% as a mixture (1:1) of epimers at the $C_{16}$ site. These epimers were characterized by X-ray crystallography. It is noteworthy that only the correct cis-stereochemical relationship between the newly formed B-ring and the C-ring, i.e. at the $C_{13}$ and $C_{14}$ positions, is observed in 15.

The stereogenic center at $C_{16}$ in 15, 16 and 17 is eventually removed by the conversion of 17 into 18, as shown in FIG. 4B. Treatment of 15 with sodium cyanoborohydride gave 16 in 90% yield, which on further reduction with lithium aluminum hydride gave 17 (72% yield). The intramolecular reductive amination of 17 gave 18. The yields in these conversions are not optimized, but are clean reactions with no discernible by-products. The compound 18 was characterized as the known carbamate derivative 19 from the Taber synthesis of morphine.

Figure 5A:
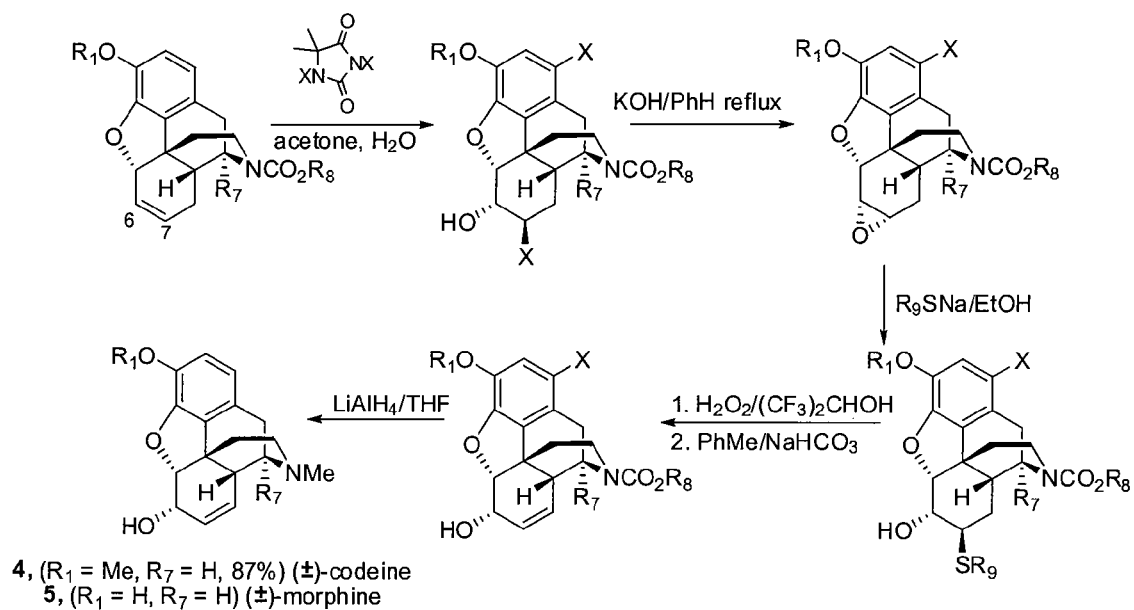
FIGS. 5A and B show embodiments of the present invention whereby a carbamate derivative is modified in a series of steps to generate morphine, derivatives thereof, and related compounds (e.g. codeine).
Figure 5B:
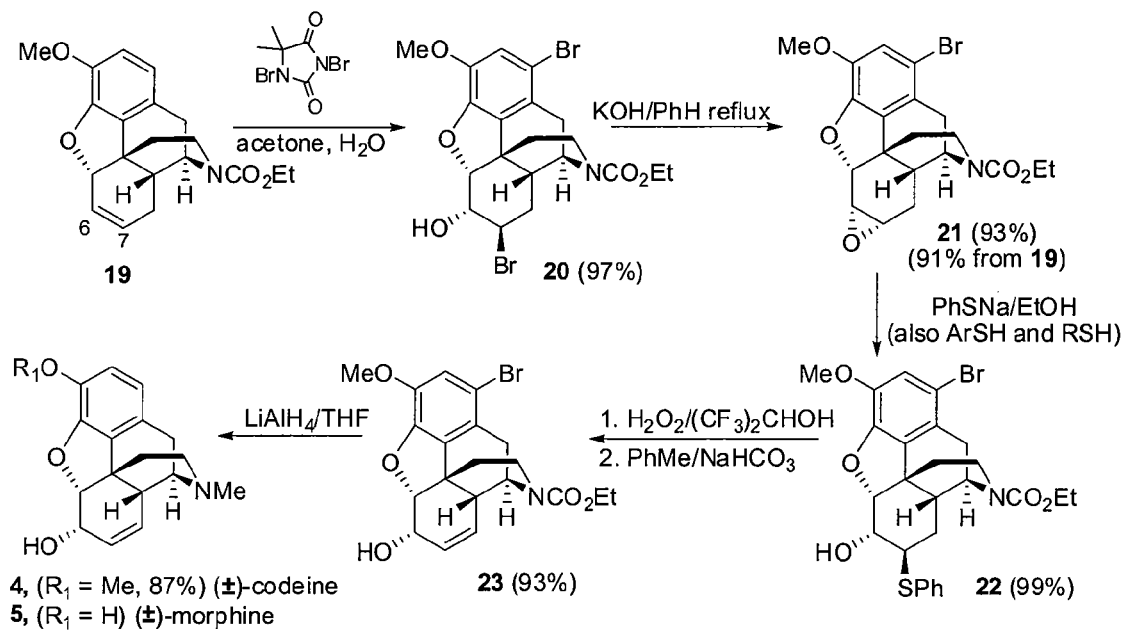
Figure 6:
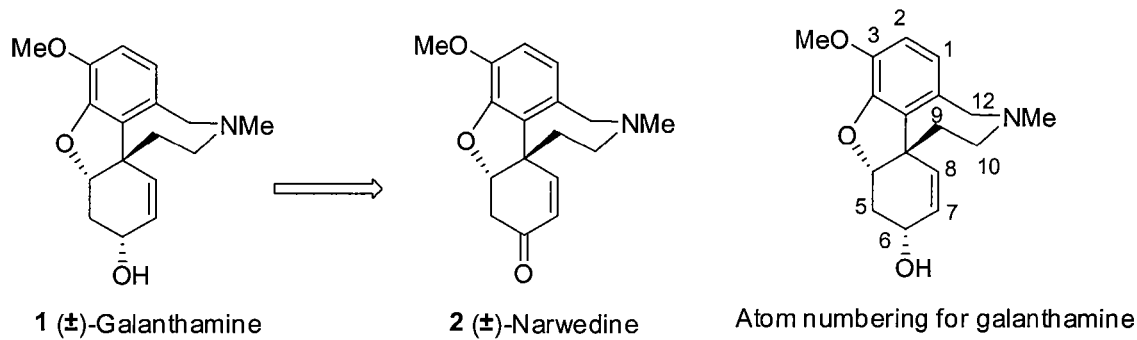
FIG. 6 shows the atomic numbering scheme for galanthamine and the structural similarity of narwedine.

The third and final phase involves the conversion of 19 into codeine 4. The prior literature dealing with this topic involves proceeding via codeinone 3 followed by reduction to 4. While not limiting the present invention to any particular theory, it is believed that the epoxidation of the 6,7-double bond proceeds from the least hindered face to give the R-epoxide, which eventually requires stereochemical inversion at $C_6$. As show in FIG. 5B, treatment of 19 with 3,3-dimethyl-1,5-dibromohydantoin gave 20 (97% yield). Exposure to KOH and PhH under reflux conditions resulted in the β-epoxide 21 (93% yield) with concomitant bromination at the $C_2$ position. Treatment of 21 with PhSNa/EtOH gave 22 (99% yield), and the derived sulfoxide thermally eliminated to give 23 (93% yield). Reduction of 23 with LiAlH$_4$/THF at 25° C. converted 23 into codeine 4 (87% yield).

Example II

In the following example, melting points were taken on a Thomas-Hoover capillary tube apparatus, and are uncorrected. Infrared spectra were recorded on a Thermo-Nicolet Avatar 360 FT-IR spectrophotometer, with the sample neat on KBr plates, unless otherwise indicated. $^1$H and $^{13}$C NMR spectra were recorded on a General Electric QE-300 spectrometer at 300 MHz, in the indicated solvent, and are reported in ppm relative to tetramethylsilane, or referenced internally to the residually protonated solvent. Mass spectra were obtained on a VG ZAB2E, or a Finnigan TSQ70 mass spectrometer.

Routine monitoring of reactions was performed using Merck 60 $F_{254}$ glass-backed silica gel TLC plates. Flash column chromatography was performed using EMD silica gel (particle size 0.040-0.063 μm). Solvents and commercial reagents were purified as disclosed in Perrin et al. *Purification of Laboratory Chemicals;* 3$^{rd}$ edition; Permagon Press: New York, 1993, or used without further purification. All reactions were conducted under an argon atmosphere, and solvents were degassed only when specified.

(4-Bromo-Phenoxy)-Triisopropylsilane

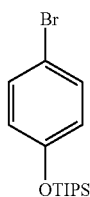

To a stirred solution of 4-bromophenol (25.1 g, 146 mmol), and imidazole (19.9 g, 292 mmol) in 1,2-dichloroethane (150 mL) at 23° C. was added triisopropylsilylchloride (34.4 mL, 161 mmol). The mixture was stirred for 12 h and poured onto saturated aqueous $NH_4Cl$ (400 mL), followed by extraction with $CH_2Cl_2$ (3×200 mL). The combined extracts were washed with brine (300 mL), dried ($Na_2SO_4$), and concentrated in vacuo to give a pale yellow oil which was crude oil was purified via short-path distillation (0.5 mmHg, 130° C.) to yield (4-Bromo-phenoxy)-triisopropylsilane as a colorless oil (53.0 g, 99% yield). $R_f$ 0.81 (3:1 hexanes/EtOAc) IR (thin film) 2945, 2892, 2867 cm$^{-1}$. $^1$H NMR (300 MHz, CDCl$_3$) δ 7.30 (2H, d, J=9 Hz), 6.75 (2H, d, J=9 Hz), 1.29-1.18 (3H, m), 1.08 (18H, d, J=7 Hz). $^{13}$C NMR (75 MHz, CDCl$_3$) δ 155.0, 132.0, 121.5, 112.9, 17.6, 12.4. HRMS calcd. for $C_{15}H_{26}OSiBr$ (MH$^+$) 329.0936, found 329.0937.

2-Bromo-3-Hydroxy-4-Methoxy-Benzaldehyde (8)

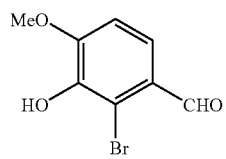

To a stirred suspension of isovanillin (10 g, 66 mmol), powdered anhydrous sodium acetate (10.82 g, 0.132 mol) and iron powder (0.3 g, 5.4 mmol) in glacial acetic acid (60 mL) under argon, was added drop-wise over 15 min a solution of $Br_2$ (3.7 mL, 0.0726 mol) in acetic acid (12.5 mL). The reaction temperature rose during the course of addition, and the mixture became viscous. After all the starting material was consumed, as determined by TLC, the mixture was poured onto ice cold water, and the resulting precipitate filtered under vacuum. The precipitate was washed several times with cold water and air-dried. Crystallization from boiling ethanol gave 8 (11.93 g, 79% yield) as a gray powder. $R_f$=0.10 (1:5 EtOAc/hexanes). M.p. 196-200° C. IR (thin film) 3215, 1662, 1588, 1561, 1491, 1273 cm$^{-1}$. $^1$H NMR (300 MHz, CDCl$_3$) δ 10.27 (1H, s), 7.59 (1H, d, J=9 Hz), 6.96 (1H, d, J=9 Hz), 6.02 (1H, bs), 4.00 (3H, s). $^{13}$C NMR (75 MHz, CDCl$_3$) δ 56.58, 109.24, 112.84, 113.84, 122.74, 143.25, 151.65, 190.87. HRMS calcd. for $C_8H_8O_3Br$ (MH$^+$) 230.9657. Found 230.9652.

2,4,6-Tris-(4-Triisopropylsilanyloxy-Phenyl)-Cyclotriboroxane (9)

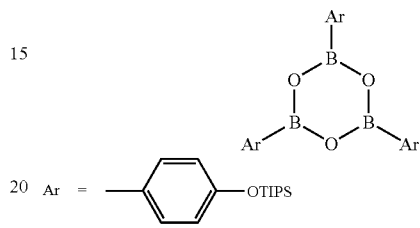

To a solution of (4-bromo-phenoxy)-triisopropylsilane (18.6 g, 56.7 mmol) in dry THF (500 mL) at −78° C. was added drop-wise a solution of n-BuLi (45 mL, 79.4 mmol, 2.5 M in THF). The resulting yellow solution was stirred 70 min at −78° C. before drop-wise addition of freshly distilled B(OPr$^i$)$_3$ (36 mL, 160 mmol). The mixture was stirred 12 h at 23° C. until all the starting material was consumed, as determined by thin layer chromatography (TLC). The mixture was combined with 10% aqueous $KHSO_4$ (300 mL), and extracted with EtOAc (3×200 mL). The combined extracts were washed with brine (200 mL), dried ($Na_2SO_4$) and concentrated in vacuo to yield an off-white solid. The crude solid was purified by flash column chromatography (SiO$_2$, 20% EtOAc/hexanes) to give a waxy white solid, which on azeotroping in toluene gave 9 (12.68 g, 76% yield) as a chalky white solid. M.p. 220° C. (hexanes). $R_f$ 0.51 (1:1 hexanes/EtOAc). IR (thin film) 3035, 2944, 2892, 2867 cm$^{-1}$. $^1$H NMR (300 MHz, CDCl$_3$) δ 8.11 (6H, d, J=8 Hz), 7.00 (6H, d, J=8 Hz), 1.35-1.28 (9H, m), 1.14 (54H, d, J=8 Hz). $^{13}$C NMR (75 MHz, CDCl$_3$) δ 159.9, 137.2, 122.6, 119.4, 17.7, 12.5. HRMS calcd. for $C_{45}H_{76}B_3O_6Si_3$ (MH$^+$) 829.5229. Found 829.5227.

6-Hydroxy-5-Methoxy-4'-(Triisopropylsilanyloxy)-Biphenyl-2-Carbaldehyde (R=TIPS) (10)

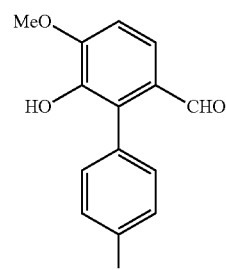

(R = TIPS, 96%)

To a degassed (30 min) mixture of 1,4-dioxane (9 mL) and water (4 mL) was added powdered K$_2$CO$_3$ (1.13 g, 8.16 mmol), 8 (0.687 g, 2.99 mmol), 9 (0.750 g, 2.72 mmol), 2,6-di-tent-butyl-4 methylphenol (BHT) (0.300 g, 1.36 mmol), and tricyclohexylphoshine (61 mg, 0.218 mmol). The mixture stirred for 15 min at 23° C. and [Pd$_2$(dba)$_3$] (0.100 g, 0.109 mmol) was added, and then heated at reflux for 1 h until all starting material was consumed, as determined by thin layer chromatography (TLC). The resulting dark colored mixture was poured onto saturated aqueous NH$_4$Cl (20 mL) and extracted with EtOAc (5×25 mL). The combined extracts were washed with brine (20 mL), dried (Na$_2$SO$_4$) and concentrated in vacuo to yield an orange oil. The crude oil was purified via flash column chromatography (SiO$_2$, 20% EtOAc/hexanes) to give 10 (1.05 g, 96% yield) as a thick yellow-orange oil. R$_f$ 0.61 (CH$_2$Cl$_2$). IR (thin film) 3538, 2945, 2892, 2867, 1683 cm$^{-1}$. $^1$H NMR (300 MHz, CDCl$_3$) δ 9.68 (1H, s), 7.64 (1H, d, J=9 Hz), 7.26-7.22 (2H, m), 7.01-6.96 (3H, m), 5.68 (1H, s), 4.01 (3H, s), 1.33-1.26 (3H, m), 1.13 (18H, d, J=7 Hz). $^{13}$C NMR (75 MHz, CDCl$_3$) δ 191.4, 155.8, 150.8, 142.3, 131.7, 129.1, 128.2, 124.5, 120.6, 119.5, 109.2, 56.0, 17.7, 12.5. HRMS calcd. for C$_{23}$H$_{33}$O$_4$Si (MH$^+$) 401.2148. Found 401.2148.

6-(2-Bromo-1-Ethoxy-Ethoxy)-5-Methoxy-4'-Triisopropylsilanyloxy-Biphenyl-2-Carbaldehyde (R=TIPS) (12)

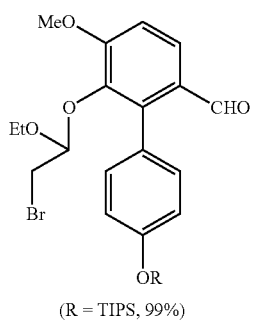

(R = TIPS, 99%)

To a solution of bromine (0.91 mL, 17.8 mmol) in CH$_2$Cl$_2$ (50 mL) at 0° C. was added drop-wise ethyl vinyl ether (2.13 mL, 22.2 mmol). The resulting colorless solution was stirred for 20 min at 0° C. and N,N-diisopropylamine (DIEA) (6.23 mL, 35.6 mmol) added drop-wise, followed by a CH$_2$Cl$_2$ (20 mL) solution of 10 (3.55 g, 8.9 mmol). The resulting solution was stirred for 16 h at 23° C., until all starting material was consumed, as determined by TLC. The mixture was poured onto saturated aqueous NaHCO$_3$ (100 mL), and extracted with CH$_2$Cl$_2$ (3×70 mL). The combined extracts were washed with brine (80 mL), dried (Na$_2$SO$_4$), and concentrated in vacuo to yield orange oil. The crude oil was purified via flash column chromatography (SiO$_2$, 10% EtOAc/hexanes) to give 12 (4.84 g, 99% yield) as a thick orange oil. R$_f$ 0.52 (3:1 hexanes/EtOAc). IR (thin film) 2966, 2944, 2892, 2867, 1684 cm$^{-1}$. $^1$H NMR (300 MHz, CDCl$_3$) δ 9.64 (1H, s), 7.85 (1H, d, J=8 Hz), 7.25-7.18 (2H, m), 7.03 (1H, d, J=8 Hz), 6.96 (2H, d, J=8 Hz), 5.06-5.02 (1H, m), 3.98 (3H, s), 3.65-3.55 (1H, m), 3.42-3.34 (1H, m), 3.12-3.01 (2H, m), 1.35-1.20 (3H, m), 1.13 (18H, d, J=7 Hz), 1.05 (3H, t, J=7 Hz). $^{13}$C NMR (75 MHz, CDCl$_3$) δ 191.1, 156.9, 156.1, 141.5, 140.5, 132.4, 128.4, 125.1, 119.4, 113.6, 111.0, 103.5, 64.5, 55.9, 31.7, 17.8, 14.9, 12.5. HRMS calcd. for C$_{27}$H$_{40}$O$_5$SiBr (MH$^+$) 551.1828. Found 551.1821.

Cross-Conjugated Cyclohexadienone (14)

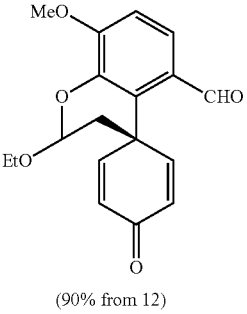

(90% from 12)

A suspension of dry CsF (0.490 g, 3.22 mmol) and 12 (0.590 g, 1.07 mmol) in DMF (11 mL, stored over activated 4 Å molecular sieves) were heated at reflux for 2 h. After all starting material was consumed, as determined by TLC, the mixture was poured onto saturated aqueous NaHCO$_3$ (100 mL) and extracted with EtOAc (3×70 mL). The combined extracts were washed with brine (80 mL), dried (Na$_2$SO$_4$), and concentrated in vacuo to yield orange oil which was purified via flash column chromatography (SiO$_2$, 25% EtOAc/hexanes) to give 14 (0.302 g, 90% yield) as thick orange oil which solidified upon standing to a orange solid. M.p. 74-80° C. R$_f$=0.23 (1:1 EtOAc/hexanes). IR (thin film) 2983, 2932, 2889, 1684, 1663, 1586 cm$^{-1}$. $^1$H NMR (300 MHz, CDCl$_3$) δ 9.95 (s, 1H), 7.75 (1H, dd, J's=10, 3 Hz), 7.64 (1H, d, J=9 Hz), 7.04 (1H, J's=10, 3 Hz), 6.98 (1H, d, J=9 Hz), 6.38 (1H, dd, J's=8, 2 Hz), 6.36 (1H, dd, J's=8, 2 Hz), 5.15 (1H, t, J=2 Hz), 4.00 (s, 3H), 3.96 (1H, m), 3.70 (1H, m), 2.40 (1H, dd, J's=14, 2 Hz), 2.01 (1H, dd, J's=14, 2 Hz), 1.22 (3H, t, J=7 Hz). $^{13}$C NMR (75 MHz, CDCl$_3$) δ 189.6, 184.4, 155.8, 155.5, 154.5, 140.1, 128.7, 126.0, 123.3, 122.8, 110.7, 94.8, 64.7, 56.2, 40.2, 39.8, 15.0. HRMS calcd. for C$_{18}$H$_{19}$O$_5$ (MH$^+$) 315.1232. Found 315.1231.

(4-Bromo-Phenoxy)-Tert-Butyl-Dimethylsilane

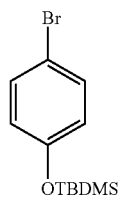

To a stirred solution of p-bromophenol (30 g, 0.1734 mol) in 1,2-dichloroethane (300 mL) at 23° C. was added imidazole (29.45 g, 0.433 mol). After 15 min, tert-butyldimethylsilylchloride (28.75 g, 0.190 mol) was added, and the resulting solution heated at reflux for 3 h. The mixture was cooled to room temperature and poured onto saturated aqueous NH$_4$Cl and extracted with CH$_2$Cl$_2$ (3×200 mL). The combined extracts were washed with brine (200 mL), dried (NaSO$_4$), filtered and evaporated in vacuo. The crude product was distilled via short-path distillation (0.5 mm Hg, 130° C.) to give (4-bromo-phenoxy)-tert-butyl-dimethylsilane (49.6 g, 99.5% yield) as a colorless oil. $R_f$=0.80 (1:3 EtOAc/hexanes). IR (thin film) 3390, 2951, 2928, 1584, 1479, 1250 cm$^{-1}$. $^1$H NMR (300 MHz, CDCl$_3$) δ 7.34 (1H, d, J=9 Hz), 6.74 (1H, d, J=9 Hz), 1.00 (12H, s), 0.21 (6H, s). $^{13}$C NMR (75 MHz, CDCl$_3$) δ 154.76, 132.22, 121.83, 113.55, 25.58, 18.12, −4.54. HRMS calcd. for C$_{12}$H$_{20}$BrOSi (MH$^+$) 287.0461. Found 287.0463.

2,4,6-Tris-[4-(Tert-Butyl-Dimethyl-Silanyloxy)-Phenyl]-Cyclotriboroxane (9a)

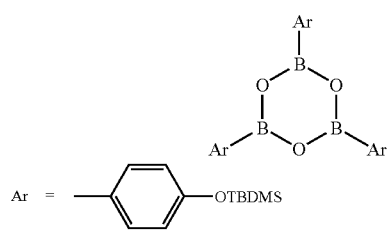

9a

To a solution of (4-bromo-phenoxy)-tert-butyl-dimethylsilane (10 g, 35 mmol) in THF (25 mL) at −78° C. was added drop-wise n-butyllithium (2.4 M in hexanes, 17.5 mL, 42 mmol) resulting in a yellow colored solution. After stirring the mixture for 30 min, freshly distilled triisopropoxyborate (24.2 mL, 105 mmol) was added drop-wise to the above solution, and the mixture was stirred overnight and allowed to warm to room temperature. The mixture was poured onto 10% aqueous KHSO$_4$ (50 mL) and extracted with EtOAc (3×150 mL). The combined extracts were washed with brine (200 mL), dried (Na$_2$SO$_4$), filtered and evaporated in vacuo. The crude white solid was dried by azeotroping in toluene (3×20 mL), and recrystallized from hexanes/EtOAc to give needle shaped crystals of 9a (6.9 g, 84.5% yield). M.p. 118-120° C. $R_f$=0.12 (1:5 EtOAc/hexanes). IR (thin film) 2955, 2928, 2854, 1592 cm$^{-1}$. $^1$H NMR (300 MHz, CDCl$_3$) δ 8.13 (2H, d, J=8 Hz), 6.97 (2H, d, J=8 Hz), 1.03 (9H, s), 0.27 (2H, s). $^{13}$C NMR (75 MHz, CDCl$_3$) δ 159.7, 137.4, 119.8, 25.7, 18.3, −4.3. HRMS calcd. for C$_{36}$H$_{58}$B$_3$O$_6$Si$_3$ (MH$^+$) 703.3820. Found 703.3826.

4'-(Tert-Butyl-Dimethyl-Silanyloxy)-6-Hydroxy-5-Methoxy-Biphenyl-2-Carbaldehyde (R=TBDMS) (11)

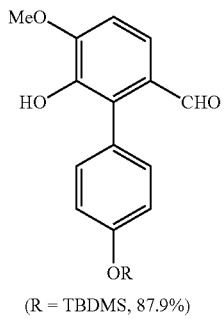

11

(R = TBDMS, 87.9%)

To a degassed (30 min) mixture of 1,4-dioxane (22.5 mL) and water (7.5 mL) was added powdered K$_2$CO$_3$ (2.48 g, 18 mmol), 8 (1.53 g, 6.6 mmol), 9a (1.5 g, 6 mmol), 2,6-di-tert-butyl-4 methylphenol (BHT) (spatula), and tricyclohexylphoshine (67 mg, 0.24 mmol). The mixture stirred for 15 min at 23° C. and [Pd$_2$(dba)$_3$] (0.114 g, 0.12 mmol) was added, and then heated at reflux for 1 h until all starting material was consumed, as determined by TLC. The resulting dark colored solution was poured onto saturated aqueous NH$_4$Cl (200 mL) and extracted with EtOAc (3×150 mL). The combined extracts were washed with brine (200 mL), dried (Na$_2$SO$_4$) and concentrated in vacuo to yield a yellow solid. Purification by flash column chromatography (SiO$_2$, 15% EtOAc/hexanes) gave 11 (2.1 g, 87.9% yield) as a pale yellow solid. M.p. 103-106° C. $R_f$=0.20 (1:5 EtOAc/hexanes). IR (thin film) 3401, 2930, 2857, 1684 cm$^{-1}$. $^1$H NMR (300 MHz, CDCl$_3$) δ 9.69 (1H, s), 7.65 (1H, d, J=9 Hz), 7.24 (1H, d, J=9 Hz), 6.98 (1H, d, J=9 Hz), 6.95 (1H, d, J=9 Hz), 5.67 (1H, bs), 4.02 (3H, s), 1.02 (9H, s), 0.26 (6H, s). $^{13}$C NMR (75 MHz, CDCl$_3$) δ 191.6, 155.7, 150.8, 142.7, 132.0, 131.5, 128.4, 120.5, 119.8, 109.6, 56.2, 25.6, 18.2, −4.4. HRMS calcd. for C$_{20}$H$_{27}$O$_4$Si (MH$^+$) 359.1679. Found 359.1675.

Conducting the above reaction on the following scale— K$_2$CO$_3$ (4.48 g, 32.4 mmol), 8 (2.75 g, 11.88 mmol), 9a (2.54 g, 10.8 mmol), 2,6-di-tert-butyl-4 methylphenol (BHT) (1.19 g, 5.4 mmol), tricyclohexylphoshine (0.24 g, 0.864 mmol), [Pd$_2$(dba)$_3$] (0.40 g, 0.432 mmol) in dioxane (36 mL) and water (15.5 mL) gave 11 (3.836 g, 99% yield).

6-(2-Bromo-1-Ethoxy-Ethoxy)-4'-(Tert-Butyl-Dimethyl-Silanyloxy)-5-Methoxy-Biphenyl-2-Carbaldehyde (R=TBDMS) (13)

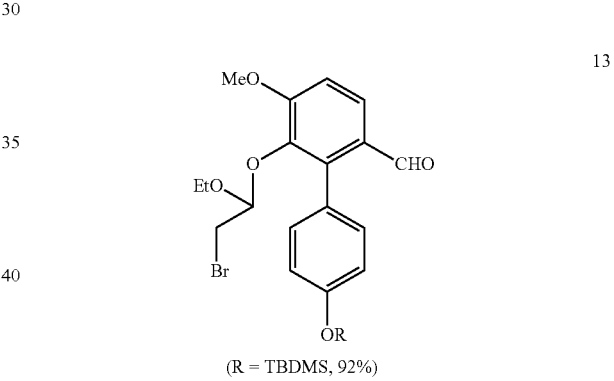

13

(R = TBDMS, 92%)

To a solution of Br$_2$ (0.397 mL, 7.74 mmol) in CH$_2$Cl$_2$ (30 mL) at 0° C. was added drop-wise ethyl vinyl ether (0.92 mL, 9.68 mmol) until the solution turned colorless. The mixture was stirred for 15 min and diisopropylethyamine (2.71 mL, 15.48 mmol) was added followed by a drop-wise addition of a solution of 11 (1.5 g, 3.87 mmol) in CH$_2$Cl$_2$ (15 mL) The mixture was stirred for 12 h under an argon atmosphere to give an orange-red solution. After complete consumption of staring material, as determined by TLC. the mixture was poured onto saturated aqueous NaHCO$_3$ and extracted with CH$_2$Cl$_2$ (3×50 mL). The combined extracts were washed with brine (100 mL), dried (Na$_2$SO$_4$), filtered and evaporated in vacuo to give an orange-red oil. Purification by flash column chromatography (SiO$_2$, 10% EtOAc/Hexanes) gave 13 (1.92 g, 92% yield) as a colorless syrupy liquid. (1.92 g, 92% yield). $R_f$=0.42 (1:5 EtOAc/hexanes). IR (thin film) 2956, 2930, 2857, 1684 cm$^{-1}$. $^1$H NMR (300 MHz, CDCl$_3$) δ 9.64 (1H, s), 7.85 (1H, d, J=9 Hz), 7.25-7.18 (2H, m), 7.03 (1H, d, J=9 Hz), 6.93 (2H, d, J=9 Hz), 5.01 (1H, dd, J's=7, 4 Hz), 3.98 (3H, s), 3.56 (1H, m), 3.31 (1H, m), 3.09 (2H, m), 1.05 (2H, t, 7 Hz), 1.01 (9H, s), 0.24 (6H, s). $^{13}$C NMR (75 MHz, CDCl$_3$) δ 191.5, 157.02, 155.8, 141.7, 140.6, 132.5, 128.5, 125.2, 119.7, 111.0, 103.7, 64.5, 55.9, 31.8, 25.6, 18.2, 14.9, −4.4. HRMS calcd. for $C_{24}H_{34}O_5SiBr$ (MH$^+$) 509.1359. Found 509.1356.

Conducting the above reaction on the following scale—Br$_2$ (1.64 mL, 32 mmol) in CH$_2$Cl$_2$ (126 mL), ethyl vinyl ether (3.8 mL, 40 mmol), diisopropylethyamine (11.2 mL, 64 mmol) 11 (5.73 g, 16 mmol) gave 13 (8.10 g, 99% yield).

Cross-Conjugated Cyclohexadienone (14)

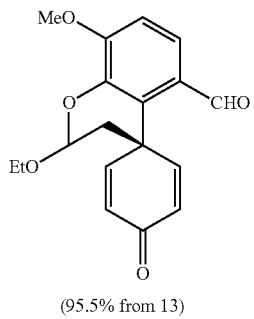

(95.5% from 13)

A flame-dried mixture of CsF (0.22 g, 1.44 mol) and Na$_2$SO$_4$ (0.68 g, 4.8 mmol) was added to a solution of 13 (0.26 g, 0.48 mmol) in DMF (3.7 mL, stored over 4 Å molecular sieves) and the reaction mixture was heated at 130° C. for 1.5 h. After completion of the reaction, as determined by TLC, the reaction mixture was poured into saturated aqueous NaHCO$_3$ (25 mL) and extracted with EtOAc (4×20 mL). The combined extracts were successively washed with water (3×25 mL), brine (50 mL), dried (Na$_2$SO$_4$), filtered and concentrated in vacuo to give a brown syrup. Purification by flash chromatography (SiO$_2$, 30% EtOAc/hexanes) gave compound 14 (0.137 g, 95.5% yield).

Conducting the above reaction on the following scale: 13 (7.0 g, 13.8 mmol), CsF (6.5 g, 41.3 mmol) in DMF (138 mL) gave 14 (4.24 g, 94%).

6-Ethoxy-8-Methoxy-12-Nitro-1,5,6,12a-Tetrahydro-Naphtho[8a,1,2-de]Chromen-2-One (15)

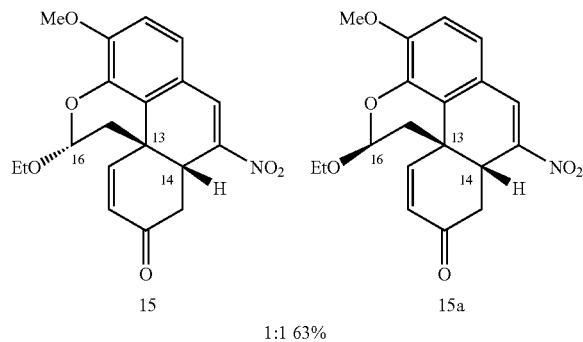

1:1 63%

A mixture of the dienone 14 (1.0 g, 3.18 mmol), NH$_4$OAc (0.98 g, 12.7 mmol), and nitromethane (1.01 mL, 19.08 mmol) in acetic acid (15 mL) was heated at reflux for 2 h. After completion of the reaction, as determined by TLC, the solvent was evaporated in vacuo and the residue was washed with water (40 mL) and extracted with diethylether (3×50 mL). The combined extracts were washed with brine (50 mL), dried (Na$_2$SO$_4$), filtered and concentrated in vacuo to give a brown solid. Purification by flash chromatography (SiO$_2$, 20% EtOAc/hexanes) gave bright yellow crystals of the two diastereomers 15 and 15a (0.72 g, 63% yield) in approximately 1:1 ratio. Data for 15. R$_f$=0.47 (1:1 EtOAc/hexanes). M.p. 165-170° C. IR (thin film) 2920, 2842, 1685, 1565 cm$^{-1}$. $^1$H NMR (300 MHz, CDCl$_3$) δ 7.56 (1H, d, J=2 Hz), 6.96 (1H, d, J=8 Hz), 6.86 (1H, d, J=8 Hz), 6.48 (1H, dd, J's=10, 2 Hz), 5.98 (1H, d, J=10 Hz), 5.38 (1H, dd, J's=9, 3 Hz), 4.16 (1H, m), 3.92 (3H, s), 3.74 (1H, m), 3.50 (1H, m), 3.28 (1H, dd, J's=6, 2 Hz), 2.89 (1H, dd, J's=18, 5 Hz), 2.66 (1H, dd, J's=13, 3 Hz), 2.27 (1H, dd, J's=13, 9 Hz), 1.29 (3H, t, J=7 Hz). $^{13}$C NMR (75 MHz, CDCl$_3$) δ 194.6, 150.0, 146.9, 141.4, 132.2, 128.7, 123.9, 121.3, 111.3, 97.7, 65.3, 56.1, 42.1, 39.1, 38.8, 34.2, 15.1. HRMS calcd. for $C_{19}H_{20}NO_6$ (MH$^+$) 358.1291. Found 358.1290.

Data for 15a. R$_f$=0.47 (1:1 EtOAc/Hexanes). M.p. 161-164° C. IR (thin film) 2974, 2926, 2853, 1684, 1570 cm$^{-1}$. $^1$H NMR (300 MHz, CDCl$_3$) δ 7.58 (1H, d, J=2 Hz), 7.00 (1H, d, J=9 Hz), 6.90 (1H, d, J=9 Hz), 6.75 (1H, dd, J's=10, 1.5 Hz), 5.92 (1H, d, J=10 Hz), 5.59 (1H, d, J=3 Hz), 3.95 (1H, m), 3.96 (3H, s), 3.70 (1H, m), 3.45 (1H, dd, J's=4, 2 Hz), 3.27 (1H, dd, J=9, 1.5 Hz), 2.88 (1H, dd, J=18, 5 Hz), 2.70 (1H, dd, J's=13, 1.5 Hz), 2.33 (1H, dd, J's=13, 3 Hz), 1.20 (3H, t, J=7 Hz). $^{13}$C NMR (75 MHz, CDCl$_3$) δ 194.9, 152.3, 147.4, 140.4, 132.2, 126.9, 123.9, 121.3, 110.9, 96.2, 68.1, 64.6, 56.1, 43.1, 37.2, 36.2, 34.4, 29.64, 15.1.

Example III

To the dienone 14 (5.0 g, 15.93 mM) in nitromethane (50 mL), was added NH$_4$OAc (0.5 g) and acetic acid (5 mL) and the solution was heated at reflux for 2.5 h. When 14 had been consumed (TLC), the mixture was poured into brine (50 mL) and the layers separated. The aqueous layer was successively washed with ether (2×40 mL). The combined organics were dried (Na$_2$SO$_4$) and concentrated in vacuo to give (5.5 g, 97% yield) of 15/15a as a racemic mixture of two diastereomers in a 1:1 ratio. NMR analysis indicated that the crude mixture was pure enough to be carried forward without purification.

6-Ethoxy-8-Methoxy-12-Nitro-1,5,6,11,12,12a-Hexahydro-Naphtho[8a,1,2-de]Chromen-2-One (16)

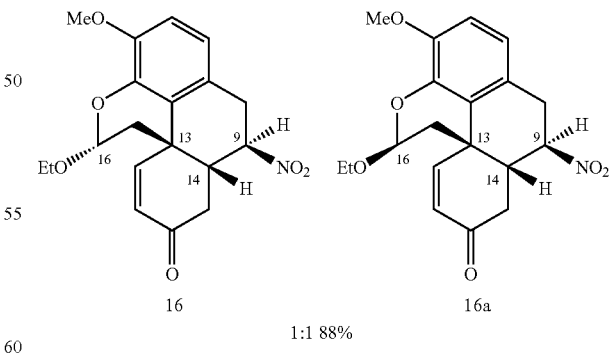

1:1 88%

To a solution of the nitroalkenes 15/15a (127 mg, 0.36 mmol) in THF (3.5 mL) and phosphate buffer (pH 4.5, 1.5 mL) at 0° C. was added NaBH$_3$CN (23.5 mg, 0.37 mmol) in small portions, and the resulting solution was stirred for 1 h until all the starting material was consumed as determined by TLC. The mixture was combined with aqueous NH$_4$Cl (5 ml)

and extracted with EtOAc (3×5 mL). The combined organic extracts were washed with brine (15 mL), dried (Na$_2$SO$_4$), filtered and concentrated in vacuo to give a pale yellow solid. Purification by flash column chromatography (SiO$_2$, 30% EtOAc/hexanes) gave 16 and 16a as white solids (112 mg, 88% yield). R$_f$=0.55 (1:1 EtOAc/Hexanes). Data for 16. M.p. 168° C. IR (thin film) 2975, 2932, 1684, 1551 cm$^{-1}$. $^1$H NMR (300 MHz, CDCl$_3$) δ 6.84 (1H, d, J=9 Hz), 6.82 (1H, dd, J's=10, 4 Hz), 6.73 (1H, d, J=9 Hz), 6.06 (1H, d, J=10 Hz), 5.50 (1H, dd, J's=8, 6 Hz), 4.92 (1H, m), 4.10 (1H, m), 3.88 (3H, s), 3.67 (1H, m), 3.33 (2H, m), 2.86 (3H, m), 2.46 (1H, d, J=18 Hz), 2.00 (1H, dd, J's=13, 8 Hz), 0.26 (3H, t, J=7 Hz). $^{13}$C NMR (75 MHz, CDCl$_3$) δ 194.0, 152.0, 148.6, 141.0, 128.5, 125.2, 122.2, 121.5, 112.5, 98.2, 83.8, 64.4, 56.2, 43.6, 42.4, 38.1, 35.9, 33.2, 14.9. HRMS calcd. for C$_{19}$H$_{22}$NO$_6$ (MH$^+$) 360.1447. Found 360.1443.

Data for 16a. R$_f$=0.55 (1:1 EtOAc/Hexanes). M.p. 201° C. IR (thin film) 2975, 2932, 1685, 1551 cm$^{-1}$. $^1$H NMR (300 MHz, CDCl$_3$) δ 6.87 (2H, m), 6.06 (1H, d, J=10 Hz), 5.50 (1H, dd, J's=8, 6 Hz), 4.92 (1H, m), 4.10 (1H, m), 3.88 (3H, s), 3.67 (1H, m), 3.33 (2H, m), 2.86 (3H, m), 2.46 (1H, d, J=18 Hz), 2.00 (1H, dd, J's=13, 8 Hz), 0.26 (3H, t, J=7 Hz). $^{13}$C NMR (75 MHz, CDCl$_3$) δ 194.0, 152.0, 148.6, 141.0, 128.5, 125.2, 122.2, 121.5, 112.5, 98.2, 83.8, 64.4, 56.2, 43.6, 42.4, 38.1, 35.9, 33.2, 29.6, 14.9; HRMS calcd. for C$_{19}$H$_{22}$NO$_6$ (MH$^+$) 360.1447. Found 360.1443.

12-Amino-6-Ethoxy-8-Methoxy-1,5,6,11,12,12a-Hexahydro-2H-Naphtho[8a,1,2-de]Chromen-2-Ol (17/17a)

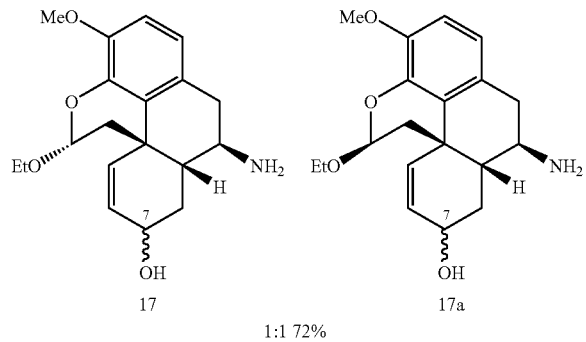

17        17a

1:1 72%

To a solution of the nitroalkanes 16/16a (468 mg, 1.3 mmol) in THF (15 ml) cooled to −78° C. under argon, was added LiAlH$_4$ (2M in THF, 3.9 mL) drop-wise over a 20 minute interval. The resulting solution was stirred at −78° C. for 1 h and allowed to warm to room temperature (RT) over 8 h. The reaction was checked for completion by TLC, and then added to saturated aqueous Na$_2$SO$_4$ (5 ml) at 0° C. The salts were filtered through a Buchner funnel and washed with (100 ml) of ether. The organic layer was washed with brine (15 ml), dried (Na$_2$SO$_4$), and concentrated in vacuo to yield a pale yellow foamy solid. The crude product can be purified by column chromatography (SiO$_2$, 1% NEt$_3$, 10% MeOH, 89% CH$_2$Cl$_2$) to yield a white foamy solid (312 mg, 72%). R$_f$=0.26 (15% MeOH/CH$_2$Cl$_2$). Data for 17. IR (thin film) 3352, 3287, 2924, 1497, 1439 cm$^{-1}$. $^1$H NMR (300 MHz, CDCl$_3$) δ 6.84 (1H, d, J=8 Hz), 6.71 (1H, d, J=9 Hz), 6.00 (1H, d, J=10 Hz), 5.90 (1H, dd, J's=10, 3 Hz), 5.50 (1H, dd, J's=8, 6.6 Hz), 4.42-4.17 (1H, m), 4.11-4.05 (1H, m), 3.86 (3H, s), 3.83-3.61 (1H, m), 3.42-3.90 (1H, m), 3.05 (1H, dd, J's=16, 3 Hz), 2.76 (1H, dd, J's=16, 3 Hz), 2.60 (1H, dd, J's=12.5, 6 Hz), 2.50 (1H, m), 2.02 (2H, m), 2.02 (1H, bd, 15 Hz), 1.57 (1H, dd, J's=12.5, 8 Hz), 1.21 (3H, t, J=7 Hz). $^{13}$C NMR (75 MHz, CDCl$_3$) δ 148.4, 141.6, 132.2, 131.0, 127.7, 123.3, 122.4, 111.6, 99.2, 65.8, 64.2, 59.8, 56.2, 49.8, 44.8, 38.2, 34.6, 31.1, 15.1. HRMS calcd. for C$_{19}$H$_{26}$NO$_4$ (MH$^+$) 332.1859, found 332.1856.

Data for 17a. R$_f$=0.21 (15% MeOH/CH$_2$Cl$_2$). IR (thin film) 3342, 3287, 2924, 2856, 1493, 1441, 1375, 1260, 1210, 1123, 1035, 1009 cm$^{-1}$. $^1$H NMR (300 MHz, CDCl$_3$) δ 6.77 (1H, d, J=8 Hz), 6.69 (1H, d, J=8 Hz), 5.89 (1H, d, J=10 Hz), 5.90 (1H, d, J=10 Hz), 5.50 (1H, d, J=2 Hz), 4.44-4.37 (1H, m), 4.05-3.90 (1H, m), 3.86 (3H, s), 3.85-3.62 (1H, m), 3.26 (1H, m), 2.97 (2H, m), 2.67-2.34 (3H, m), 2.21 (2H, dd, J's=17, 7 Hz), 2.02-1.86 (1H, m), 1.61 (1H, bs), 1.21 (3H, t, J=7 Hz). $^{13}$C NMR (75 MHz, CDCl$_3$) δ 147.4, 140.6, 135.9, 128.1, 127.0, 125.6, 120.8, 110.4, 97.7, 64.3, 64.2, 56.2, 50.1, 45.8, 42.2, 38.1, 34.7, 33.1, 15.2.

Core Secondary Amine (18)

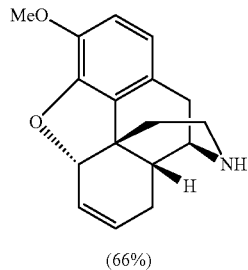

18

(66%)

To a solution of the primary amines 17/17a (1.0 g, 3.02 mM) in dioxane (48 mL) was added 1N HCl (16 mL) and stirred for 10 mM NaCNBH$_3$ (569 mg, 9.06 mM) was added in 3 portions after every 1 h. The mixture was taken to reflux and heated at reflux for 5 h. The pH was maintained between 2-3 by adding 1N HCl as required. The reaction was checked for completion by TLC, cooled to RT, and basified to pH 10 with 1M NaOH (aq.) and extracted with diethyl ether (5×25 mL). The combined organics were washed with brine (30 mL), dried (Na$_2$SO$_4$) and conc. in vacuo to yield a brown syrup (730 mg).

The crude product can be purified by column chromatography (SiO$_2$, 1% NEt$_3$, 10% MeOH, 89% CH$_2$Cl$_2$) to yield pure 18 as a colorless syrup (540 mg, 66% yield). R$_f$=0.12 (15% MeOH/CH$_2$Cl$_2$). IR (thin film) 3307, 3024, 2920, 2847, 1634, 1504, 1439, 1278, 1256, 1194, 1159, 1127, 1063, 1037 cm$^{-1}$. $^1$H NMR (300 MHz, CDCl$_3$) δ 6.71 (1H, d, J=8 Hz), 6.30 (1H, d, J=8 Hz), 5.86 (1H, m), 5.71 (1H, m), 4.93 (1H, s), 3.86 (3H, s), 3.43 (1H, m), 3.00 (1H, dd, J's=12, 6 Hz), 2.84 (2H, m), 2.76 (1H, d, J=18 Hz), 2.35 (1H, m), 1.96 (1H, t, J=6 Hz), 1.90 (1H, t, J=6 Hz), 1.80 (1H, m), 1.45 (1H, m). $^{13}$C NMR (75 MHz, CDCl$_3$) δ 144.6, 143.1, 131.9, 129.5, 127.1, 124.5, 118.4, 112.7, 87.7, 56.1, 51.9, 49.9, 41.5, 39.1, 38.8, 30.7, 24.4. HRMS calcd. for C$_{17}$H$_{20}$NO$_2$ (MH$^+$) 270.1494. Found 270.1498.

Ethyl Carbamate (19)

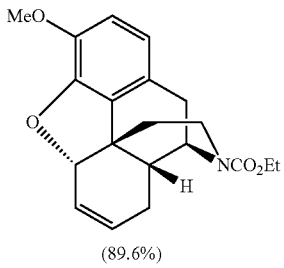

(89.6%)

To a solution of the secondary amine 18 (0.70 g, 2.6 mmol) in CH$_2$Cl$_2$ (20 ml) cooled to 0° C. was added triethylamine (1.81 mL, 13.0 mmol) and ethyl chloroformate (0.62 mL, 6.5 mmol) dropwise over 2 min. The resulting solution was stirred at 0° C. for 1 hour. After checking for completion by TLC, the reaction mixture was quenched with saturated aqueous NH$_4$Cl (20 mL) and extracted with CH$_2$Cl$_2$ (3×20 mL). The combined extracts were washed with brine (25 mL), dried (Na$_2$SO$_4$) and evaporated in vacuo to give a pale yellow oil. The crude product can be purified by column chromatography (SiO$_2$, 30% EtOAc/hexanes) to yield a colorless syrup (0.795 g, 89.6% yield). R$_f$=0.48 (30% EtOAc/hexanes). IR (thin film) 2978, 2931, 2838, 1695 cm$^{-1}$. $^1$H NMR (300 MHz, CDCl$_3$) δ 6.73 (1H, d, J=8 Hz), 6.62 (1H, d, J=8 Hz), 5.85 (11 μm), 5.71 (1H, d, J=10 Hz)), 4.95 (1H, s), 4.71 (major amide rotamer 0.60H, bs), 4.56 (minor amide rotamer 0.4 H, bs), 4.15 (2H, q, J=7.2 Hz), 4.1-3.93 (1H, m), 3.85 (3H, s), 3.06-2.86 (2H, m), 2.68 (1H, d, J=18 Hz), 2.30-2.25 (1H, m), 2.00 (1H, dt, J's=18, 6 Hz), 1.90-1.70 (2H, m), 1.53-1.40 (1H, m), 1.27 (3H, t, J=7.2 Hz). $^{13}$C NMR (75 MHz, CDCl$_3$) Major rotamer: δ155.4, 144.9, 143.4, 131.9, 128.5, 125.8, 124.4, 118.9, 113.3, 87.4, 61.4, 56.2, 50.1, 41.1, 37.7, 35.0, 28.8, 24.0, 14.7. Minor rotamer: δ 155.0, 144.8, 143.4, 131.6, 128.5, 125.6, 124.6, 118.9, 113.3, 87.4, 61.4, 56.2, 50.5, 41.1, 37.7, 34.8, 29.0, 24.1, 14.6. HRMS calcd. for C$_{20}$H$_{24}$NO$_4$ (MH$^+$) 342.1705. Found 360.1699.

Bromohydrin (20)

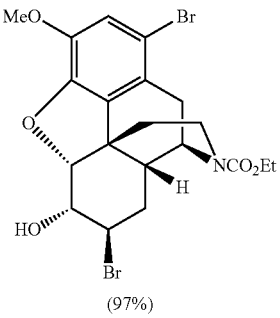

(97%)

To a solution of 19 (250 mg, 0.73 mmol) in acetone/H$_2$O (10:1, 11 mL) was added recrystallized 2,2 bromo-3,5 dimethylhydantoin (520 mg, 1.83 mmol) in small portions over 5 min. The entire set-up was covered with aluminum foil, placed in the dark and stirred for 12 h until all the starting material was consumed as determined by TLC. The reaction mixture was quenched with saturated NH$_4$Cl (10 ml), diluted with water (10 ml) and extracted with ethyl acetate (3×15 ml). The combined extracts were washed with brine (20 mL), dried (Na$_2$SO$_4$) and evaporated in vacuo to give a yellow oil. The crude product can be purified by column chromatography (SiO$_2$, 50% EtOAc/hexanes) to yield a colorless syrup (365 mg, 97%) or can be carried forward onto the next step without purification. R$_f$=0.26 (1:1 EtOAc/hexanes). IR (thin film) 3420, 2978, 2937, 2889, 1684 cm$^{-1}$. $^1$H NMR (300 MHz, CDCl$_3$) δ 6.98 (1H, s), 4.83 (1H, d, J=7 Hz), 4.78 (Major rotamer 0.60H, bs), 4.63 (Minor rotamer 0.4H, bs), 4.11 (2H, q, J=7.2 Hz), 4.1-3.94 (1H, m), 3.89 (3H, s), 3.72-2.59 (2H, m), 2.77-2.61 (1H, m), 2.52 (1H, bs), 2.00 (1H, dt, J's=17, 3.7 Hz), 2.20 (1H, m), 1.75-1.70 (1H, m), 1.27 (3H, t, J=7.2 Hz); 1.07-0.95 (1H, m). $^{13}$C NMR (75 MHz, CDCl$_3$) Major rotamer: δ 155.4, 145.1, 143.3, 129.3, 125.2, 117.7, 113.5, 95.8, 70.5, 61.8, 60.4, 56.8, 50.2, 45.4, 38.4, 37.8, 34.4, 31.9, 29.8, 14.6. Minor rotamer: δ 155.0, 145.1, 143.3, 129.3, 125.2, 117.7, 113.5, 95.8, 70.2, 61.7, 60.4, 56.8, 50.6, 45.4, 38.3, 38.2, 34.1, 31.9, 30.1, 14.7. HRMS calcd. for C$_{20}$H$_{24}$NO$_4$Br$_2$ (MH$^+$) 516.0021. Found 516.0018.

Epoxide (21)

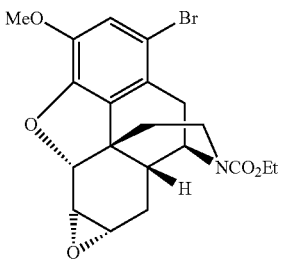

(93% from 19)

To a solution of the bromohydrin 20 (365 mg, 0.71 mM) in toluene (15 mL) was added solid KOH (200 mg) and the mixture was heated at 80° C. for 3 hours until all the starting material was consumed (TLC). The reaction mixture was cooled and diluted with water (15 ml) and extracted with ethyl acetate (3×20 mL). The combined organics were washed with brine (10 mL), dried (Na$_2$SO$_4$) and conc. in vacuo to give a yellow oil. The crude product was purified by column chromatography (SiO$_2$, 40% EtOAc/hexanes) to yield 21 as a colorless syrup (295 mg, 95.6%). R$_f$=0.37 (1:1 EtOAc/hexanes). IR (thin film) 2963, 2926, 2850, 1695, 1684 cm$^{-1}$. $^1$H NMR (300 MHz, CDCl$_3$) δ 6.91 (1H, s), 4.87 (1H, d, J=3.7 Hz), 4.70 (major amide rotamer 0.70H, bs), 4.56 (minor amide rotamer 0.3H, bs), 4.13 (2H, q, J=7.3 Hz), 4.1-3.89 (1H, m), 3.86 (3H, s), 3.30-2.23 (2H, m), 2.79-2.70 (2H, m), 2.53 (1H, d, J=18 Hz), 2.00 (2H, m), 1.79-1.68 (2H, m), 1.27 (3H, t, J=7.2 Hz); 1.15-1.06 (1H, m). $^{13}$C NMR (75 MHz, CDCl$_3$) Major rotamer: δ155.2, 146.1, 142.9, 129.2, 124.2, 116.7, 112.0, 87.6, 61.4, 56.4, 53.5, 50.9, 49.8, 41.1, 37.3, 36.2, 35.9, 29.9, 22.7, 14.5. Minor rotamer: δ 154.8, 146.1, 142.9, 129.2, 124.0, 116.7, 112.0, 87.6, 61.5, 56.5, 53.5, 50.9, 50.2, 41.1, 37.2, 36.3, 35.9, 30.2, 22.9, 14.6. HRMS calcd. for C$_{20}$H$_{23}$BrNO$_5$ (MH$^+$) 436.0760. Found 436.0758.

Alternatively, the epoxides 21 may be obtained by mixing a solution of the carbamate 19 (70 mg, 0.205 mM) in 1,4 dioxane (3 mL) and water (1 mL) and further adding recrystallized 1,3 bromo-5,5 dimethyl hydantoin (60.0 mg, 0.21 mM) and stirring for 12 hours in the dark. After 19 was consumed (TLC), solid KOH (50 mg) was added and the solution was heated at 80° C. for 2.5 h. After all the intermediate bromohydrin 20 was consumed (TLC), the solution was diluted with water (10 mL) and extracted with ethyl acetate (3×10 mL). The combined organics were washed with brine (10 mL), dried (Na$_2$SO$_4$) and concentrated in vacuo to give a pale, yellow oil. The crude product was purified by column chromatography (SiO$_2$, 40% EtOAc/hexanes) to yield 21 as a colorless syrup (81 mg, 91%).

Phenyl Sulfide (22)

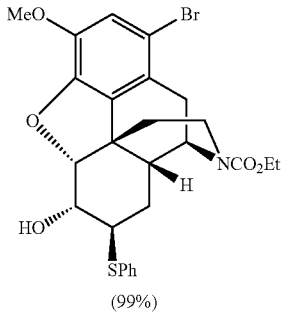

To a solution of diphenyl disulfide (12 mg, 0.055 mmol) in EtOH (1.0 mL) was added NaBH$_4$ (4 mg, 0.11 mmol) portion-wise over 5 min. The resulting solution was stirred for 15 min and then added drop-wise to a solution of the epoxide 21 (16 mg, 0.037 mmol) in EtOH (1.0 mL). The resulting solution was stirred at 25° C. for 2 h until all the substrate was consumed (TLC). The mixture was diluted with water (5 mL) and extracted with CH$_2$Cl$_2$ (3×5 mL). The combined organics were washed with brine (5 mL), dried (Na$_2$SO$_4$) and conc. in vacuo to give a pale yellow solid. The crude product was purified by column chromatography (SiO$_2$, 30% EtOAc/hexanes) to yield 22 as a white solid (20 mg, 99% yield). R$_f$=0.60 (40% EtOAc/hexanes). IR (thin film) 3446, 2936, 1684, 1487, 1437, 1323, 1300, 1274, 1229, 1191, 1172, 1148, 1065, 1023 cm$^{-1}$. $^1$H NMR (300 MHz, CDCl$_3$) δ 7.39 (2H, d, J=7.3 Hz), 7.30 (3H, m), 6.93 (1H, s), 4.88 (1H, d, J=5 Hz), 4.69 (Major rotamer 0.60H, bs), 4.54 (Minor rotamer 0.4H, bs), 4.14 (2H, q, J=7.2 Hz), 4.07-3.91 (2H, m), 3.84 (3H, s), 3.36-3.28 (2H, m), 2.79-2.59 (2H, m), 2.39-2.34 (2H, m), 1.85-1.56 (4H, m), 1.27 (3H, t, J=7.2 Hz); $^{13}$C NMR (75 MHz, CDCl$_3$) Major rotamer: δ155.3, 145.8, 142.8, 132.3, 129.2, 127.7, 125.1, 116.6, 112.8, 89.0, 68.4, 61.5, 60.3, 56.4, 50.5, 46.5, 42.5, 37.6, 36.2, 36.0, 29.9, 24.4, 21.0, 14.6; Minor rotamer: δ 155.0, 145.8, 142.8, 133.2, 132.0, 130.7, 129.2, 127.7, 124.8, 116.6, 112.8, 89.0, 68.4, 61.6, 56.4, 51.0, 46.5, 42.3, 37.6, 36.4, 35.7, 30.1, 24.4, 14.7; HRMS calcd. for C$_{26}$H$_{28}$BrNO$_5$S (MH$^+$) 568.0758. Found 568.0764.

Allylic Alcohol (23)

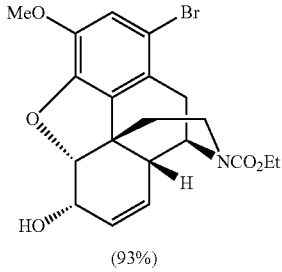

To a solution of 22 (20 mg, 0.036 mmol) in hexafluoroisopropanol (0.5 mL) was added hydrogen peroxide (30% aq., 0.05 mL) and the resulting solution was stirred for 15 min until all starting material was consumed (TLC). The reaction mixture was diluted with water (5 ml) and quenched with saturated aqueous Na$_2$SO$_3$ (2 mL) and the two phases were separated. The aqueous layer was extracted with CH$_2$Cl$_2$ (2×5 mL) and the combined extracts were washed with brine (5 mL), dried (Na$_2$SO$_4$) and conc. in vacuo to give a pale yellow solid. The crude product was dissolved in toluene (2 mL) and solid NaHCO$_3$ (15 mg) was added. The mixture was heated at reflux for 2 h until all the intermediate sulfoxide had been consumed. The reaction was diluted with water (10 mL) and extracted with CH$_2$Cl$_2$ (3×5 mL). The combined extracts were washed with brine (5 mL), dried (Na$_2$SO$_4$) and conc. in vacuo to give a pale yellow syrup. The crude product was purified by column chromatography (SiO$_2$, 50% EtOAc/hexanes) to yield a colorless syrup (14 mg, 87% yield). R$_f$=0.60 (40% EtOAc/Hexanes). IR (thin film) 3446, 2978, 2932, 2868, 1684, 1489, 1435, 1321, 1227, 1170, 1147, 1054 cm$^{-1}$. $^1$H NMR (300 MHz, CDCl$_3$) δ 6.94 (1H, s), 5.77 (1H, d, J=8.8 Hz), 5.30 (1H, dd, J=6.6, 1.5 Hz), 5.02 (Major rotamer 0.60H, bs), 4.90 (1H, d, J=6.6 Hz), 4.88 (Minor rotamer 0.4H, bs), 4.14 (2H, q, J=7.2 Hz), 3.84 (3H, s), 2.96-2.84 (2H, m), 2.78-2.66 (3H, m), 2.60-2.52 (1H, d, J=21 Hz), 2.45-2.41 (1H, m), 1.95-1.87 (4H, m), 1.27 (3H, t, J=7.2 Hz); $^{13}$C NMR (75 MHz, CDCl$_3$) Major rotamer: δ155.3, 145.9, 143.3, 134.4, 131.3, 126.9, 125.5, 116.2, 113.3, 91.4, 66.0, 56.4, 50.3, 47.8, 43.8, 39.3, 37.2, 35.3, 29.7, 14.6; Minor rotamer: δ 155.0, 145.9, 143.3, 134.7, 131.3, 126.8, 125.3, 117.7, 113.5, 91.4, 61.7, 56.8, 49.9, 47.8, 41.1, 39.7, 37.7, 34.9, 29.9, 14.7. HRMS calcd. for C$_{20}$H$_{23}$BrNO$_5$ (MH$^+$) 436.0757. Found 436.0754.

Codeine (4)

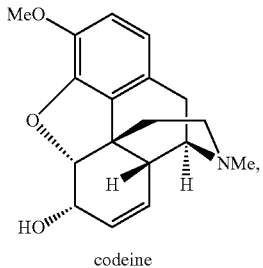

To the allylic alcohol 23 (10 mg, 0.023 mM), in THF (1.5 mL) was added LiAlH$_4$ (2M in THF, 0.3 mL) and the solution was stirred at 25° C. for 6 h. The reaction mixture was cooled to 0° C. and quenched with drop-wise addition of saturated aqueous Na$_2$SO$_4$ (0.5 mL). The salts were filtered over a pad of Celite and washed with diethyl ether (10 mL). The combined organics were dried (Na$_2$SO$_4$) and evaporated in vacuo to yield a pale yellow solid. The crude product was purified (SiO$_2$, 10% MeOH/CH$_2$Cl$_2$) to give codeine (6 mg, 87%). R$_f$=0.21 (10% MeOH/CH$_2$Cl$_2$). M.p. 151-153° C. IR (thin film) 3400, 2925, 1501, 1451 cm$^{-1}$. $^1$H NMR (300 MHz, CDCl$_3$) δ 6.66 (1H, d, J=8.4 Hz), 6.57 (1H, d, J=8.4 Hz), 5.71 (1H, d, J=10 Hz), 5.29 (1H, dt, J=10, 2.7 Hz), 4.90 (1H, dd, J=6.6 Hz), 4.18 (1H, m), 3.84 (3H, s), 3.36 (1H, m), 3.05 (1H, d, J=18.4 Hz), 2.69 (1H, s), 2.60 (1H, dd, J=12, 4.4 Hz), 2.45 (3H, s), 2.40 (1H, dd, J=12.4, 3.5 Hz), 2.31 (1H, dd, J=18.4, 6 Hz), 2.03-2.12 (1H, m), 1.88 (1H, d, J=12.8 Hz); $^{13}$C NMR (75 MHz, CDCl$_3$) δ 146.2, 142.0, 133.3, 130.8, 127.9, 126.8, 119.3, 112.7, 91.2, 66.3, 58.8, 58.7, 56.1, 46.3, 42.8, 40.4, 35.5, 20.3. HRMS calcd. for C$_{18}$H$_{22}$NO$_3$ (MH$^+$) 300.1599. Found 300.1601.

Morphine (5)

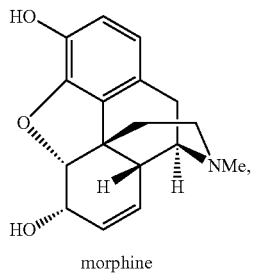

morphine

To a solution of codeine 4 (8 mg, 0.026 mM) in chloroform (2.5 mL) was added boron tribromide (1.0 M in $CH_2Cl_2$, 0.20 mmol) dropwise over 1 min and the resulting mixture was stirred at room temperature for 20 min. A solution of $NH_4OH$ (10% aq., 3 mL) was added dropwise at 0° C. The mixture was repeatedly extracted with a solution of 9:1 $CH_2Cl_2$/EtOH (4×15 mL) and the combined organics were washed with brine (25 mL), dried ($Na_2SO_4$) and concentrated in vacuo. The crude product was purified ($SiO_2$, 10% MeOH/$CH_2Cl_2$) to give morphine 5 (6.5 mg, 86% yield) as a white solid. $R_f$=0.06 (10% MeOH/$CH_2Cl_2$). M.p. 251-255° C. IR (thin film) 3352, 2924, 1459, 1249 $cm^{-1}$. $^1H$ NMR (300 MHz, $CDCl_3$) δ 6.62 (1H, d, J=8.1 Hz), 6.48 (1H, d, J=8.1 Hz), 5.67 (1H, d, J=9.9 Hz), 5.27 (1H, dt, J=9.9, 2.6 Hz), 4.84 (1H, dd, J=6.3 Hz), 4.18 (1H, m), 3.84 (3H, s), 3.36 (1H, m), 3.03 (1H, d, J=18.6 Hz), 2.66 (1H, m), 2.60 (1H, d, J=4.5 Hz), 2.47 (1H, dd, J=24.3, 3.6 Hz), 2.46 (1H, s), 2.34 (1H, dd, J=18.9, 6.3 Hz), 2.06 (1H, dt, J=12.9, 5.1 Hz), 1.90 (1H, d, J=12.9 Hz). $^{13}C$ NMR (75 MHz, $CDCl_3$) δ 145.6, 138.1, 132.7, 130.4, 127.9, 125.5, 119.5, 116.8, 91.1, 66.2, 58.7, 46.2, 42.7, 42.4, 40.0, 34.8, 20.4. HRMS calcd. for $C_{17}H_{20}NO_3$ ($MH^+$) 286.1443. Found 286.1445.

Example IV

Figure 7B:
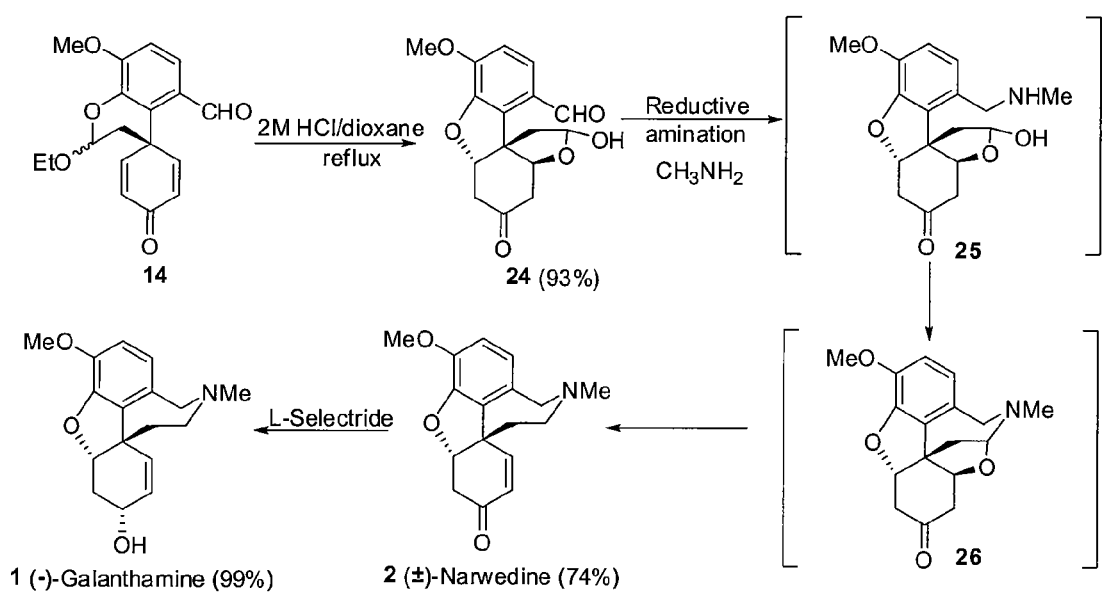
FIG. 7C provides specific (non-limiting) examples.

Acid catalyzed hydrolysis of 14 using 2M HCl in dioxane heated at reflux resulted in 24 (93%, 87.5% from 8, structure by X-ray), FIG. 3B then FIG. 7B. Reductive amination of 24 with $MeNH_2$ (1.2 eq)/THF (0.25 M)/$NaBH(OAc)_3$ (3.2 eq)/AcOH (5×) at 60° C. proceeded sequentially to give first 25, followed by the carbinolamine 26, and lastly (±)-narwedine 2 (74%) in a single reaction pot.

Compounds 2, 14, 24, 25 and 26 are racemates, but the structures are drawn in FIGS. 7A & B (for clarity) as a single enantiomer with their configuration corresponding to that of (−)-galanthamine.

Since (±)-narwedine has been converted into (−)-galanthamine 1 by spontaneous resolution followed by L-Selectride reduction in virtually quantitative yield, this completes the synthesis in an overall yield of 64.8% which is approximately five times the yield of the current commercial process.

Example V

Figure 7C:
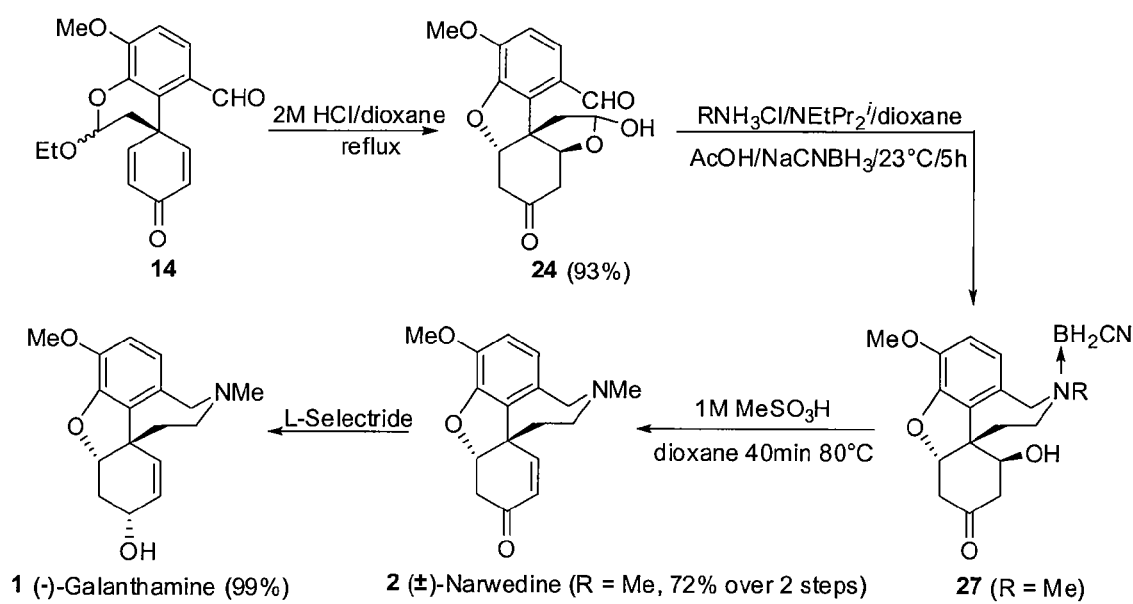
Figure 8A:
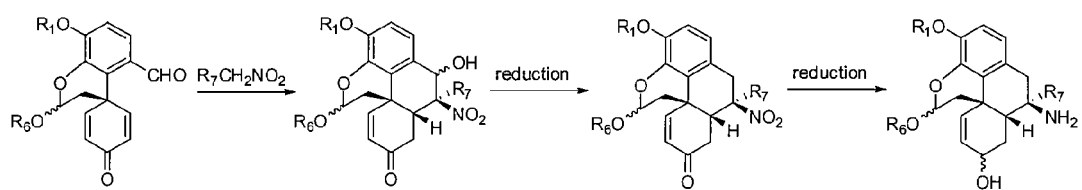
FIGS. 8A and B show embodiments of the present invention whereby certain $R_7$ derivatives of the cross-conjugate can be made.
Figure 8B:
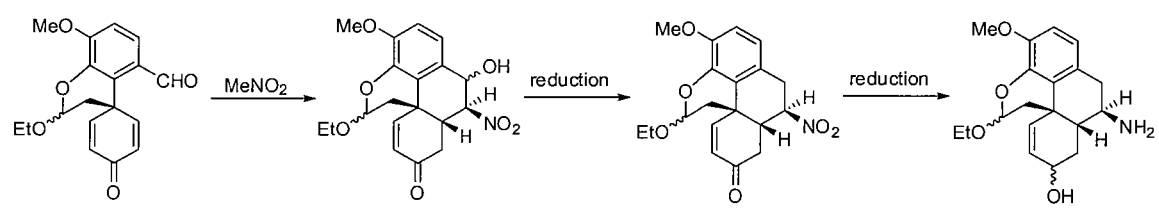
Figure 9A:
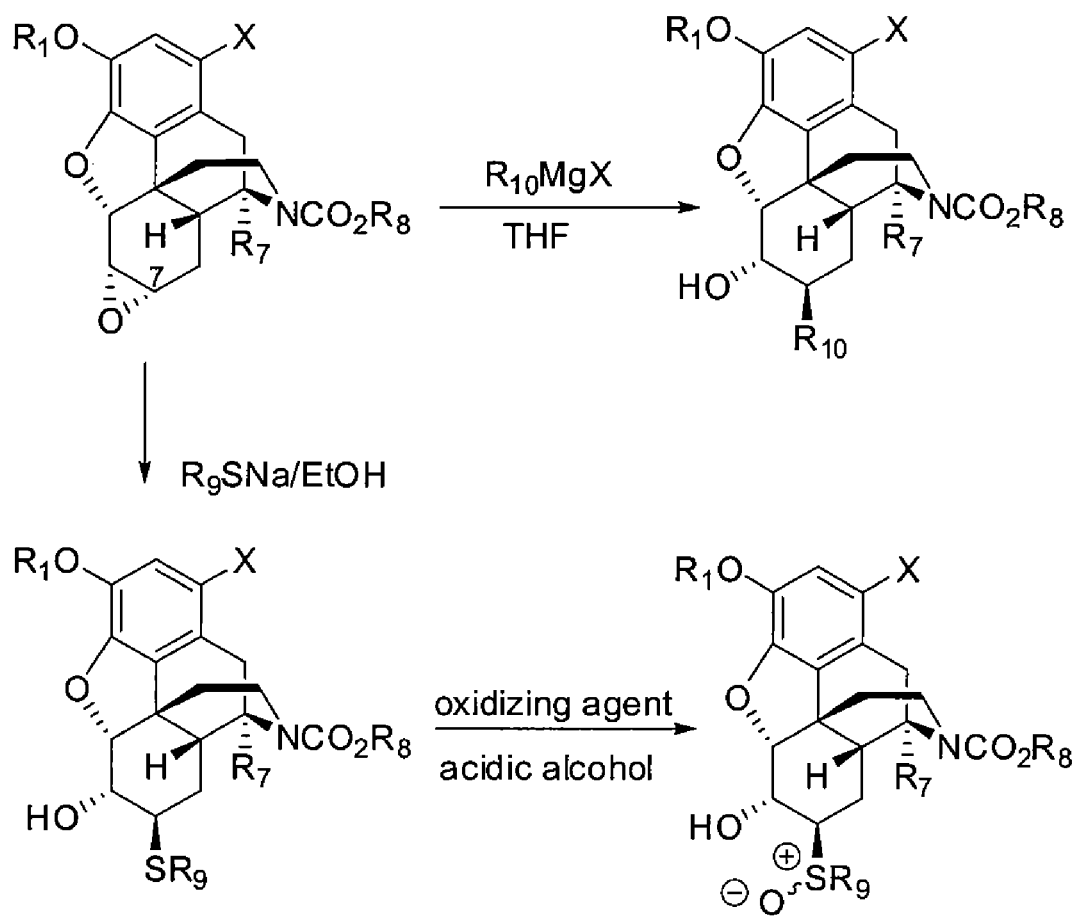
FIGS. 9A and B show embodiments of the present invention wherein a novel epoxide is used to make useful downstream derivatives (including but not limited to 7-β substituted 7,8-dihydro derivatives).
Figure 9B:
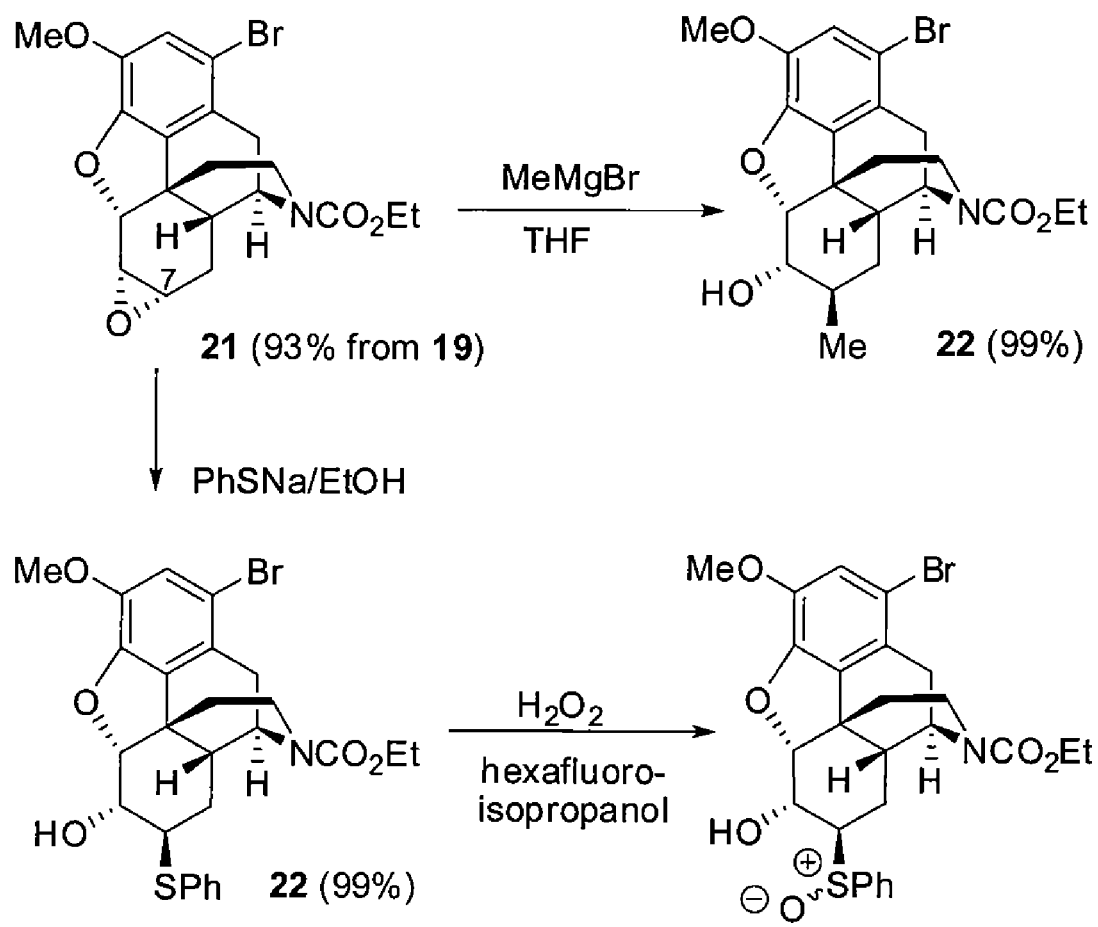
Figure 10:
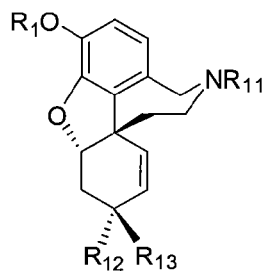
FIG. 10 shows the structure of some specific non-limiting examples of galanthamine derivatives, such as N-alkyl galanthamine derivatives [e.g. N-allylnorgalanthamine, N-(14-methylallyl)norgalanthamine, the structures for which are shown in FIG. 10].
Figure 10:
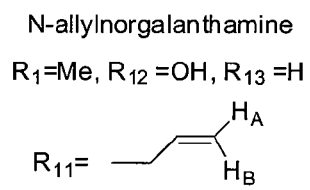
Figure 10:
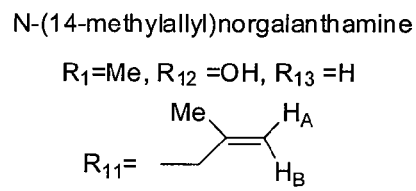

Acid catalyzed hydrolysis of 14 (FIG. 3B) using 2M HCl in dioxane heated at reflux resulted in 24 (93%, 87.5% from 8, structure by X-ray), FIG. 3B then FIG. 7C. Reductive amination of 24 with $MeNH_3Cl$/$NEtPr_2^i$/dioxane and $NaCNBH_3$/AcOH at 23° C. for 5 h proceeded to give 27, followed by the treatment with 1M $MeSO_3H$ under dioxane at 80° C. for 40 minutes to yield (±)-narwedine 2 (74%) in a single reaction pot.

Compounds 2, 14, 24, and 27 are racemates, but the structures are drawn in FIG. 7C (for clarity) as a single enantiomer with their configuration corresponding to that of (−)-galanthamine.

Since (±)-narwedine has been converted into (−)-galanthamine 1 by spontaneous resolution followed by L-Selectride reduction in virtually quantitative yield, this completes the synthesis in an overall yield of 64.8% which is approximately five times the yield of the current commercial process.

We claim:
1. A method of preparing a dihydro-1H-phenanthren-2-one derivative, comprising:
   a) providing a substituted biphenyl;
   b) treating said biphenyl under conditions so as to create a substituted biphenyl ether;
   c) treating said ether under conditions so as to create a cross-conjugated 2,5-cyclohexadienone; and
   d) treating the cross-conjugated 2,5-cyclohexadienone with a nitroalkane under Henry reaction conditions so as to create a dihydro-1H-phenanthren-2-one derivative.

2. The method of claim 1, wherein said dihydro-1H-phenanthren-2-one derivative is a nitroalkene or a β-hydroxy nitroalkane.

3. The method of claim 2, wherein said nitroalkene has the structure:

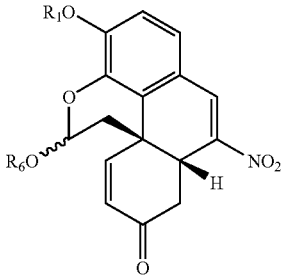

wherein $R_1$ is an alkyl, alkanediyl, alkynyl, aryl, arenediyl, aralkyl, heteroaryl, heteroarenediyl, heteroaralkyl, or a substituted version of any of these groups or a protecting group but not H; and $R_6$ can be alkyl, alkanediyl, alkynyl, aryl, arenediyl, aralkyl, heteroaryl, heteroarenediyl, heteroaralkyl, or a substituted version of any of these groups; and wherein said b-hydroxy nitroalkane has the structure:

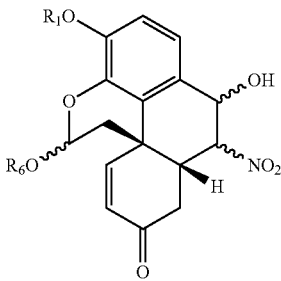

wherein $R_1$ is an alkyl, alkanediyl, alkynyl, aryl, arenediyl, aralkyl, heteroaryl, heteroarenediyl, heteroaralkyl, or a substituted version of any of these groups or a protecting group but not H; and $R_6$ can be an alkyl, alkanediyl, alkynyl, aryl, arenediyl, aralkyl, heteroaryl, heteroarenediyl, heteroaralkyl, or a substituted version of any of these groups.

4. The method of claim 1, wherein said dihydro-1H-phenanthren-2-one derivative is in the form of a mixture of epimers.

5. The method of claim 2, further comprising treating said nitroalkene with a reducing agent so as to create nitroalkane.

6. The method of claim 5, wherein said nitroalkane has the structure:

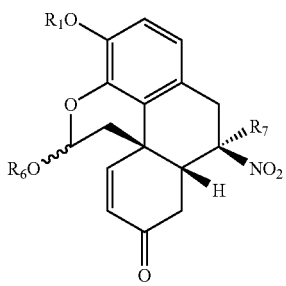

wherein $R_1$ is an alkyl, alkanediyl, alkynyl, aryl, arenediyl, aralkyl, heteroaryl, heteroarenediyl, heteroaralkyl, or a substituted version of any of these group or a protecting group, but not H; $R_6$ can be alkyl, alkanediyl, alkynyl, aryl, arenediyl, aralkyl, heteroaryl, heteroarenediyl, heteroaralkyl, or a substituted version of any of these groups; and $R_7$ can be alkyl, alkanediyl, alkynyl, aryl, arenediyl, aralkyl, heteroaryl, heteroarenediyl, heteroaralkyl, or a substituted version of any of these groups, or H.

7. The method of claim 5, wherein said nitroalkane is in the form of a mixture of epimers.

8. The method of claim 5, further comprising treating said nitroalkane with a reducing agent so as to create a primary amine.

9. The method of claim 8, wherein said amine has the structure:

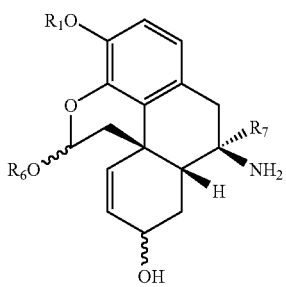

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, but not H; $R_6$ can be alkyl, alkanediyl, alkynyl, aryl, arenediyl, aralkyl, heteroaryl, heteroarenediyl, heteroaralkyl, or a substituted version of any of these groups; and $R_7$ can be alkyl, alkanediyl, alkynyl, aryl, arenediyl, aralkyl, heteroaryl, heteroarenediyl, heteroaralkyl, or a substituted version of any of these groups, or H.

10. The method of claim 8, further comprising treating said primary amine with a reducing agent so as to create a secondary amine.

11. The method of claim 10, wherein said secondary amine is the result of intramolecular reductive amination.

12. The method of claim 10, wherein said secondary amine has the structure:

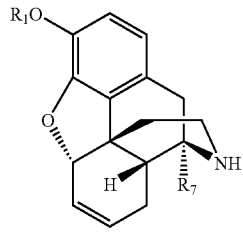

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; and $R_7$ can be H or an alkyl, alkanediyl, alkynyl, aryl, arenediyl, aralkyl, heteroaryl, heteroarenediyl, heteroaralkyl, or a substituted version of any of these groups.

13. The method of claim 10, further comprising treating said secondary amine with base so as to create a carbamate derivative.

14. The method of claim 13, wherein said carbamate derivative has the structure:

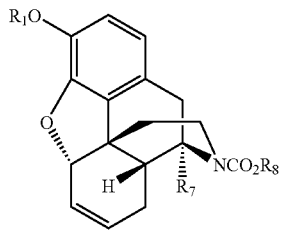

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is alkyl, alkanediyl, alkynyl, aryl, arenediyl, aralkyl, heteroaryl, heteroarenediyl, heteroaralkyl, or a substituted version of any of these groups, or H; and $R_8$ is an alkyl, alkanediyl, alkynyl, aryl, arenediyl, aralkyl, heteroaryl, heteroarenediyl, heteroaralkyl, or a substituted version of any of these groups.

15. The method of claim 10, further comprising treating said secondary amine with a carbon-halide, $R_8X$, where $R_8$ is an alkyl, alkanediyl, alkynyl, aryl, arenediyl, aralkyl, heteroaryl, heteroarenediyl, heteroaralkyl, or a substituted version of any of these groups; and X is F, Cl, Br, or I, so as to create a tertiary amine.

16. The method of claim 15, wherein said tertiary amine has the structure:

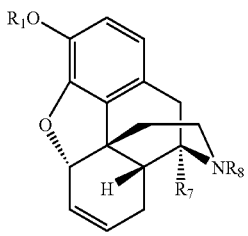

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is alkyl, alkanediyl, alkynyl, aryl, arenediyl, aralkyl, heteroaryl, heteroarenediyl, heteroaralkyl, or a substituted version of any of these groups, or H; and $R_8$ is an alkyl, alkanediyl, alkynyl, aryl, arenediyl, aralkyl, heteroaryl, heteroarenediyl, heteroaralkyl, or a substituted version of any of these groups.

17. The method of claim 13, further comprising treating said carbamate derivative with a halohydantoin so as to create a halohydrin.

18. The method of claim 17, wherein said halohydantoin is 2,2 bromo-3,5 dimethylhydantoin and said halohydrin is a bromohydrin.

19. The method of claim 18, wherein said bromohydrin has the structure:

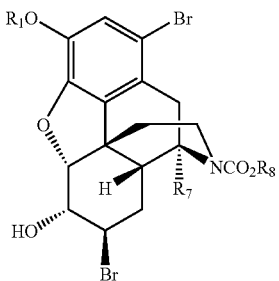

wherein $R_1$ is an alkyl, aryl, or heteroaryl group or a protecting group, or H; $R_7$ is alkyl, alkanediyl, alkynyl, aryl, arenediyl, aralkyl, heteroaryl, heteroarenediyl, heteroaralkyl, or a substituted version of any of these groups, or H; and $R_8$ is an alkyl, alkanediyl, alkynyl, aryl, arenediyl, aralkyl, heteroaryl, heteroarenediyl, heteroaralkyl, or a substituted version of any of these groups.

20. The method of claim 17, further comprising treating said halohydrin with base so as to create an epoxide.

21. The method of claim 20, wherein said epoxide has the structure:

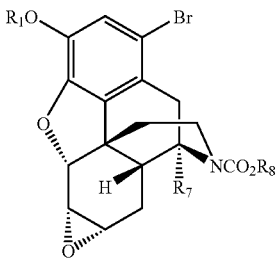

wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is alkyl, alkanediyl, alkynyl, aryl, arenediyl, aralkyl, heteroaryl, heteroarenediyl, heteroaralkyl, or a substituted version of any of these groups, or H; and $R_8$ is an alkyl, alkanediyl, alkynyl, aryl, arenediyl, aralkyl, heteroaryl, heteroarenediyl, heteroaralkyl, or a substituted version of any of these groups.

22. The method of claim 20, further comprising treating said epoxide with a reducing agent in the presence of an organic disulfide so as to create a phenyl sulfide.

23. The method of claim 22, wherein said phenyl sulfide has the structure:

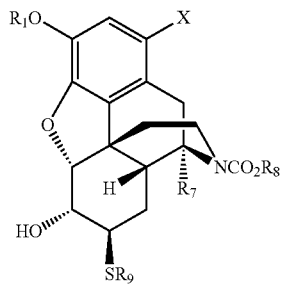

wherein $R_1$ is an alkyl, alkanediyl, alkynyl, aryl, arenediyl, aralkyl, heteroaryl, heteroarenediyl, heteroaralkyl, or a substituted version of any of these groups, or H; $R_7$ is an alkyl, alkanediyl, alkynyl, aryl, arenediyl, aralkyl, heteroaryl, heteroarenediyl, heteroaralkyl, or a substituted version of any of these groups, or H; $R_8$ is an alkyl, alkanediyl, alkynyl, aryl, arenediyl, aralkyl, heteroaryl, heteroarenediyl, heteroaralkyl, or a substituted version of any of these groups; $R_9$ is alkyl, alkanediyl, alkynyl, aryl, arenediyl, aralkyl, heteroaryl, heteroarenediyl, heteroaralkyl, or a substituted version of any of these groups; and X is F, Cl, Br, I or equivalent leaving group.

24. The method of claim 22, further comprising treating said phenylsulfide with hydrogen peroxide in the presence of hexafluoroisopropanol so as to create a sulfoxide.

25. The method of claim 24, wherein said sulfoxide has the structure:

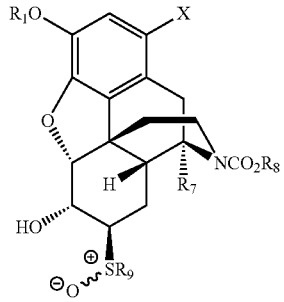

wherein $R_1$ is an alkyl, alkanediyl, alkynyl, aryl, arenediyl, aralkyl, heteroaryl, heteroarenediyl, heteroaralkyl, or a substituted version of any of these groups, or H; $R_7$ is an H or an alkyl, alkanediyl, alkynyl, aryl, arenediyl, aralkyl, heteroaryl, heteroarenediyl, heteroaralkyl, or a substituted version of any of these groups; $R_8$ is an alkyl, alkanediyl, alkynyl, aryl, arenediyl, aralkyl, heteroaryl, heteroarenediyl, heteroaralkyl, or a substituted version of any of these groups; $R_9$ is an aryl, or heteroaryl group; and X is F, Cl, Br, I or equivalent leaving group.

26. The method of claim 24, further comprising heating said sulfoxide to give an allylic alcohol.

27. The method of claim 26, wherein said allylic alcohol has the structure:

75

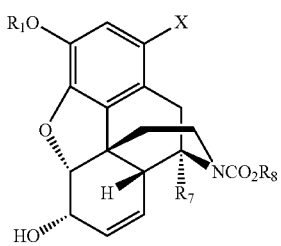

wherein $R_1$ is an alkyl, aryl, or heteroaryl group or a protecting group, or H; $R_7$ is an alkyl, alkanediyl, alkynyl, aryl, arenediyl, aralkyl, heteroaryl, heteroarenediyl, heteroaralkyl, or a substituted version of any of these groups, or H; $R_8$ is an alkyl, alkanediyl, alkynyl, aryl, arenediyl, aralkyl, heteroaryl, heteroarenediyl, heteroaralkyl, or a substituted version of any of these groups; and X is F, Cl, Br, I or equivalent leaving group.

28. The method of claim 26, further comprising treating said allylic alcohol with a reducing agent so as to create codeine.

29. The method of claim 28, further comprising treating said codeine with a Lewis acid so as to create morphine.

30. A composition of the formula:

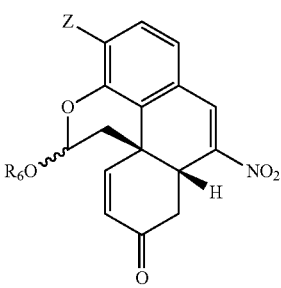

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups, or H or a protecting group; and $R_6$ can be an alkyl, alkanediyl, alkynyl, aryl, arenediyl, aralkyl, heteroaryl, heteroarenediyl, heteroaralkyl, or a substituted version of any of these groups.

31. A composition of the formula:

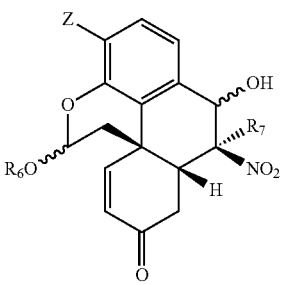

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_6$ can be alkyl, alkanediyl, alkynyl, aryl, arenediyl, aralkyl, heteroaryl, heteroarenediyl, heteroaralkyl, or a substituted version of any of these groups; and $R_7$ can be alkyl, alkanediyl, alkynyl, aryl, arenediyl,

76 aralkyl, heteroaryl, heteroarenediyl, heteroaralkyl, or a substituted version of any of these groups, or H.

32. A composition of the formula:

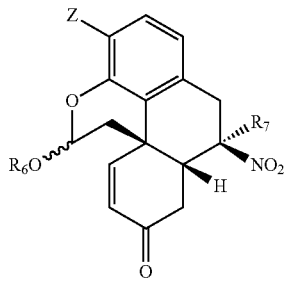

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_6$ can be alkyl, alkanediyl, alkynyl, aryl, arenediyl, aralkyl, heteroaryl, heteroarenediyl, heteroaralkyl, or a substituted version of any of these groups; and $R_7$ can be alkyl, alkanediyl, alkynyl, aryl, arenediyl, aralkyl, heteroaryl, heteroarenediyl, heteroaralkyl, or a substituted version of any of these groups, or H.

33. A composition of the formula:

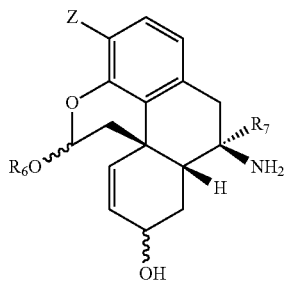

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_6$ can be alkyl, alkanediyl, alkynyl, aryl, arenediyl, aralkyl, heteroaryl, heteroarenediyl, heteroaralkyl, or a substituted version of any of these groups; and $R_7$ can be alkyl, alkanediyl, alkynyl, aryl, arenediyl, aralkyl, heteroaryl, heteroarenediyl, heteroaralkyl, or a substituted version of any of these groups, or H.

34. A composition of the formula:

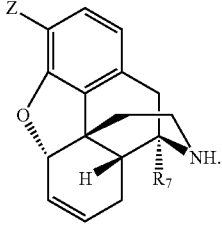

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; and $R_7$ can be H or an alkyl, alkanediyl, alkynyl, aryl, arenediyl, aralkyl, heteroaryl, heteroarenediyl, heteroaralkyl, or a substituted version of any of these groups.

35. A composition of the formula:

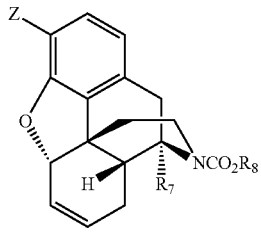

wherein Z is H or $R_1O$, wherein $R_1$ is alkyl, alkanediyl, alkynyl, aryl, arenediyl, aralkyl, heteroaryl, heteroarenediyl, heteroaralkyl, or a substituted version of any of these groups or a protecting group, or H; $R_7$ is H or an alkyl, alkanediyl, alkynyl, aryl, arenediyl, aralkyl, heteroaryl, heteroarenediyl, heteroaralkyl, or a substituted version of any of these groups; and $R_8$ is an alkyl, alkanediyl, alkynyl, aryl, arenediyl, aralkyl, heteroaryl, heteroarenediyl, heteroaralkyl, or a substituted version of any of these groups.

36. A composition of the formula:

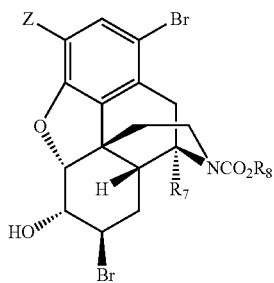

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is H or an alkyl, alkanediyl, alkynyl, aryl, arenediyl, aralkyl, heteroaryl, heteroarenediyl, heteroaralkyl, or a substituted version of any of these groups; and $R_8$ is an alkyl, alkanediyl, alkynyl, aryl, arenediyl, aralkyl, heteroaryl, heteroarenediyl, heteroaralkyl, or a substituted version of any of these groups.

37. A composition of the formula:

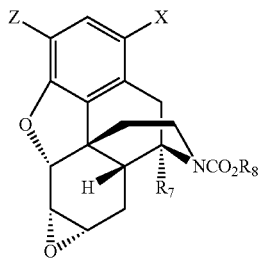

wherein Z is H or $R_1O$, wherein $R_1$ is an alkyl, aryl or heteroaryl group or a protecting group, or H; $R_7$ is H or an alkyl, alkanediyl, alkynyl, aryl, arenediyl, aralkyl, heteroaryl, heteroarenediyl, heteroaralkyl, or a substituted version of any of these groups; $R_8$ is an alkyl, alkanediyl, alkynyl, aryl, arenediyl, aralkyl, heteroaryl, heteroarenediyl, heteroaralkyl, or a substituted version of any of these groups; and X is F, Cl, Br, or I.

38. A composition of the formula:

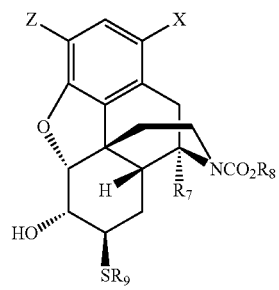

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is an H or an alkyl, alkanediyl, alkynyl, aryl, arenediyl, aralkyl, heteroaryl, heteroarenediyl, heteroaralkyl, or a substituted version of any of these groups group; $R_8$ is an alkyl, alkanediyl, alkynyl, aryl, arenediyl, aralkyl, heteroaryl, heteroarenediyl, heteroaralkyl, or a substituted version of any of these groups group; $R_9$ is an alkyl, alkanediyl, alkynyl, aryl, arenediyl, aralkyl, heteroaryl, heteroarenediyl, heteroaralkyl, or a substituted version of any of these groups group; and X is F, Cl, Br, or I.

39. A composition of the formula:

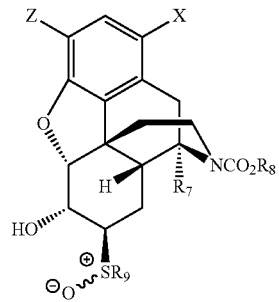

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is an H or an alkyl, alkanediyl, alkynyl, aryl, arenediyl, aralkyl, heteroaryl, heteroarenediyl, heteroaralkyl, or a substituted version of any of these groups group; $R_8$ is an alkyl, alkanediyl, alkynyl, aryl, arenediyl, aralkyl, heteroaryl, heteroarenediyl, heteroaralkyl, or a substituted version of any of these groups group; $R_9$ is an alkyl, alkanediyl, alkynyl, aryl, arenediyl, aralkyl, heteroaryl, heteroarenediyl, heteroaralkyl, or a substituted version of any of these groups group; and X is F, Cl, Br, or I.

40. The method of claim 20, further comprising treating the epoxide with Grignard reagent under conditions so as to form a epoxide ring opened 6-hydroxy,7-adduct.

41. A composition of the formula:

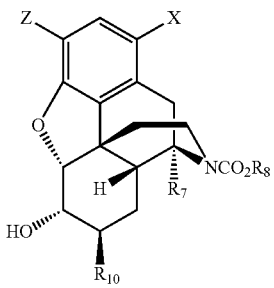

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is an H or an alkyl, aryl, or heteroaryl group or the like; $R_8$ is an alkyl, aryl, or heteroaryl group or the like $R_{10}$ is an alkyl, aryl, or heteroaryl group or the like (i.e. other groups such as alkanediyl, alkynyl, arenediyl, aralkyl, heteroarenediyl, heteroaralkyl, heteroaryl, alkenyl, alkenediyl, alkynediyl, acyl, alkylidene, non-carbon group, or a substituted version of any of these groups) or H; and X is a halide or an equivalent leaving group.

42. A composition of the formula:

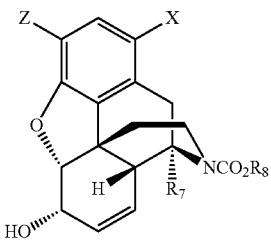

wherein Z is H or $R_1O$, wherein $R_1$ is an alkyl, alkanediyl, alkynyl, aryl, arenediyl, aralkyl, heteroaryl, heteroarenediyl, heteroaralkyl, or a substituted version of any of these groups or a protecting group, or H; $R_7$ is an H or an alkyl, alkanediyl, alkynyl, aryl, arenediyl, aralkyl, heteroaryl, heteroarenediyl, heteroaralkyl, or a substituted version of any of these groups group; $R_8$ is an alkyl, alkanediyl, alkynyl, aryl, arenediyl, aralkyl, heteroaryl, heteroarenediyl, heteroaralkyl, or a substituted version of any of these groups group; and X is F, Cl, Br, or I.

* * * * *